US011802293B2

(12) United States Patent
Linden

(10) Patent No.: US 11,802,293 B2
(45) Date of Patent: Oct. 31, 2023

(54) ADENO-ASSOCIATED VIRUS VECTOR

(71) Applicants: KING'S COLLEGE LONDON, London (GB); ICAHN SCHOOL OF MEDICINE AT MOUNT SINAI, New York, NY (US)

(72) Inventor: Ralph Michael Linden, London (GB)

(73) Assignees: KING'S COLLEGE LONDON, London (GB); ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 289 days.

(21) Appl. No.: 17/072,676

(22) Filed: Oct. 16, 2020

(65) Prior Publication Data

US 2021/0238631 A1 Aug. 5, 2021

Related U.S. Application Data

(63) Continuation of application No. 15/570,687, filed as application No. PCT/EP2015/053335 on Feb. 17, 2015, now abandoned.

(60) Provisional application No. 61/940,639, filed on Feb. 17, 2014.

(30) Foreign Application Priority Data

Mar. 3, 2014 (GB) ..................................... 1403684

(51) Int. Cl.

| | |
|---|---|
| ***C12N 15/86*** | (2006.01) |
| ***C07K 14/005*** | (2006.01) |
| ***A61P 27/02*** | (2006.01) |
| ***A61P 27/06*** | (2006.01) |
| ***A61P 1/16*** | (2006.01) |
| ***A61P 25/00*** | (2006.01) |
| ***A61K 48/00*** | (2006.01) |

(52) U.S. Cl.

CPC .......... *C12N 15/86* (2013.01); *A61K 48/0008* (2013.01); *A61P 1/16* (2018.01); *A61P 25/00* (2018.01); *A61P 27/02* (2018.01); *A61P 27/06* (2018.01); *C07K 14/005* (2013.01); *C12N 2750/14122* (2013.01); *C12N 2750/14142* (2013.01); *C12N 2750/14143* (2013.01)

(58) Field of Classification Search

CPC ........ A61K 48/0008; A61P 1/16; A61P 25/00; A61P 27/02; A61P 27/06; C07K 14/005; C12N 15/86; C12N 2750/14122; C12N 2750/14142; C12N 2750/14143

USPC .................................... 435/320.1; 424/93.21

See application file for complete search history.

(56) References Cited

U.S. PATENT DOCUMENTS

| | | | |
|---|---|---|---|
| 5,639,736 A | 6/1997 | Robinson | |
| 5,639,872 A | 6/1997 | Robinson | |
| 5,661,135 A | 8/1997 | Robinson | |
| 6,156,303 A | 12/2000 | Russell et al. | |
| 6,399,586 B1 | 6/2002 | Robinson | |
| 6,649,596 B1 | 11/2003 | Smyth et al. | |
| 7,198,951 B2 | 4/2007 | Gao et al. | |
| 7,271,002 B2 | 9/2007 | Kotin et al. | |
| 7,282,199 B2 | 10/2007 | Gao et al. | |
| 7,588,772 B2 | 9/2009 | Kay et al. | |
| 7,749,492 B2 | 7/2010 | Bartlett et al. | |
| 7,790,449 B2 | 9/2010 | Gao et al. | |
| 7,846,730 B2 | 12/2010 | Zhang et al. | |
| 7,892,809 B2 | 2/2011 | Bowles et al. | |
| 7,919,473 B2 | 4/2011 | de Fougerolles et al. | |
| 7,947,659 B2 | 5/2011 | de Fougerolles et al. | |
| 8,067,014 B2 | 11/2011 | Kay et al. | |
| 8,318,480 B2 | 11/2012 | Gao et al. | |
| 8,524,446 B2 | 9/2013 | Gao et al. | |
| 8,574,583 B2 | 11/2013 | Kay et al. | |
| 8,734,809 B2 | 5/2014 | Gao et al. | |
| 8,802,080 B2 | 8/2014 | Warrington et al. | |
| 8,906,675 B2 | 12/2014 | Gao et al. | |
| 8,945,918 B2 | 2/2015 | Chen | |
| 8,962,330 B2 | 2/2015 | Gao et al. | |
| 8,999,678 B2 * | 4/2015 | Vandenberghe ........ | A61P 31/12 435/320.1 |
| 9,102,949 B2 | 8/2015 | Gao et al. | |
| 9,169,299 B2 | 10/2015 | Lisowski et al. | |
| 9,198,984 B2 | 12/2015 | Lock et al. | |

(Continued)

FOREIGN PATENT DOCUMENTS

| | | |
|---|---|---|
| CN | 1856576 A | 11/2006 |
| CN | 101203613 A | 6/2008 |

(Continued)

OTHER PUBLICATIONS

Chen et al. Journal of Virology, Dec. 2005, p. 14781-14792. (Year: 2005).*

(Continued)

*Primary Examiner* — Janet L Epps-Smith

(74) *Attorney, Agent, or Firm* — MEDLER FERRO WOODHOUSE & MILLS

(57) ABSTRACT

Disclosed herein is a recombinant adeno-associated virus (AAV) vector comprising (a) a variant AAV2 capsid protein, wherein the variant AAV2 capsid protein comprises at least four amino acid substitutions with respect to a wild type AAV2 capsid protein; wherein the at least four amino acid substitutions are present at the following positions in an AAV2 capsid protein sequence: 457, 492, 499 and 533; and (b) a heterologous nucleic acid comprising a nucleotide sequence encoding a gene product.

7 Claims, 23 Drawing Sheets

(22 of 23 Drawing Sheet(s) Filed in Color)

Specification includes a Sequence Listing.

(56) References Cited

U.S. PATENT DOCUMENTS

| | | | |
|---|---|---|---|
| 9,233,131 B2 | 1/2016 | Schaffer et al. | |
| 9,441,244 B2 | 9/2016 | Schaffer et al. | |
| 9,611,302 B2 | 4/2017 | Srivastava et al. | |
| 9,677,088 B2 | 6/2017 | Nakai et al. | |
| 9,725,485 B2 | 8/2017 | Srivastava et al. | |
| 9,856,469 B2 | 1/2018 | Lisowski et al. | |
| 10,006,049 B2 | 6/2018 | Ling et al. | |
| 10,046,016 B2 | 8/2018 | Schaffer et al. | |
| 10,214,566 B2 | 2/2019 | Schaffer et al. | |
| 10,294,281 B2 | 5/2019 | Srivastava et al. | |
| 10,308,957 B2 | 6/2019 | Boye et al. | |
| 2002/0192823 A1 | 12/2002 | Bartlett | |
| 2003/0138772 A1 | 7/2003 | Gao et al. | |
| 2005/0053922 A1 | 3/2005 | Schaffer et al. | |
| 2005/0106558 A1 | 5/2005 | Perabo et al. | |
| 2008/0188437 A1 | 8/2008 | Tolentino et al. | |
| 2008/0269149 A1* | 10/2008 | Bowles | A61P 43/00 435/320.1 |
| 2009/0202490 A1 | 8/2009 | Schaffer et al. | |
| 2009/0203071 A1 | 8/2009 | Chen | |
| 2009/0215879 A1 | 8/2009 | Diprimio et al. | |
| 2009/0317417 A1 | 12/2009 | Vandenberghe et al. | |
| 2010/0260800 A1 | 10/2010 | Bartlett et al. | |
| 2010/0297177 A1 | 11/2010 | Buening et al. | |
| 2011/0104119 A1 | 5/2011 | Bowles et al. | |
| 2011/0143400 A1 | 6/2011 | Reich et al. | |
| 2012/0046349 A1 | 2/2012 | Bell et al. | |
| 2012/0070899 A1 | 3/2012 | Sharifi et al. | |
| 2018/0057840 A1 | 3/2018 | Hauswirth et al. | |
| 2018/0105559 A1 | 4/2018 | Srivastava et al. | |
| 2018/0135076 A1 | 5/2018 | Linden | |
| 2018/0230440 A1 | 8/2018 | Ho et al. | |
| 2018/0258420 A1 | 9/2018 | Lisowski et al. | |
| 2018/0258447 A1 | 9/2018 | Ling et al. | |
| 2018/0289757 A1 | 10/2018 | Schaffer et al. | |
| 2019/0169237 A1 | 6/2019 | Schaffer et al. | |
| 2019/0314522 A1 | 10/2019 | Pchejetsky et al. | |

FOREIGN PATENT DOCUMENTS

| | | | |
|---|---|---|---|
| CN | 102071206 | A | 5/2011 |
| CN | 102174574 | A | 9/2011 |
| CN | 103561774 | A | 2/2014 |
| EP | 1486567 | A1 | 12/2004 |
| EP | 1828390 | B1 | 6/2012 |
| EP | 3485005 | A1 | 5/2019 |
| EP | 3108000 | B1 | 8/2019 |
| EP | 3113787 | B1 | 12/2019 |
| EP | 3356390 | B1 | 1/2021 |
| JP | 2007-207223 | A | 8/2007 |
| JP | 2008-538286 | A | 10/2008 |
| JP | 6602788 | B2 | 11/2019 |
| WO | WO 98/11244 | A2 | 3/1998 |
| WO | WO 99/61601 | | 12/1999 |
| WO | WO 00/28061 | A2 | 5/2000 |
| WO | 2003/052051 | A1 | 6/2003 |
| WO | 2003/052052 | A2 | 6/2003 |
| WO | WO 2004/027019 | A2 | 4/2004 |
| WO | WO 2004/112727 | A2 | 12/2004 |
| WO | 2005/033321 | A2 | 4/2005 |
| WO | WO 2005/033321 | A2 | 4/2005 |
| WO | WO 2006/066066 | A2 | 6/2006 |
| WO | 2006/110689 | A2 | 10/2006 |
| WO | WO 2006/110689 | A2 | 10/2006 |
| WO | 2007/127264 | A2 | 11/2007 |
| WO | WO 2009/137006 | A2 | 11/2009 |
| WO | 2010/093784 | A2 | 8/2010 |
| WO | 2010/138263 | A2 | 12/2010 |
| WO | WO 2011/011572 | A1 | 1/2011 |
| WO | 2011/133890 | A1 | 10/2011 |
| WO | 2012/145601 | A2 | 10/2012 |
| WO | WO 2012/145601 | A2 | 10/2012 |
| WO | WO 2013/029030 | A1 | 2/2013 |
| WO | 2013/173129 | A2 | 11/2013 |
| WO | WO 2013/170078 | A1 | 11/2013 |
| WO | WO 2014/186746 | A1 | 11/2014 |
| WO | 2015/121501 | A1 | 8/2015 |
| WO | WO 2015/121501 | A1 | 8/2015 |
| WO | WO 2015/134643 | A1 | 9/2015 |
| WO | WO 2016/133917 | A1 | 8/2016 |
| WO | WO 2017/058892 | A2 | 4/2017 |
| WO | WO 2017/189959 | A1 | 11/2017 |
| WO | WO 2018/011572 | A1 | 1/2018 |

OTHER PUBLICATIONS

Adachi, K. et al., "Drawing a high-resolution functional map of adeno-associated virus capsid by massively parallel seguencing," Nature Communications 5(3075), Jan. 17, 2014, pp. 1-14.

Akiyama, H. et al., "Intraocular Injection of an Aptamer that Binds PDGF-B: A Potential Treatment for Proliferative Retinopathies," Journal of Cellular Physiology, vol. 207, May 2006, pp. 407-412.

Andersen, J.K. et al., "Herpesvirus-Mediated Gene Delivery into the Rat Brain: Specificity and Efficiency of the Neuron-Specific Enolase Promoter," Cellular and Molecular Neurobiology, vol. 13, No. 5, Oct. 1993, pp. 503-515.

Archer, L.D. et al., "Mucopolysaccharide diseases: A complex interplay between neuroinflammation, microglial activation and adaptive immunity," Journal of Inherited Metabolic Disease, vol. 37, May 8, 2013, pp. 1-12.

Aslanidi, G.V. et al., "Optimization of the Capsid of Recombinant Adeno-Associated Virus 2 (AAV2) Vectors: The Final Threshold?," PLOS One, vol. 8, Iss. 3, Mar. 2013, pp. 1-12.

Asokan, A. et al., "Reengineering a receptor footprint of adeno-associated virus enables selective and systemic gene transfer to muscle," Nature Biotechnology, vol. 28, No. 1, Jan. 2010, pp. 79-82.

Bainbridge, J.W.B. et al., "Long-Term Effect of Gene Therapy on Leber's Congenital Amaurosis," The New England Journal of Medicine, vol. 372, No. 20, May 14, 2015, pp. 1887-1897.

Bantel-Schaal, U. et al., "Human Adeno-Associated Virus Type 5 Is Only Distantly Related to Other Known Primate Helper-Dependent Parvoviruses," Journal of Virology, vol. 73, No. 2, Feb. 1999, pp. 939-947.

Bartel, M. et al., "Enhancing the clinical potential of AAV vectors by capsid engineering to evade pre-existing immunity," Frontiers in Microbiology, vol. 2, Article 204, Oct. 2011, pp. 1-10.

Bennett, A. et al., "Thermal Stability as a Determinant of AAV Serotype Identity," Molecular Therapy Methods & Clinical Development, vol. 6, Sep. 15, 2017, pp. 171-182.

Bevan, A.K. et al., "Systemic Gene Delivery in Large Species for Targeting Spinal Cord, Brain, and Peripheral Tissues for Pediatric Disorders," Molecular Therapy, vol. 19, No. 11, Nov. 2011, pp. 1971-1980.

Biasini, M. et al., "Swiss-Model: modelling protein tertiary and quaternary structure using evolutionary information," Nucleic Acids Research, vol. 42, Jul. 2014, pp. W252-W258.

Bosch, M.E. et al., "Self-Complementary AAV9 Gene Delivery Partially Corrects Pathology Associated with Juvenile Neuronal Ceroid Lipofuscinosis (CLN3)," The Journal of Neuroscience 36(37), Sep. 14, 2016, pp. 9669-9682.

Boye, S.L. et al., "Impact of heparan sulfate binding on transduction of retina by recombinant adeno-associated virus vectors," Journal of Virology, vol. 90, No. 8, Apr. 2016, pp. 4215-4231.

Burger, C. et al., "Recombinant AAV Viral Vectors Pseudotyped with Viral Capsids from Serotypes 1, 2, and 5 Display Differential Efficiency and Cell Tropism after Delivery to Different Regions of the Central Nervous System," Molecular Therapy, vol. 10, No. 2, Aug. 2004, pp. 302-317.

Canal, M. et al., "Circadian rhythm and suprachiasmatic nucleus alterations in the mouse model of mucopolysaccharidosis IIIB," Behavioural Brain Research, vol. 209, Feb. 4, 2010, pp. 212-220.

Carrillo-Tripp, M. et al., "VIPERdb2: an enhanced and web API enabled relational database for structural virology," Nucleic Acids Research, vol. 37, Nov. 3, 2008, pp. D436-D442.

(56) References Cited

OTHER PUBLICATIONS

Cearley, C.N. et al., "Transduction Characteristics of Adeno-associated Virus Vectors Expressing Cap Serotypes 7, 8, 9, and Rh10 in the Mouse Brain," Molecular Therapy, vol. 13, No. 3, Mar. 2006, pp. 528-537.
Chen, C-L. et al., "Molecular Characterization of Adeno-Associated Viruses Infecting Children," Journal of Virology, vol. 79, No. 23, Dec. 2005, pp. 14781-14792.
Chen, Y.H. et al., "Molecular signatures of disease brain endothelia provide new sites for CNS-directed enzyme therapy," Nature Medicine, vol. 15, No. 10, Oct. 2009, pp. 1215-1218.
Chiorini, J.A. et al., "Cloning and Characterization of Adeno-Associated Virus Type 5," Journal of Virology, vol. 73, No. 2, Feb. 1999, pp. 1309-1319.
Chiorini, J.A. et al., "Cloning of Adeno-Associated Virus Type 4 (AAV4) and Generation of Recombinant AAV4 Particles," Journal of Virology, vol. 71, No. 9, Sep. 1997, pp. 6823-6833.
Cubillo, A. et al., "A review of fronto-striatal and fronto-cortical brain abnormalities in children and adults with Attention Deficit Hyperactivity Disorder (ADHD) and new evidence for dysfunction in adults with ADHD during motivation and attention," Cortex, vol. 48, Apr. 27, 2011, pp. 194-215.
Deacon, R. et al., "Effects of cytotoxic hippocampal lesions in mice on a cognitive test battery," Behavioural Brain Research, vol. 133, May 31, 2002, pp. 57-68.
Drouin, L. et al., "Adeno-associated virus structural biology as a tool in vector development," Future Viro. 8(12), Dec. 2013, pp. 1183-1199.
Durand, S. et al., "Analysis of the biogenesis of heparan sulfate acetyl-coA: α glucosaminide N-acetyltransferase provides insights into the mechanism underlying its complete deficiency in mucopolysaccharidosis IIIC," The Journal of Biological Chemistry, vol. 285, No. 41, Oct. 8, 2010, pp. 31233-31242.
Ellinwood, N.M. et al., "Safe, Efficient, and Reproducible Gene Therapy of the Brain in the Dog Models of Sanfilippo and Hurler Syndromes," Molecular Therapy, vol. 19, No. 2, Dec. 7, 2010, pp. 251-259.
Fagone, P. et al., "Systemic Errors in Quantitative Polymerase Chain Reaction Titration of Self-Complementary Adeno-Associated Viral Vectors and Improved Alternative Methods," Human Gene Therapy Methods 23(1), Feb. 2012, pp. 1-7.
Foust, K.D et al., "Intravascular AAV9 preferentially targets neonatal neurons and adult astrocytes," Nature Biotechnology, vol. 27, No. 1, Jan. 2009, pp. 59-65.
Fu, H. et al., "Neurological Correction of Lysosomal Storage in a Mucopolysaccharidosis IIIB Mouse Model by Adeno-associated Virus-Mediated Gene Delivery," Molecular Therapy, vol. 5, No. 1, Jan. 2002, pp. 42-49.
Gao, G. et al., "Clades of adeno-associated viruses are widely disseminated in human tissues," Journal of Virology, vol. 78, No. 12, Jun. 2004, pp. 6381-6388.
Gao, G. et al., "Novel adeno-associated viruses from rhesus monkeys as vectors for human gene therapy," PNAS, vol. 99, No. 18, Sep. 3, 2002, pp. 11854-11859.
Genbank, Capsid protein VP1 [Adeno-associated virus], GenBank: AAU05358.1, Nov. 15, 2005, pp. 1-2.
George, D.G. et al., "Current Methods in Sequence Comparison and Analysis, Macromolecule Sequencing and Synthesis, Selected Methods and Applications," Chapter 12: Macromolecular Sequencing and Synthesis Selected Methods and Applications, 1988, pp. 127-149.
Georgiadis, A. et al., "Development of an optimized AAV2/5 gene therapy vector for Leber congenital amaurosis owing to defects in RPE65," Gene Therapy, vol. 23, Sep. 22, 2016, pp. 857-862.
Grainger, S.M et al., "Infectious Titer Assay for Recombinant Adeno-Associated Virus Vectors Using Direct Cell Lysis and End-point Taqman PCR," Molecular Therapy, vol. 11, Supplement 1, May 2005, pp. S337.
Grifman, M. et al., "Incorporation of Tumor-Targeting Peptides into Recombinant Adeno-associated Virus Capsids," Molecular Therapy, vol. 3, No. 6, Jun. 2001, pp. 964-975.
Grimm, D. et al., "Novel tools for production and purification of recombinant adenoassociated virus vectors," Human Gene Therapy 9(18), Dec. 10, 1998, pp. 2745-2760.
Gurda, B.L. et al., "Capsid Antibodies to Different Adeno-Associated Virus Serotypes Bind Common Regions," Journal of Virology, vol. 87. No. 16, Aug. 2013, pp. 9111-9124.
Hafenrichter, D.G. et al., "Quantitative Evaluation of Liver-Specific Promoters From Retroviral Vectors After In Vivo Transduction of Hepatocytes," Blood, vol. 84, No. 10, Nov. 10, 1994, pp. 3394-3404.
Heard, J-M. et al., "Determinants of Rat Albumin Promoter Tissue Specificity Analyzed by an Improved Transient Expression System," Molecular and Cellular Biology, vol. 7, No. 7, Jul. 1987, pp. 2425-2434.
Herculano-Houzel, S., "The Glia/Neuron Ratio: How it Varies Uniformly Across Brain Structures and Species and What that Means for Brain Physiology and Evolution," Glia, vol. 62, May 7, 2014, pp. 1377-1391.
Hock, B.J. et al., "Differential Effects of Dorsal and Ventral Hippocampal Lesions," The Journal of Neuroscience 18(17), Sep. 1, 1998, pp. 7027-7032.
Holley, R.J. et al., "Macrophage enzyme and reduced inflammation drive brain correction of mucopolysaccharidosis IIIB by stem cell gene therapy," Brain, vol. 141, Iss. 1, Jan. 2018, pp. 99-116.
Hughes, R.N., "The value of spontaneous alternation behavior (SAB) as a test of retention in pharmacological investigations of memory," Neuroscience and Biobehavioral Reviews, vol. 28, Sep. 2004, pp. 497-505.
Kaiser, P.K. et al., "RNAi-Based Treatment for Neovascular Age-Related Macular Degeneration by Sirna-027," American Journal of Ophthalmology, vol. 150, Iss. 1, Jul. 2010, pp. 33-39.e2.
Kanaan, N.M. et al., "Rationally Engineered AAV Capsids Improve Transduction and Volumetric Spread in the CNS," Molecular Therapy Nucleic Acids, vol. 8, Sep. 15, 2017, pp. 184-197.
Kern, A. et al., "Identification of a Heparin-Binding Motif on Adeno-Associated Virus Type 2 Capsids," Journal of Virology, vol. 77, No. 20, Oct. 2003, p. 11072-11081.
Kim, J-Y. et al., "Viral transduction of the neonatal brain delivers controllable genetic mosaicism for visualising and manipulating neuronal circuits in vivo," European Journal of Neuroscience, vol. 37, Jan. 24, 2013, pp. 1203-1220.
Klein, R.L. et al., "AAV8, 9, Rh10, Rh43 Vector Gene Transfer in the Rat Brain: Effects of Serotype, Promoter and Purification Method," Molecular Therapy, vol. 16, No. 1, Jan. 2008, pp. 89-96.
Klein, R.L. et al., "Efficient Neuronal Gene Transfer with AAV8 Leads to Neurotoxic Levels of Tau or Green Fluorescent Proteins," Molecular Therapy, vol. 13, No. 3, Mar. 2006, pp. 517-527.
Kohlbrenner, E. et al., "Quantification of AAV Particle Titers by Infrared Fluorescence Scanning of Coomassie-Stained Sodium Dodecyl Sulfate-Polyacrylamide Gels," Human Gene therapy Methods 23(3), Jun. 2012, pp. 198-203.
Kotterman, M.A. et al., "Engineering adeno-associated viruses for clinical gene therapy," Nature Reviews, vol. 15, Jul. 2014, pp. 445-451.
Kou, R. et al., "Differential Regulation of Vascular Endothelial Growth Factor Receptors (VEGFR) Revealed by RNA Interference: Interactions of VEGFR-1 and VEGFR-2 in Endothelial Cell Signaling," Biochemistry, vol. 44, Oct. 21, 2005, pp. 15064-15073.
Lai, C-M. et al., "Long-Term Evaluation of AAV-Mediated sFlt-1 Gene Therapy for Ocular Neovascularization in Mice and Monkeys," Molecular Therapy, vol. 12, No. 4, Oct. 2005, pp. 659-668.
Langford-Smith, A. et al., "Female mucopolysaccharidosis IIIA mice exhibit hyperactivity and a reduced sense of danger in the open field test," PLoS One, Oct. 18, 2011, pp. 1-10.
Lee, J-H. et al., "A therapeutic aptamer inhibits angiogenesis by specifically targeting the heparin binding domain ofVEGF165," PNAS, vol. 102, No. 52, Dec. 27, 2005, p. 18902-18907.
Lisowski, L. et al., "Selection and evaluation of clinically relevant AAV variants in a xenograft liver model," Nature, vol. 506, Feb. 20, 2014, pp. 382-386.

(56) References Cited

OTHER PUBLICATIONS

Martins, C. et al., "Neuroinflammation, mitochondrial defects and neurodegeneration in mucopolysaccharidosis III type C mouse model," Brain 138 (Pt 2), Feb. 2015, pp. 336-355.
Mastakov, M.Y. et al., "Recombinant adeno associated virus serotypes 2- and 5-mediated gene transfer in the mammalian brain: quantitative analysis of heparin co-infusion," Molecular Therapy, vol. 5, Iss. 4, Apr. 2002, pp. 371-380.
McGlynn, R. et al., "Differential subcellular localization of cholesterol, gangliosides, And glycosaminoglycans in murine models of mucopolysaccharide storage disorders," The Journal of Comparative Neurology, vol. 480, Iss. 4, Nov. 22, 2004, pp. 415-426.
Mendell, J.R. et al., "Single-Dose Gene-Replacement Therapy for Spinal Muscular Atrophy," New England Journal of Medicine, vol. 377, No. 18, Nov. 2, 2017, pp. 1713-1722.
Mingozzi, F. et al., "Overcoming preexisting humoral immunity to AAV using capsid decoys," Science Translational Medicine, vol. 5, Iss. 194, Jul. 17, 2013, pp. 194ra92.
Mori, S. et al., "Two novel adeno-associated viruses from cynomolgus monkey: pseudotyping characterization of capsid protein," Virology, vol. 330, Iss. 2, Nov. 2, 2004, pp. 375-383.
Morris, L.S. et al., "Fronto-striatal organization: Defining functional and microstructural substrates of behavioural flexibility," Cortex, vol. 74, Jan. 2016, pp. 118-133.
Müller, O.J. et al., "Random peptide libraries displayed on adeno-associated virus to select for targeted gene therapy vectors," Nature Biotechnology, vol. 21, Aug. 3, 2003, pp. 1040-1043.
Muramatsu, S-I. et al., "Nucleotide Sequencing and Generation of an Infectious Clone of Adeno-Associated Virus 3," Virology, vol. 221, Iss. 1, Jul. 1996, pp. 208-217.
Nathwani, A. C. et al., "Long-Term Safety and Efficacy of Factor IX Gene Therapy in Hemophilia B," The New England Journal of Medicine, vol. 371, Nov. 20, 2014, pp. 1994-2004.
NCBI Reference Sequence YP_680426.1, Nov. 19, 2010, pp. 1-2.
Needleman, S.B. et al., "A general method applicable to the search for similarities in the amino acid sequence of tow proteins," Journal of Molecular Biology, vol. 48, Iss. 3, Mar. 28, 1970, pp. 443-453.
Ng, E. et al., "Pegaptanib, a targeted anti-VEGF aptamer for ocular vascular disease," Nature Reviews Drug Discovery, vol. 5, Feb. 1, 2006, pp. 123-132.
Nguyen, J. B. et al., "Convection-enhanced delivery of AAV-2 combined with heparin increases TK gene transfer in the rat brain," Neuroreport, vol. 12, Iss. 9, Jul. 3, 2001, pp. 1961-1964.
Ni, Z. et al., "Emerging Pharmacologic Therapies for Wet Age-Related Macular Degeneration," Ophthalmologica, vol. 223, Oct. 2009, pp. 401-410.
Nicoud, M. et al., "Development of photoreceptor-specific promoters and their utility to investigate EIAV lentiviral vector mediated gene transfer to photoreceptors," The Journal of Gene Medicine, vol. 9, Iss. 12, Dec. 2007, pp. 1015-1023.
O'Leary, C. et al., "Phenotypic effects of maternal immune Activation and early postnatal milieu in mice mutant for the schizophrenia risk gene neuregulin-1," Neuroscience, vol. 277, Sep. 26, 2014, pp. 294-305.
Ohmi, K. et al., "Defects in the medial entorhinal cortex and dentate gyrus in the mouse model of Sanfilippo syndrome type B," PLoS One, Nov. 9, 2011, pp. 1-10.
Opie, S.R. et al., "Identification of amino acid residues in the capsid proteins of adeno-associated virus type 2 that contribute to heparan sulfate proteoglycan binding," Journal of Virology, vol. 77, Jun. 2003, pp. 6995-7006.
Pacouret, S. et al., "AAV-ID: A Rapid and Robust Assay for Batch-to-Batch Consistency Evaluation of AAV Preparations," Molecular Therapy, vol. 25, Iss. 6, Jun. 7, 2017, pp. 1375-1386.
PCT International Search Report and Written Opinion, PCT Application No. PCT/EP2015/053335, dated Jul. 6, 2015, 17 pages.
Pechan, P. et al., "Novel anti-VEGF chimeric molecules delivered by AAV vectors for inhibition of retinal neovascularization," Gene Therapy, vol. 16, Jul. 17, 2008, pp. 10-16.
Perabo, L. et al., "Heparan sulfate proteoglycan binding properties of adeno-associated virus retargeting mutants and consequences for their in vivo tropism," Journal of Virology, vol. 80, Jul. 2006, pp. 7265-7269.
Piccioli, P. et al., "Neuroantibodies: Ectopic expression of a recombinant anti-substance P antibody in the central nervous system of transgenic mice," Neuron, vol. 15, Iss. 2, Aug. 1995, pp. 373-384.
Piccioli, P. et al., "Neuroantibodies: molecular cloning of a monoclonal antibody against substance P for expression in the central nervous system," PNAS 88(13), Jul. 1, 1991, pp. 5611-5615.
Porras, G. et al., "Viral Vectors in Primate Research: Examples from Parkinson's Disease Research," Viral Vector Approaches in Neurobiology and Brain Diseases, Neuromethods, vol. 82, Sep. 19, 2013, pp. 331-341.
Rahim, A.A. et al., "In utero administration of Ad5 and AAV pseudotypes to the fetal brain leads to efficient, widespread and long-term gene expression," Gene Therapy, vol. 19, Nov. 10, 2011, pp. 936-946.
Rawlins, J.N.P. et al., "The septo-hippocampal system and cognitive mapping," Behavioural Brain Research, vol. 5, Iss. 4, Aug. 1982, pp. 331-358.
Rayaprolu, V. et al., "Comparative analysis of adeno-associated virus capsid stability and dynamics," Journal of Virology 87(24), Dec. 2013, pp. 13150-13160.
Rayaprolu, V. et al., "Fluorometric Estimation of Viral Thermal Stability," Bio Protoc. 4(15), Aug. 5, 2014, e1199, pp. 1-5.
Reich, S.J. et al., "Small interfering RNA (siRNA) targeting VEGF effectively inhibits ocular neovascularization in a mouse model," Molecular Vision, vol. 9, May 30, 2003, pp. 210-216.
Ripamonti, C. et al., "Spectral sensitivity measurements reveal partial success in restoring missing rod function with gene therapy," Journal of Vision, vol. 15, Nov. 2015, pp. 1-16.
Ruijter, G.J.G. et al., "Clinical and genetic spectrum of Sanfilippo type C (MPS IIIC) disease in The Netherlands," Molecular Genetics and Metabolism, vol. 93, Iss. 2, Feb. 2008, pp. 104-111.
Russell, S. et al., "Efficacy and safety of voretigene neparvovec (AAV2-hRPE65v2) in patients with RPE65-mediated inherited retinal dystrophy: a randomised, controlled, open-label, phase 3 trial," The Lancet, vol. 390, Iss. 10097, Aug. 26, 2017, pp. 849-860.
Ryazantsev, S. et al., "Lysosomal accumulation of SCMAS (subunit c of mitochondrial ATP synthase) in neurons of the mouse model of mucopolysaccharidosis III B," Molecular Genetics and Metabolism, vol. 90, Iss. 4, Apr. 2007, pp. 393-401.
Salegio, E.A. et al., "Axonal transport of adeno-associated viral vectors is serotype-dependent," Gene Therapy, vol. 20, Mar. 15, 2012, pp. 348-352.
Schmidt et al. "Molecular Characterization of the Heparin-Dependent Transduction Domain on the Capsid of a Novel Adeno-Associated Virus Isolate, AAV(VR-942)", Journal of Virology, vol. 82, No. 17, Sep. 2008, pp. 8911-8916.
Schwartz, M.D. et al., "Projections of the suprachiasmatic nucleus and ventral subparaventricularzone in the Nile grass rat (*Arvicanthis niloticus*)," Brain Research, vol. 1367, Jan. 2011, pp. 146-161.
Sergijenko, A. et al., "Myeloid/microglial driven autologous hematopoietic stem cell gene therapy corrects a neuronopathic lysosomal disease," Molecular Therapy, vol. 21, Iss. 10, Oct. 2013, pp. 1938-1949.
Seyrantepe, V. et al., "Mice deficient in Neu4 sialidase exhibit abnormal ganglio side catabolism and lysosomal storage," Human Molecular Genetics, vol. 17, Iss. 11, Jun. 2008, pp. 1556-1568.
Shade, R.O. et al., "Nucleotide sequence and genome organization of human parvovirus B19 isolated from the serum of a child during aplastic crisis," Journal of Virology 58(3), May 31, 1986, pp. 921-936.
Shen, J. et al., "Suppression of ocular neovascularization with siRNA targeting VEGF receptor 1," Gene Therapy, vol. 13, Sep. 29, 2005, pp. 225-234.
Shen, S. et al., "Engraftment of a galactose receptor footprint onto adeno-associated viral capsids improves transduction efficiency," Journal of Biological Chemistry, vol. 288, Iss. 40, Oct. 4, 2013, pp. 28814-28823.
Shpaer, E.G., "GeneAssist," Methods in Molecular Biology, vol. 70, 1997, pp. 173-187.

(56) References Cited

OTHER PUBLICATIONS

Smith, T.F. et al., "Comparison of biosequences," Advances in Applied Mathematics, vol. 2, Iss 4, Dec. 1981, pp. 482-489.
Sondhi, D. et al., "Partial correction of the CNS lysosomal storage defect in a mouse model of juvenile neuronal ceroid lipofuscinosis by neonatal CNS administration of an adeno-associated virus serotype rh.10 vector expressing the human CLN3 gene," Human Gene Therapy, vol. 25, No. 3, Dec. 29, 2013, pp. 223-239.
Spark Therapeutics, "Spark Therapeutics Presents Updated Preliminary Data from Hemophilia B Phase 1/2 Trial Suggesting Consistent and Sustained Levels of Factor IX Activity at the Hemostasis and Thrombosis Research Society (HTRS) 2017 Scientific Symposium," Apr. 6, 2017, five pages, [Online] [Retrieved on Mar. 16, 2021] Retrieved from the Internet <URL: https://sparktx.com/press_releases/spark-therapeutics-presents-updated-preliminary-data-from-hemophilia-b-phase-1-2-trial-suggesting-consistent-and-sustained-levels-of-factor-ix-activity-at-the-hemostasis-and-thrombosis-research-societ/>.
Srivastava, A. et al., "Nucleotide sequence and organization of the adeno-associated virus 2 genome," Journal of Virology 45(2), 1983, pp. 555-564.
Summerford, C. et al., "Membrane-Associated Heparan Sulfate Proteoglycan Is a Receptor for Adeno-Associated Virus Type 2 Virions," Journal of Virology 72(2), Feb. 1998, pp. 1438-1445.
Supotnitskiy, M. V., "Genotherapeutic vector systems based on viruses," Biopreparats (Biopharmaceuticals), Aug. 25, 2011. pp. 15-26, (with English abstract).
Takamatsu, Y. et al., "Improvement of learning and increase in dopamine level in the frontal cortex by methylphenidate in mice lacking dopamine transporter," Current Molecular Medicine, vol. 15, No. 3, Nov. 3, 2015, pp. 245-252.
Tardieu, M. et al., "Intracerebral administration of adeno-associated Viral vector serotype rh.10 carrying human SGSH and SUMF1 cDNAs in children with mucopolysaccharidosis type IIIA disease: results of a phase I/II trial," Human Gene Therapy, vol. 25, No. 6, Feb. 13, 2014, pp. 506-516.
Tardieu, M. et al., "Intracerebral gene therapy in children with mucopolysaccharidosis type IIIB syndrome: an uncontrolled phase 1/2 clinical trial," The Lancet Neurology, vol. 16, Iss. 9, Jul. 13, 2017, pp. 712-720.
Tervo, D.G.R. et al., "A Designer AAV Variant Permits Efficient Retrograde Access to Projection Neurons," Neuron, vol. 92, Iss. 2, Oct. 19, 2016, pp. 372-382.
The Intellectual Property Office of the United Kingdom, Office Action, GB Patent Application No. 1403684.2, dated Nov. 26, 2014, pp. 1-5.
The Intellectual Property Office of the United Kingdom, Patent Application No. GB1403684.2, filed Mar. 3, 2014, pp. 1-73.
Tordo et al. "A Novel Adeno-Associated Virus Capsid with Enhanced Neurotropism Corrects A Lysosomal Transmembrane Enzyme Deficiency", Brain, 141(7), May 16, 2018, pp. 2014-2031.
Tseng, Y-S, et al. "Adeno-associated virus serotype 1 (AAV1)- and AAV5-anti body complex structures Reveal evolutionary commonalities in parvovirus antigenic reactivity," Journal of Virology 89(3), Nov. 18, 2014, pp. 1794-1808.
Valstar, M.J. et al., "Sanfilippo syndrome: A mini-review," Journal of Inherited Metabolic Disease, vol. 31, Apr. 4, 2008, pp. 240-252.
Vandenberghe, L.H. et al., "Novel adeno-associated viral vectors for retinal gene therapy," Gene Therapy, vol. 19, Oct. 13, 2011, pp. 162-168.
Wilkinson, F.L. et al., "Neuropathology in mouse models of mucopolysaccharidosis type I, IIIa and IIIB," PLoS One, vol. 7, Apr. 27, 2012, pp. 1-18.
Winner, L.K. et al., "A preclinical study evaluating AAVrh10-based gene therapy for Sanfilippo syndrome," Human Gene Therapy, vol. 27, No. 5, Mar. 14, 2016, pp. 363-375.
Woodard, K.T. et al., "Heparan sulfate binding promotes accumulation of intravitreally delivered adenoassociated viral vectors at the retina for enhanced transduction but weakly influences tropism," Journal of Virology, vol. 90, No. 21, Nov. 2016, pp. 9878-9888.
Worgall, S. et al., "Treatment of late infantile neuronal ceroid lipofuscinosis by CNS administration of a serotype 2 adeno-associated virus expressingCLN2 cDNA," Human Gene Therapy, vol. 19, No. 5, May 28, 2008, pp. 463-474.
Wu, P. et al., "Mutational analysis of the adeno-associated virus type 2 (AAV2) capsid gene and construction of AAV2 vectors with altered tropism," Journal of Virology, vol. 74, Sep. 2000, pp. 8635-8647.
Xiao, W. et al., "Gene therapy vectors based on adeno-associated virus type 1," Journal of Virology 73(5), May 1999, pp. 3994-4003.
Yokoyama, T. et al., "Photoreceptor-specific activity of the human interphotoreceptor retinoid-binding protein (IRBP) promoter in transgenic mice," Experimental Eye Research, vol. 55, Iss. 2, Aug. 1992, pp. 225-233.
Young, J.E. et al., "A Short, Highly Active Photoreceptor-Specific Enhancer/Promoter Region Upstream of the Human Rhodopsin Kinase Gene," Investigative Ophthalmology & Visual Science, vol. 44, Sep. 2003, pp. 4076-4085.
Zeltner, N. et al., "Near-perfect infectivity of wild-type AAV as benchmark for infectivity of recombinant AAV vectors," Gene Therapy, vol. 17, Mar. 25, 2010, pp. 872-879.
Zhang, X. et al., "Implications of heparan sulfate and heparanase in neuroinflammation," Matrix Biology, vol. 35, Apr. 2014, pp. 174-181.
Zinn, E. et al., "In silico reconstruction of the viral evolutionary lineage yields a potent gene therapy vector," Cell Reports, vol. 12, Iss. 6, Aug. 11, 2015, pp. 1056-1068.
Zolotukhin, S. et al., "Production and purification of serotype 1, 2, and 5 recombinant adeno-associated viral vectors," Methods 28(2), Oct. 2002, pp. 158-167.
Zolotukhin, S. et al., "Recombinant adeno-associated virus purification using novel methods improves infectious titer and yield," Gene Therapy, vol. 6, Jun. 25, 1999, pp. 973-985.
United States Office Action, U.S. Appl. No. 15/570,687, filed Jan. 7, 2021, 13 pages.
Alloca, M. et al, "Novel Adeno-Associated Virus Serotypes Efficiently Transduce Murine Photoreceptors", Journal of Virology 81(20): 11372-11380 (2007).
Arnett, Alh et al., "Heparin-binding correlates with increased efficiency of AAV1- and AAV6-mediated transduction of striated muscle, but negatively impacts CNS transduction", Gene Therapy 20:497-503 (2013).
Coune, P. et al., "Parkinson's Disease: Gene Therapies", Cold Spring Harb. Perspect. Med. 2(4):a009431, p. 1-9 (2012).
McLaughlin et al., "Adeno-Associated Virus General Transduction Vectors: Analysis of Proviral Structures", J. Virol. 62(6):1963-73 (1988).
Murlidharan, G. et al., "Biology of adeno-associated viral vectors in the central nervous system", Front. Mol. Neurosci. 7(76):1-9 (2014).
Purves D, Augustine C, Fitzpatrick D, et al., editors, "The Retina", Neuroscience. 2nd edition. Sunderland (MA): Sinauer Associates, Extract, 3 pages, (2001).
Samulski et al., "AAV-Mediated Gene Therapy for Research and Therapeutic Purposes", Annu. Rev. Virol. 1:427-51 (2014).
Samulski et al., "Helper-Free Stocks of Recombinant Adeno-Associated Viruses: Normal Integration Does Not Require Viral Gene Expression", J. Virol. 63(9):3822-28 (1989).
Sequence alignment of SEQ ID No. 1 and SEQ ID No. 2 of EP 3137497, cited in the Notice of Opposition of EP 3137497 dated Jan. 7, 2022.
Vandenberghe et al., "Heparin binding directs activation ofT cells against adeno-associated virus serotype 2 capsid", Nature Medicine 12(8):967-971 (2006).
Final Office Action, U.S. Appl. No. 15/570,687, filed Jun. 10, 2021, 10 pages.
Final Office Action, U.S. Appl. No. 15/570,687, filed May 12, 2020, 14 pages.
Non-Final Office Action, U.S. Appl. No. 15/570,687, filed Oct. 4, 2019,16 pages.
U.S. Appl. No. 61/988,131, filed May 2, 2014.
U.S. Appl. No. 62/114,575, filed Feb. 10, 2015.
Declaration of Ralph Michael Linden dated Oct. 17, 2020.

(56) References Cited

OTHER PUBLICATIONS

Non-Final Office Action, U.S. Appl. No. 17/466,237, filed Jul. 8, 2022, 37 pages.
Gao G. et al., "Clades of Adeno-Associated Viruses are Widely Disseminated in Human Tissues", Journal of Virology 78(12):6381-6388 (Jun. 1, 2004).
Schmidt, M., et al., "Molecular Characterization of the Heparin-Dependent Transduction Domain on the Capsid of a Novel Adena-Associated Virus Isolate, AAV(VR-942)", Journal of Virology, Sep. 2008, p. 8911-8916.
Bennett et al., "Comparative structural, biophysical, and receptor binding study of true type and wild type AAV2," J. Struct Biol. 213(4):107795 (2021).
Cui et al., "Proteoglycans in the Central Nervous System: Role in Development, Neural Repair, and Alzheimer's Disease," IUBMB Live 65(2):108-120 (2013).
Wu et al., "Adeno-associated Virus Serotypes: Vector Toolkit for Human Gene Therapy," Molecular Therapy 14(3):316-327, (2006).
Tordo et al., "A novel adeno-associated virus capsid with enhanced neurotropism corrects a lysosomal transmembrane enzyme deficiency," Brain 141:2014-2031 (2018).
Information Disclosure Statement By Applicant dated Oct. 27, 2020, 2 pages.

* cited by examiner

Figure 1 - SEQ ID NO:1
AAV2 - capsid protein VP1
ncbi NC_001401 - CDS "major coat protein VP1"
V125, V151, A162, T205, N312, Q457, S492, E499, F533, G546, E548, R585, R588 and A593

MAADGYLPDWLEDTLSEGIRQWWKLKPGPPPPKPAERHKDDSRGLVLPGYKYLGPFNGLDKGEPVNEAD
AAALEHDKAYDRQLDSGDNPYLKYNHADAEFQERLKEDTSFGGNLGRAVFQAKKRVLEPLGLVEEPVKT
APGKKRPVEHSPVEPDSSSGTGKAGQQPARKRLNFGQTGDADSVPDPQPLGQPPAAPSGLGTNTMATGS
GAPMADNNEGADGVGNSSGNWHCDSTWMGDRVITTSTRTWALPTYNNHLYKQISSQSGASNDNHYFGYS
TPWGYFDFNRFHCHFSPRDWQRLINNNWGFRPKRLNFKLFNIQVKEVTQNDGTTTIANNLTSTVQVFTD
SEYQLPYVLGSAHQGCLPPFPADVFMVPQYGYLTLNNGSQAVGRSSFYCLEYFPSQMLRTGNNFTFSYT
FEDVPFHSSYAHSQSLDRLMNPLIDQYLYYLSRTNTPSGTTTQSRLQFSQAGASDIRDQSRNWLPGPCY
RQQRVSKTSADNNNSEYSWTGATKYHLNGRDSLVNPGPAMASHKDDEEKFFPQSGVLIFGKQGSEKTNV
DIEKVMITDEEEIRTTNPVATEQYGSVSTNLQRGNRQAATADVNTQGVLPGMVWQDRDVYLQGPIWAKI
PHTDGHFHPSPLMGGFGLKHPPPQILIKNTPVPANPSTTFSAAKFASFITQYSTGQVSVEIEWELQKEN
SKRWNPEIQYTSNYNKSVNVDFTVDTNGVYSEPRPIGTRYLTRNL

Figure 2 - SEQ ID NO:2

AAV2 TRUE-TYPE - capsid VP1
I125, A151, S162, S205, S312, M457, A492, D499, Y533, D546, G548, S585, T588, S593

MAADGYLPDWLEDTLSEGIRQWWKLKPGPPPPKPAERHKDDSRGLVLPGYKYLGPFNGLDKGEPVNEAD
AAALEHDKAYDRQLDSGDNPYLKYNHADAEFQERLKEDTSFGGNLGRAVFQAKKRILEPLGLVEEPVKT
APGKKRPVEHSPAEPDSSSGTGKSGQQPARKRLNFGQTGDADSVPDPQPLGQPPAAPSGLGTNTMASGS
GAPMADNNEGADGVGNSSGNWHCDSTWMGDRVITTSTRTWALPTYNNHLYKQISSQSGASNDNHYFGYS
TPWGYFDFNRFHCHFSPRDWQRLINNNWGFRPKRLSFKLFNIQVKEVTQNDGTTTIANNLTSTVQVFTD
SEYQLPYVLGSAHQGCLPPFPADVFMVPQYGYLTLNNGSQAVGRSSFYCLEYFPSQMLRTGNNFTFSYT
FEDVPFHSSYAHSQSLDRLMNPLIDQYLYYLSRTNTPSGTTTMSRLQFSQAGASDIRDQSRNWLPGPCY
RQQRVSKTAADNNNSDYSWTGATKYHLNGRDSLVNPGPAMASHKDDEEKYFPQSGVLIFGKQDSGKTNV
DIEKVMITDEEEIRTTNPVATEQYGSVSTNLQSGNTQAATSDVNTQGVLPGMVWQDRDVYLQGPIWAKI
PHTDGHFHPSPLMGGFGLKHPPPQILIKNTPVPANPSTTFSAAKFASFITQYSTGQVSVEIEWELQKEN
SKRWNPEIQYTSNYNKSVNVDFTVDTNGVYSEPRPIGTRYLTRNL

Figure 3 - SEQ ID NO:3

AAV1 - capsid protein VP1
ncbi NC_002077 - CDS "AAV1gp2"
S205 *(aligns with S205 in ttAAV2)* - G549 *(aligns with G548 in ttAAV2)* - S586 *(aligns with S585 in ttAAV2)* - T589 *(aligns with T588 in ttAAV2)*

MAADGYLPDWLEDNLSEGIREWWDLKPGAPKPKANQQKQDDGRGLVLPGYKYLGPFNGLDKGEPVNAAD
AAALEHDKAYDQQLKAGDNPYLRYNHADAEFQERLQEDTSFGGNLGRAVFQAKKRVLEPLGLVEEGAKT
APGKKRPVEQSPQEPDSSSGIGKTGQQPAKKRLNFGQTGDSESVPDPQPLGEPPATPAAVGPTTMASGG
GAPMADNNEGADGVGNASGNWHCDSTWLGDRVITTSTRTWALPTYNNHLYKQISSASTGASNDNHYFGY
STPWGYFDFNRFHCHFSPRDWQRLINNNWGFRPKRLNFKLFNIQVKEVTTNDGVTTIANNLTSTVQVFS
DSEYQLPYVLGSAHQGCLPPFPADVFMIPQYGYLTLNNGSQAVGRSSFYCLEYFPSQMLRTGNNFTFSY
TFEEVPFHSSYAHSQSLDRLMNPLIDQYLYYLNRTQNQSGSAQNKDLLFSRGSPAGMSVQPKNWLPGPC
YRQQRVSKTKTDNNNSNFTWTGASKYNLNGRESIINPGTAMASHKDDEDKFFPMSGVMIFGKESAGASN
TALDNVMITDEEEIKATNPVATERFGTVAVNFQSSSTDPATGDVHAMGALPGMVWQDRDVYLQGPIWAK
IPHTDGHFHPSPLMGGFGLKNPPPQILIKNTPVPANPPAEFSATKFASFITQYSTGQVSVEIEWELQKE
NSKRWNPEVQYTSNYAKSANVDFTVDNNGLYTEPRPIGTRYLTRPL

Figure 4 - SEQ ID NO:4

AAV5 - capsid protein VP1
ncbi AF085716 - CDS "VP1"
*G537 (aligns with G548 in ttAAV2) - S575 (aligns with S585 in ttAAV2) - T578 (aligns with T588 in ttAAV2)*

MSFVDHPPDWLEEVGEGLREFLGLEAGPPKPKPNQQHQDQARGLVLPGYNYLGPGNGLDRGEPVNRADE
VAREHDISYNEQLEAGDNPYLKYNHADAEFQEKLADDTSFGGNLGKAVFQAKKRVLEPFGLVEEGAKTA
PTGKRIDDHFPKRKKARTEEDSKPSTSSDAEAGPSGSQQLQIPAQPASSLGADTMSAGGGGPLGDNNQG
ADGVGNASGDWHCDSTWMGDRVVTKSTRTWVLPSYNNHQYREIKSGSVDGSNANAYFGYSTPWGYFDFN
RFHSHWSPRDWQRLINNYWGFRPRSLRVKIFNIQVKEVTVQDSTTTIANNLTSTVQVFTDDDYQLPYVV
GNGTEGCLPAFPPQVFTLPQYGYATLNRDNTENPTERSSFFCLEYFPSKMLRTGNNFEFTYNFEEVPFH
SSFAPSQNLFKLANPLVDQYLYRFVSTNNTGGVQFNKNLAGRYANTYKNWFPGPMGRTQGWNLGSGVNR
ASVSAFATTNRMELEGASYQVPPQPNGMTNNLQGSNTYALENTMIFNSQPANPGTTATYLEGNMLITSE
SETQPVNRVAYNVGGQMATNNQSSTTAPATGTYNLQEIVPGSVWMERDVYLQGPIWAKIPETGAHFHPS
PAMGGFGLKHPPPMMLIKNTPVPGNITSFSDVPVSSFITQYSTGQVTVEMEWELKKENSKRWNPEIQYT
NNYNDPQFVDFAPDSTGEYRTTRPIGTRYLTRPL

Figure 5 - SEQ ID NO:5

AAV6 - capsid protein VP1
ncbi AF028704 - CDS "capsid protein VP1"
*S205 (aligns with S205 in ttAAV2) - G549 (aligns with G548 in ttAAV2) - S586 (aligns with S585 in ttAAV2) - T589 (aligns with T588 in ttAAV2)*

MAADGYLPDWLEDNLSEGIREWWDLKPGAPKPKANQQKQDDGRGLVLPGYKYLGPFNGLDKGEPVNAAD
AAALEHDKAYDQQLKAGDNPYLRYNHADAEFQERLQEDTSFGGNLGRAVFQAKKRVLEPFGLVEEGAKT
APGKKRPVEQSPQEPDSSSGIGKTGQQPAKKRLNFGQTGDSESVPDPQPLGEPPATPAAVGPTTMASGG
GAPMADNNEGADGVGNASGNWHCDSTWLGDRVITTSTRTWALPTYNNHLYKQISSASTGASNDNHYFGY
STPWGYFDFNRFHCHFSPRDWQRLINNNWGFRPKRLNFKLFNIQVKEVTTNDGVTTIANNLTSTVQVFS
DSEYQLPYVLGSAHQGCLPPFPADVFMIPQYGYLTLNNGSQAVGRSSFYCLEYFPSQMLRTGNNFTFSY
TFEDVPFHSSYAHSQSLDRLMNPLIDQYLYYLNRTQNQSGSAQNKDLLFSRGSPAGMSVQPKNWLPGPC
YRQQRVSKTKTDNNNSNFTWTGASKYNLNGRESIINPGTAMASHKDDKDKFFPMSGVMIFGKESAGASN
TALDNVMITDEEEIKATNPVATERFGTVAVNLQSSSTDPATGDVHVMGALPGMVWQDRDVYLQGPIWAK
IPHTDGHFHPSPLMGGFGLKHPPPQILIKNTPVPANPPAEFSATKFASFITQYSTGQVSVEIEWELQKE
NSKRWNPEVQYTSNYAKSANVDFTVDNNGLYTEPRPIGTRYLTRPL

Figure 6 - SEQ ID NO:6

AAV8 - capsid protein VP1
ncbi NC_006261 - CDS "AAV8_gp2"
*S315 (aligns with S312 in ttAAV2) - T591 (aligns with T588 in ttAAV2)*

MAADGYLPDWLEDNLSEGIREWWALKPGAPKPKANQQKQDDGRGLVLPGYKYLGPFNGLDKGEPVNAAD
AAALEHDKAYDQQLQAGDNPYLRYNHADAEFQERLQEDTSFGGNLGRAVFQAKKRVLEPLGLVEEGAKT
APGKKRPVEPSPQRSPDSSTGIGKKGQQPARKRLNFGQTGDSESVPDPQPLGEPPAAPSGVGPNTMAAG
GGAPMADNNEGADGVGSSSGNWHCDSTWLGDRVITTSTRTWALPTYNNHLYKQISNGTSGGATNDNTYF
GYSTPWGYFDFNRFHCHFSPRDWQRLINNNWGFRPKRLSFKLFNIQVKEVTQNEGTKTIANNLTSTIQV
FTDSEYQLPYVLGSAHQGCLPPFPADVFMIPQYGYLTLNNGSQAVGRSSFYCLEYFPSQMLRTGNNFQF
TYTFEDVPFHSSYAHSQSLDRLMNPLIDQYLYYLSRTQTTGGTANTQTLGFSQGGPNTMANQAKNWLPG
PCYRQQRVSTTTGQNNNSNFAWTAGTKYHLNGRNSLANPGIAMATHKDDEERFFPSNGILIFGKQNAAR
DNADYSDVMLTSEEEIKTTNPVATEEYGIVADNLQQQNTAPQIGTVNSQGALPGMVWQNRDVYLQGPIW
AKIPHTDGNFHPSPLMGGFGLKHPPPQILIKNTPVPADPPTTFNQSKLNSFITQYSTGQVSVEIEWELQ
KENSKRWNPEIQYTSNYYKSTSVDFAVNTEGVYSEPRPIGTRYLTRNL

Figure 7 - SEQ ID NO:7

AAV9 - capsid protein VP1
ncbi AY530579 - CDS "capsid protein VP1"
*S163 (aligns with S162 in ttAAV2) - S205 (aligns with S205 in ttAAV2) - G549 (aligns with G548 in ttAAV2)- S586 (aligns with S585 in ttAAV2)*

MAADGYLPDWLEDNLSEGIREWWALKPGAPQPKANQQHQDNARGLVLPGYKYLGPGNGLDKGEPVNAAD
AAALEHDKAYDQQLKAGDNPYLKYNHADAEFQERLKEDTSFGGNLGRAVFQAKKRLLEPLGLVEEAAKT
APGKKRPVEQSPQEPDSSAGIGKSGAQPAKKRLNFGQTGDTESVPDPQPIGEPPAAPSGVGSLTMASGG
GAPVADNNEGADGVGSSSGNWHCDSQWLGDRVITTSTRTWALPTYNNHLYKQISNSTSGGSSNDNAYFG
YSTPWGYFDFNRFHCHFSPRDWQRLINNNWGFRPKRLNFKLFNIQVKEVTDNNGVKTIANNLTSTVQVF
TDSDYQLPYVLGSAHEGCLPPFPADVFMIPQYGYLTLNDGSQAVGRSSFYCLEYFPSQMLRTGNNFQFS
YEFENVPFHSSYAHSQSLDRLMNPLIDQYLYYLSKTINGSGQNQQTLKFSVAGPSNMAVQGRNYIPGPS
YRQQRVSTTVTQNNNSEFAWPGASSWALNGRNSLMNPGPAMASHKEGEDRFFPLSGSLIFGKQGTGRDN
VDADKVMITNEEEIKTTNPVATESYGQVATNHQSAQAQAQTGWVQNQGILPGMVWQDRDVYLQGPIWAK
IPHTDGNFHPSPLMGGFGMKHPPPQILIKNTPVPADPPTAFNKDKLNSFITQYSTGQVSVEIEWELQKE
NSKRWNPEIQYTSNYYKSNNVEFAVNTEGVYSEPRPIGTRYLTRNL

Figure 8 - SEQ ID NO:8

AAV10 - capsid protein *Translation Upenn plasmid sequence*
*G551 (aligns with G548 in ttAAV2)*

MAADGYLPDWLEDNLSEGIREWWDLKPGAPKPKANQQKQDDGRGLVLPGYKYLGPFNGLDKGEPVNAAD
AAALEHDKAYDQQLKAGDNPYLRYNHADAEFQERLQEDTSFGGNLGRAVFQAKKRVLEPLGLVEEGAKT
APGKKRPVEPSPQRSPDSSTGIGKKGQQPAKKRLNFGQTGDSESVPDPQPIGEPPAGPSGLGSGTMAAG
GGAPMADNNEGADGVGSSSGNWHCDSTWLGDRVITTSTRTWALPTYNNHLYKQISNGTSGGSTNDNTYF
GYSTPWGYFDFNRFHCHFSPRDWQRLINNNWGFRPKRLNFKLFNIQVKEVTQNEGTKTIANNLTSTIQV
FTDSEYQLPYVLGSAHQGCLPPFPADVFMIPQYGYLTLNNGSQAVGRSSFYCLEYFPSQMLRTGNNFEF
SYQFEDVPFHSSYAHSQSLDRLMNPLIDQYLYYLSRTQSTGGTAGTQQLLFSQAGPNNMSAQAKNWLPG
PCYRQQRVSTTLSQNNNSNFAWTGATKYHLNGRDSLVNPGVAMATHKDDEERFFPSSGVLMFGKQGAGK
DNVDYSSVMLTSEEEIKTTNPVATEQYGVVADNLQQQNAAPIVGAVNSQGALPGMVWQNRDVYLQGPIW
AKIPHTDGNFHPSPLMGGFGLKHPPPQILIKNTPVPADPPTTFSQAKLASFITQYSTGQVSVEIEWELQ
KENSKRWNPEIQYTSNYYKSTNVDFAVNTDGTYSEPRPIGTRYLTRNL

AAVs VP1 proteins alignment

B

| | Vector genome (vg/ml) | Capsid titre ([illegible]) |
|---|---|---|
| AAV2-CMV-GFP TT concentrated | [illegible] | [illegible] |
| AAV2-CMV-GFP WT concentrated | [illegible] | [illegible] |

Figure 12
A
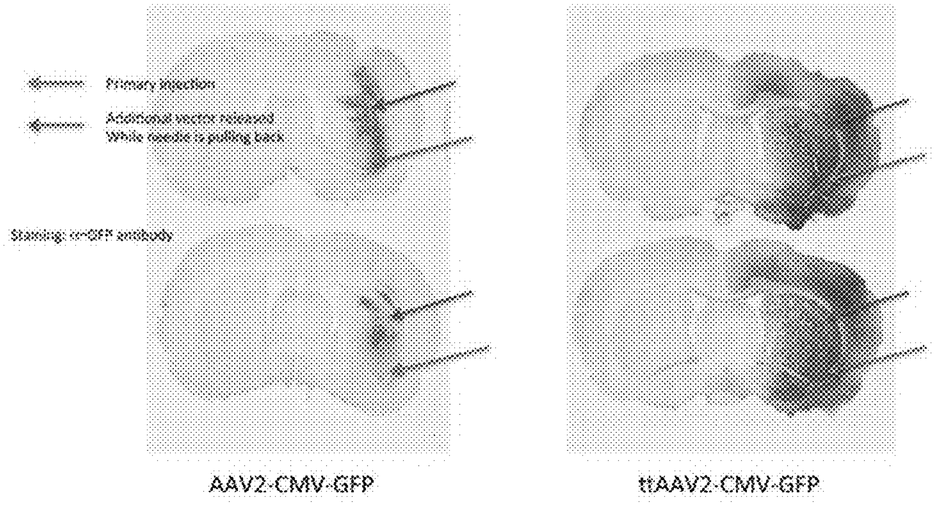
AAV2-CMV-GFP ttAAV2-CMV-GFP
B
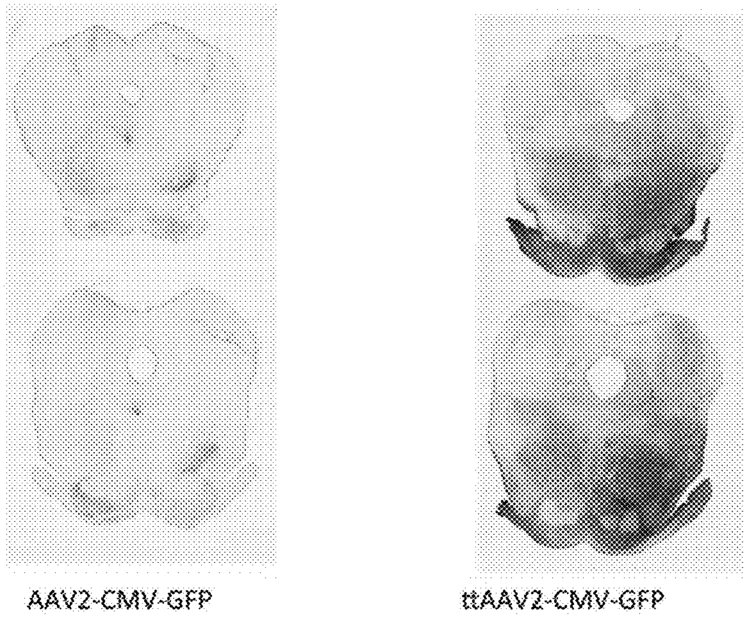
AAV2-CMV-GFP ttAAV2-CMV-GFP Figure 13
A
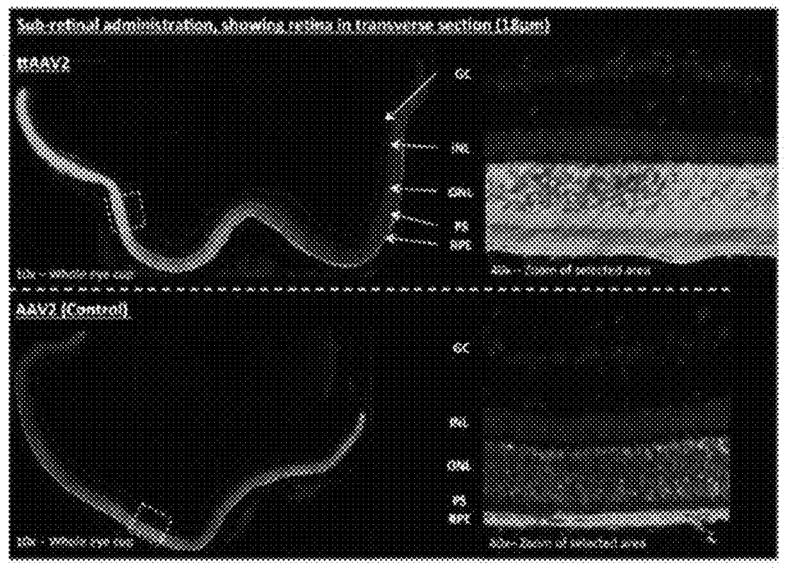
B
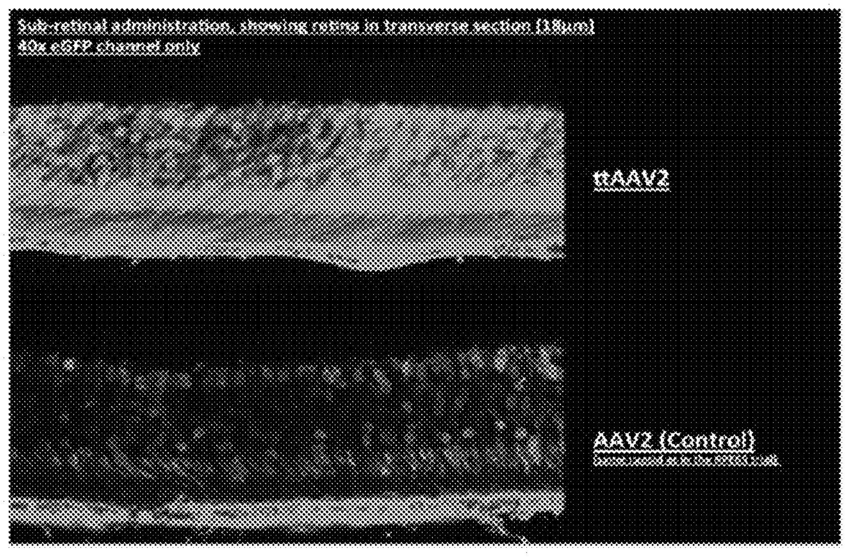

ttAAV2 vs AAV2 in neonates (mice; littermates; animals 4 and 16 died)

Figure 38

A eno-associate virus 3B (AAV3B) - capsi protein VP1 (SEQ ID NO:11)

ncbi AF028705 - capsid prot in 1
I125, S162, S205, S312, A493, S585 an R588

MAADGYLPDWLEDNLSEGIREWWALKPGVPQPKANQQHQDNRRGLVLPGYKYLGPGNGLDKGEPVNEAD
AAALEHDKAYDQQLKAGDNPYLKYNHADAEFQERLQEDTSFGGNLGRAVFQAKKRILEPLGLVEEAAKT
APGKKRPVDQSPQEPDSSSGVGKSGKQPARKRLNFGQTGDSESVPDPQPLGEPPAAPTSLGSNTMASGG
GAPMADNNEGADGVGNSSGNWHCDSQWLGDRVITTSTRTWALPTYNNHLYKQISSQSGASNDNHYFGYS
TPWGYFDFNRFHCHFSPRDWQRLINNNWGFRPKKLSFKLFNIQVKEVTQNDGTTTIANNLTSTVQVFTD
SEYQLPYVLGSAHQGCLPPFPADVFMVPQYGYLTLNNGSQAVGRSSFYCLEYFPSQMLRTGNNFQFSYT
FEDVPFHSSYAHSQSLDRLMNPLIDQYLYYLNRTQGTTSGTTNQSRLLFSQAGPQSMSLQARNWLPGPC
YRQQRLSKTANDNNNSNFPWTAASKYHLNGRDSLVNPGPAMASHKDDEEKFFPMHGNLIFGKEGTTASN
AELDNVMITDEEEIRTTNPVATEQYGTVANNLQSSNTAPTTRTVNDQGALPGMVWQDRDVYLQGPIWAK
IPHTDGHFHPSPLMGGFGLKHPPPQIMIKNTPVPANPPTTFSPAKFASFITQYSTGQVSVEIEWELQKE
NSKRWNPEIQYTSNYNKSVNVDFTVDTNGVYSEPRPIGTRYLTRNL

Figure 39

A eno-associate virus LK03 (AAV-LK03) - capsi protein VP1 (SEQ ID NO:12)

```
 et Ala Ala Asp Gly Tyr Leu Pro Asp Trp Leu Glu Asp Asn Leu Ser
                5                   0                   5
Glu Gly Ile Arg Glu Trp Trp Ala Leu Gln Pro Gly Ala Pro Lys Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            00                  05                  0
Asn Leu Gly Arg Ala Val Phe Gln Ala Lys Lys Arg Leu Leu Glu Pro
        5                   20                  25
Leu Gly Leu Val Glu Glu Ala Ala Lys Thr Ala Pro Gly Lys Lys Arg
    30                  35                  40
Pro Val Asp Gln Ser Pro Gln Glu Pro Asp Ser Ser Ser Gly Val Gly
45                  50                  55                  60
Lys Ser Gly Lys Gln Pro Ala Arg Lys Arg Leu Asn Phe Gly Gln Thr
                65                  70                  75
Gly Asp Ser Glu Ser Val Pro Asp Pro Gln Pro Leu Gly Glu Pro Pro
            80                  85                  90
Ala Ala Pro Thr Ser Leu Gly Ser Asn Thr  et Ala Ser Gly Gly Gly
        95                  200                 205
Ala Pro  et Ala Asp Asn Asn Glu Gly Ala Asp Gly Val Gly Asn Ser
    2 0                 2 5                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Lys Leu Ser Phe Lys Leu Phe Asn Ile Gln Val
305                 3 0                 3 5                 320
```

Figure 39 (cont.)

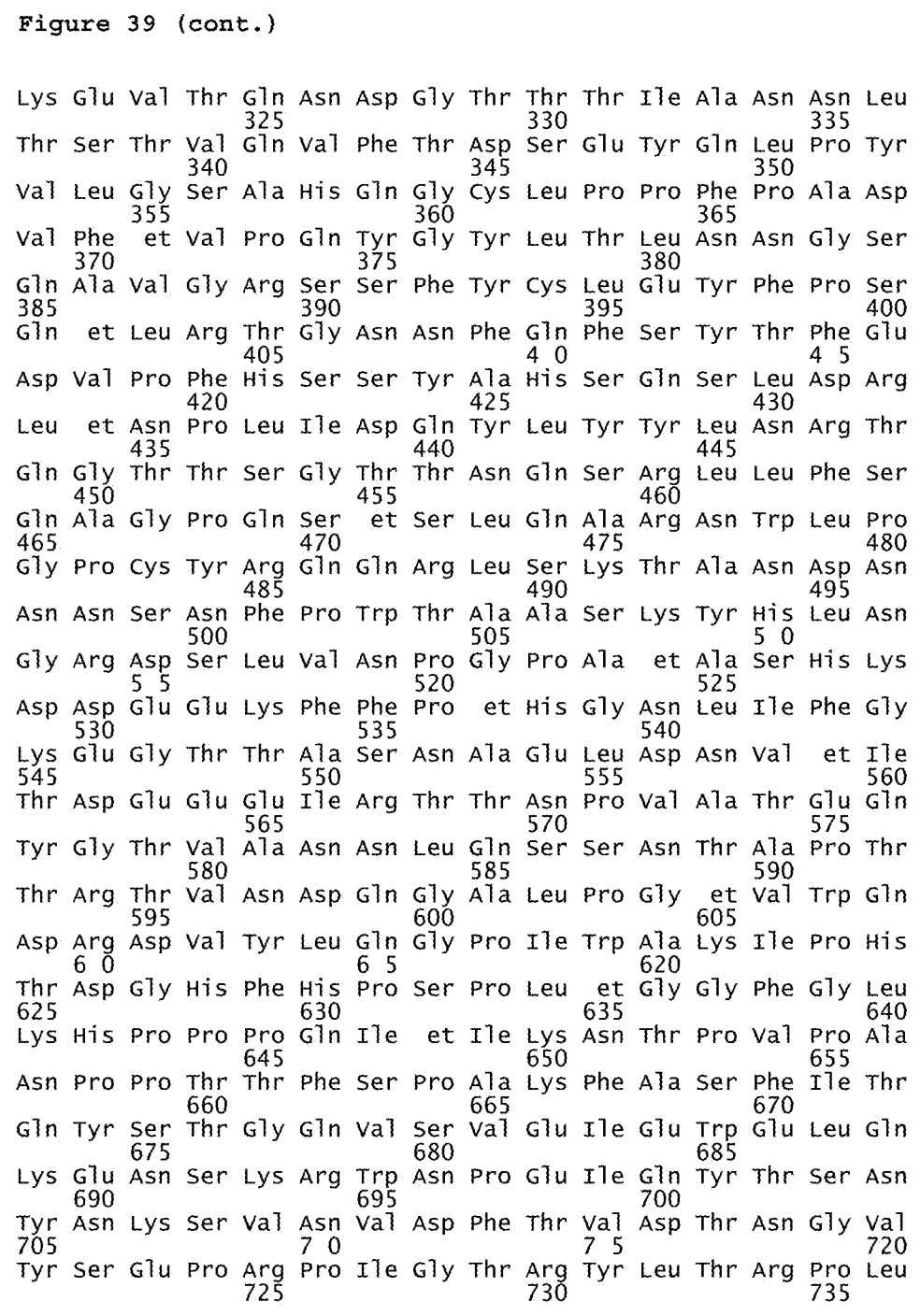

Lys Glu Val Thr Gln Asn Asp Gly Thr Thr Thr Ile Ala Asn Asn Leu
325 330 335
Thr Ser Thr Val Gln Val Phe Thr Asp Ser Glu Tyr Gln Leu Pro Tyr
340 345 350
Val Leu Gly Ser Ala His Gln Gly Cys Leu Pro Pro Phe Pro Ala Asp
355 360 365
Val Phe et Val Pro Gln Tyr Gly Tyr Leu Thr Leu Asn Asn Gly Ser
370 375 380
Gln Ala Val Gly Arg Ser Ser Phe Tyr Cys Leu Glu Tyr Phe Pro Ser
385 390 395 400
Gln et Leu Arg Thr Gly Asn Asn Phe Gln Phe Ser Tyr Thr Phe Glu
405 4 0 4 5
Asp Val Pro Phe His Ser Ser Tyr Ala His Ser Gln Ser Leu Asp Arg
420 425 430
Leu et Asn Pro Leu Ile Asp Gln Tyr Leu Tyr Tyr Leu Asn Arg Thr
435 440 445
Gln Gly Thr Thr Ser Gly Thr Thr Asn Gln Ser Arg Leu Leu Phe Ser
450 455 460
Gln Ala Gly Pro Gln Ser et Ser Leu Gln Ala Arg Asn Trp Leu Pro
465 470 475 480
Gly Pro Cys Tyr Arg Gln Gln Arg Leu Ser Lys Thr Ala Asn Asp Asn
485 490 495
Asn Asn Ser Asn Phe Pro Trp Thr Ala Ala Ser Lys Tyr His Leu Asn
500 505 5 0
Gly Arg Asp Ser Leu Val Asn Pro Gly Pro Ala et Ala Ser His Lys
5 5 520 525
Asp Asp Glu Glu Lys Phe Phe Pro et His Gly Asn Leu Ile Phe Gly
530 535 540
Lys Glu Gly Thr Thr Ala Ser Asn Ala Glu Leu Asp Asn Val et Ile
545 550 555 560
Thr Asp Glu Glu Glu Ile Arg Thr Thr Asn Pro Val Ala Thr Glu Gln
565 570 575
Tyr Gly Thr Val Ala Asn Asn Leu Gln Ser Ser Asn Thr Ala Pro Thr
580 585 590
Thr Arg Thr Val Asn Asp Gln Gly Ala Leu Pro Gly et Val Trp Gln
595 600 605
Asp Arg Asp Val Tyr Leu Gln Gly Pro Ile Trp Ala Lys Ile Pro His
6 0 6 5 620
Thr Asp Gly His Phe His Pro Ser Pro Leu et Gly Gly Phe Gly Leu
625 630 635 640
Lys His Pro Pro Pro Gln Ile et Ile Lys Asn Thr Pro Val Pro Ala
645 650 655
Asn Pro Pro Thr Thr Phe Ser Pro Ala Lys Phe Ala Ser Phe Ile Thr
660 665 670
Gln Tyr Ser Thr Gly Gln Val Ser Val Glu Ile Glu Trp Glu Leu Gln
675 680 685
Lys Glu Asn Ser Lys Arg Trp Asn Pro Glu Ile Gln Tyr Thr Ser Asn
690 695 700
Tyr Asn Lys Ser Val Asn Val Asp Phe Thr Val Asp Thr Asn Gly Val
705 7 0 7 5 720
Tyr Ser Glu Pro Arg Pro Ile Gly Thr Arg Tyr Leu Thr Arg Pro Leu
725 730 735

ADENO-ASSOCIATED VIRUS VECTOR

CROSS REFERENCE TO RELATED APPLICATION

This application is a continuation of U.S. patent application Ser. No. 15/570,687, filed Oct. 30, 2017, which is a 371 of International Application No. PCT/EP2015/053335 filed on Feb. 17, 2015, which claims the benefit of U.S. Provisional Application No. 61/940,639 filed on Feb. 17, 2014, and claims the right of priority from Great Britain Application No. GB 1403684.2, filed Mar. 2, 2014, the entire content and disclosure of which is incorporated herein by reference.

INCORPORATION BY REFERENCE OF SEQUENCE LISTING

The Sequence Listing in an ASCII text file, named as 36210Z_SequenceListing.txt of 77 KB, created on Oct. 16, 2020, and submitted to the United States Patent and Trademark Office via EFS-Web, is incorporated herein by reference.

FIELD OF THE INVENTION

The present invention relates to the field of recombinant viral vectors. In particular, the invention relates to recombinant viral vectors which are suitable for the delivery of therapeutic genes in vivo.

BACKGROUND TO THE INVENTION

To date, adeno-associated virus remains one of the most promising vectors for the delivery of therapeutic genes. A significant number of preclinical and clinical studies have firmly established that this approach is suitable for the development of gene-based drugs that can reach market approval.

Since the beginning of the development of AAV2 as a vector for gene therapy in the 1980s much progress has been made in optimizing this platform for a variety of applications and target tissues. Among those developments, possibly the most consequential has been the discovery of a wide variety of serotypes of which ten to twelve are now commonly explored. Among the most prominent characteristics of these various serotypes are their respective relative tissue tropism and—in some cases—the ability of neuronal retrograde transport. Of these serotypes, AAV1-10 are broadly used for pre-clinical and clinical purposes.

A newer platform has been developed that involves processes that allow for the targeting and de-targeting of specific tissues and cell sub-types in patients. The core technology of these approaches is based on trial and error evaluation of existing AAV variants (serotypes) and in vivo selection of randomly introduced AAV capsid mutants. Together, these two promising approaches provide tens—if not hundreds of potential vectors with different transduction behaviour.

The most intriguing aspect of AAV serotypes is their ability to efficiently transduce specific tissues in animal models and in man. To date, comprehensive molecular understanding of the underlying mechanisms for the tissue tropism has yet to be put forward and it is thus generally assumed that the available tissue-specific receptors for each serotype play a central role in the efficient transduction by the various serotypes.

Accordingly there is still a need for additional AAV vectors, which have improved properties in terms of in vivo transgene expression and tissue specificity. In particular, such vectors have the potential to provide greatly enhanced benefits for gene delivery to various target tissues in humans.

SUMMARY OF THE INVENTION

In one aspect, the present invention provides a recombinant adeno-associated virus (AAV) vector comprising: (a) a variant AAV2 capsid protein, wherein the variant AAV2 capsid protein comprises at least four amino acid substitutions with respect to a wild type AAV2 capsid protein; wherein the at least four amino acid substitutions are present at the following positions in an AAV2 capsid protein sequence: 457, 492, 499 and 533; and (b) a heterologous nucleic acid comprising a nucleotide sequence encoding a gene product.

In one embodiment, the variant AAV capsid protein comprises a sequence of SEQ ID NO:2, or a sequence having at least 95% sequence identity thereto. In another embodiment, the wild type AAV capsid protein comprises a sequence of SEQ ID NO:1.

In one embodiment, the variant AAV2 capsid protein comprises one or more of the following residues: M457, A492, D499 and Y533. In a preferred embodiment, the variant AAV2 capsid protein comprises one or more of the following amino acid substitutions with respect to a wild type AAV2 capsid protein: Q457M, S492A, E499D and F533Y.

In one embodiment, the variant AAV2 capsid protein further comprises one or more amino acid substitutions with respect to the wild type AAV capsid protein at the following positions in the AAV2 capsid protein sequence: 125, 151, 162 and 205. In a preferred embodiment, the variant AAV2 capsid protein comprises one or more of one or more of the following residues: I125, A151, 5162 and 5205. In another preferred embodiment, the variant AAV2 capsid protein comprises one or more of the following amino acid substitutions with respect to a wild type AAV2 capsid protein: V125I, V151A, A162S and T205S.

In one embodiment, the variant AAV2 capsid protein further comprises one or more amino acid substitutions with respect to the wild type AAV capsid protein at the following positions in the AAV2 capsid protein sequence: 585 and 588. Preferably the variant AAV2 capsid protein comprises one or more of one or more of the following residues: 5585 and T588. More preferably the variant AAV2 capsid protein comprises one or more of the following amino acid substitutions with respect to a wild type AAV2 capsid protein: R585S and R588T.

In one embodiment, the variant AAV2 capsid protein further comprises one or more amino acid substitutions with respect to the wild type AAV capsid protein at the following positions in the AAV2 capsid protein sequence: 546, 548 and 593. Preferably the variant AAV2 capsid protein comprises one or more of one or more of the following residues: D546, G548, and S593. More preferably the variant AAV2 capsid protein comprises one or more of the following amino acid substitutions with respect to a wild type AAV2 capsid protein: G546D, E548G and A593S.

In one embodiment, the variant AAV2 capsid protein comprises the residue N312, i.e. the residue which is present in the wild type AAV2 capsid protein at position 312. In this embodiment, the variant AAV2 capsid protein is not mutated at position 312 compared to the wild type AAV2 capsid protein sequence.

In another aspect, the present invention provides a recombinant adeno-associated virus (AAV) vector comprising: (a) a variant AAV8 capsid protein, wherein the variant AAV8 capsid protein comprises an amino acid substitution with respect to a wild type AAV8 capsid protein at position 315 in an AAV8 capsid protein sequence; and (b) a heterologous nucleic acid comprising a nucleotide sequence encoding a gene product.

In one embodiment, the variant AAV capsid protein comprises a sequence having at least 95% sequence identity to SEQ ID NO:6. In another embodiment, the wild type AAV capsid protein comprises a sequence of SEQ ID NO:6.

In one embodiment, the variant AAV8 capsid protein comprises the amino acid substitution S315N with respect to a wild type AAV8 capsid protein. Preferably the AAV8 capsid protein sequence comprises one or more amino acid substitution present at one or more of the following positions: 125, 151, 163, 206, 460, 495, 502, 536, 549, 551, 588, 591 and/or 596.

In a preferred embodiment, the variant AAV8 capsid protein comprises one or more of the following amino acid substitutions with respect to a wild type AAV8 capsid protein: (a) V125I, Q151A, K163S, A206S, T460M, T495A, N502D, F536Y, N549D, A551G, Q588S and/or G596S; and/or (b) T591R.

In another aspect, the present invention provides a recombinant adeno-associated virus (AAV) vector comprising: (a) a variant AAV3B capsid protein, wherein the variant AAV3B capsid protein comprises an amino acid substitution with respect to a wild type AAV3B capsid protein at position 312 in an AAV3B capsid protein sequence; and (b) a heterologous nucleic acid comprising a nucleotide sequence encoding a gene product.

In one embodiment, the variant AAV3B capsid protein comprises a sequence having at least 95% sequence identity to SEQ ID NO:11. In another embodiment, the wild type AAV capsid protein comprises a sequence of SEQ ID NO:11.

In one embodiment, the variant AAV3B capsid protein comprises the amino acid substitution S312N with respect to a wild type AAV3B capsid protein.

In another aspect, the present invention provides a recombinant adeno-associated virus (AAV) vector comprising (a) a variant AAV-LK03 capsid protein, wherein the variant AAV-LK03 capsid protein comprises an amino acid substitution at position 312 with respect to a AAV-LK03 capsid protein sequence as defined in SEQ ID NO:12; and (b) a heterologous nucleic acid comprising a nucleotide sequence encoding a gene product.

In one embodiment, the variant AAV-LK03 capsid protein comprises a sequence having at least 95% sequence identity to SEQ ID NO:12.

In another aspect, the present invention provides a recombinant adeno-associated virus (AAV) vector comprising: (a) a variant AAV capsid protein, wherein the variant AAV capsid protein comprises at least one amino acid substitution with respect to a wild type AAV capsid protein at a position corresponding to one or more of the following positions in an AAV2 capsid protein sequence: 125, 151, 162, 205, 312, 457, 492, 499, 533, 546, 548, 585, 588 and/or 593; and (b) a heterologous nucleic acid comprising a nucleotide sequence encoding a gene product.

In one embodiment, the at least one amino acid substitution is present at one or more of the following positions in an AAV2 capsid protein sequence: 125, 151, 162, 205, 312, 457, 492, 499, 533, 546, 548, 585, 588 and/or 593; or at one or more corresponding positions in an alternative AAV capsid protein sequence.

In one embodiment, the vector comprises a variant AAV2 capsid protein. In another embodiment, the variant AAV capsid protein comprises a sequence of SEQ ID NO:2, or a sequence having at least 95% sequence identity thereto. In another embodiment, the wild type AAV capsid protein is from AAV2. In another embodiment, the wild type AAV capsid protein comprises a sequence of SEQ ID NO:1.

In one embodiment, the variant AAV2 capsid protein comprises one or more of the following residues: I125, A151, S162, S205, S312, M457, A492, D499, Y533, D546, G548, S585, T588 and/or S593. In a preferred embodiment, the variant AAV2 capsid protein comprises one or more of the following amino acid substitutions with respect to a wild type AAV2 capsid protein: V125I, V151A, A162S, T205S, N312S, Q457M, S492A, E499D, F533Y, G546D, E548G, R585S, R588T and/or A593S.

In further embodiments, the variant AAV capsid protein is from AAV1, AAV5, AAV6, AAV8, AAV9 or AAV10.

In one embodiment, the vector comprises a variant AAV1 capsid protein. In another embodiment, the variant AAV capsid protein comprises a sequence having at least 95% sequence identity to SEQ ID NO:3. In another embodiment, the wild type AAV capsid protein is from AAV1. In another embodiment, the wild type AAV capsid protein comprises a sequence of SEQ ID NO:3.

In one embodiment, at least one amino acid substitution is present at one or more of the following positions in the AAV1 capsid protein sequence: 125, 151, 162, 205, 313, 458, 493, 500, 534, 547, 549, 586, 589 and/or 594. In a preferred embodiment, the variant AAV1 capsid protein comprises one or more of the following amino acid substitutions with respect to a wild type AAV1 capsid protein: V125I, Q151A, T162S, N313S, N458M, K493A, N500D, F534Y, S547D, and/or G594S. In an alternative embodiment, the variant AAV1 capsid protein comprises one or more of the following amino acid substitutions with respect to a wild type AAV1 capsid protein: S205T, G549E, S586R and/or T589R.

In one embodiment, the vector comprises a variant AAV5 capsid protein. In another embodiment, the variant AAV capsid protein comprises a sequence having at least 95% sequence identity to SEQ ID NO:4. In another embodiment, the wild type AAV capsid protein is from AAV5. In another embodiment, the wild type AAV capsid protein comprises a sequence of SEQ ID NO:4.

In one embodiment, at least one amino acid substitution is present at one or more of the following positions in the AAV5 capsid protein sequence: 124, 150, 153, 195, 303, 444, 479, 486, 520, 533, 537, 575, 578 and/or 583. In a preferred embodiment, the variant AAV5 capsid protein comprises one or more of the following amino acid substitutions with respect to a wild type AAV5 capsid protein: V124I, K150A, K153S, A195S, R303S, T444M, S479A, V486D, T520Y, P533D, and/or G583S. In an alternative embodiment, the variant AAV5 capsid protein comprises one or more of the following amino acid substitutions with respect to a wild type AAV5 capsid protein: G537E, S575R and/or T578R.

In one embodiment, the vector comprises a variant AAV6 capsid protein. In another embodiment, the variant AAV capsid protein comprises a sequence having at least 95% sequence identity to SEQ ID NO:5. In another embodiment, the wild type AAV capsid protein is from AAV6. In another embodiment, the wild type AAV capsid protein comprises a sequence of SEQ ID NO:5.

In one embodiment, at least one amino acid substitution is present at one or more of the following positions in the AAV6 capsid protein sequence: 125, 151, 162, 205, 313, 458, 493, 500, 534, 547, 549, 586, 589 and/or 594. In a preferred embodiment, the variant AAV6 capsid protein comprises one or more of the following amino acid substitutions with respect to a wild type AAV6 capsid protein: V125I, Q151A, T162S, N313S, N458M, K493A, N500D, F534Y, S547D, and/or G594S. In an alternative embodiment, the variant AAV6 capsid protein comprises one or more of the following amino acid substitutions with respect to a wild type AAV6 capsid protein: S205T, G549E, S586R and/or T589R.

In one embodiment, the vector comprises a variant AAV8 capsid protein. In another embodiment, the variant AAV capsid protein comprises a sequence having at least 95% sequence identity to SEQ ID NO:6. In another embodiment, the wild type AAV capsid protein is from AAV8. In another embodiment, the wild type AAV capsid protein comprises a sequence of SEQ ID NO:6.

In one embodiment, at least one amino acid substitution is present at one or more of the following positions in the AAV8 capsid protein sequence: 125, 151, 163, 206, 315, 460, 495, 502, 536, 549, 551, 588, 591 and/or 596. In a preferred embodiment, the variant AAV8 capsid protein comprises one or more of the following amino acid substitutions with respect to a wild type AAV8 capsid protein: V125I, Q151A, K163S, A206S, T460M, T495A, N502D, F536Y, N549D, A551G, Q588S and/or G596S. In an alternative embodiment, the variant AAV8 capsid protein comprises one or more of the following amino acid substitutions with respect to a wild type AAV8 capsid protein: S315N and/or T591R.

In one embodiment, the vector comprises a variant AAV9 capsid protein. In another embodiment, the variant AAV capsid protein comprises a sequence having at least 95% sequence identity to SEQ ID NO:7. In another embodiment, the wild type AAV capsid protein is from AAV9. In another embodiment, the wild type AAV capsid protein comprises a sequence of SEQ ID NO:7.

In one embodiment, at least one amino acid substitution is present at one or more of the following positions in the AAV9 capsid protein sequence: 125, 151, 162, 205, 314, 458, 493, 500, 534, 547, 549, 586, 589 and/or 594. In a preferred embodiment, the variant AAV9 capsid protein comprises one or more of the following amino acid substitutions with respect to a wild type AAV9 capsid protein: L125I, Q151A, N314S, Q458M, V493A, E500D, F534Y, G547D, A589T and/or G594S. In an alternative embodiment, the variant AAV9 capsid protein comprises one or more of the following amino acid substitutions with respect to a wild type AAV9 capsid protein: S162A, S205T, G549E and/or S586R.

In one embodiment, the vector comprises a variant AAV10 capsid protein. In another embodiment, the variant AAV capsid protein comprises a sequence having at least 95% sequence identity to SEQ ID NO:8. In another embodiment, the wild type AAV capsid protein is from AAV10. In another embodiment, the wild type AAV capsid protein comprises a sequence of SEQ ID NO:8.

In one embodiment, at least one amino acid substitution is present at one or more of the following positions in the AAV10 capsid protein sequence: 125, 151, 163, 206, 315, 460, 495, 502, 536, 549, 551, 588, 591 and/or 596. In a preferred embodiment, the variant AAV10 capsid protein comprises one or more of the following amino acid substitutions with respect to a wild type AAV10 capsid protein: V125I, Q151A, K163S, A206S, N315S, T460M, L495A, N502D, F536Y, G549D, Q588S, A591T and/or G596S. In an alternative embodiment, the variant AAV10 capsid protein comprises the following amino acid substitution with respect to a wild type AAV10 capsid protein: G551E.

In one embodiment, the recombinant AAV vector exhibits increased transduction of a neuronal or retinal tissue compared to an AAV vector comprising a corresponding wild type AAV capsid protein.

In another embodiment, the recombinant AAV vector exhibits increased transduction of liver tissue compared to a corresponding wild type AAV capsid protein.

In one embodiment, the gene product comprises an interfering RNA or an aptamer. In another embodiment, the gene product comprises a polypeptide. Preferably the gene product comprises a neuroprotective polypeptide, an anti-angiogenic polypeptide, or a polypeptide that enhances function of a neuronal or retinal cell. In preferred embodiments, the gene product comprises glial derived neurotrophic factor, fibroblast growth factor, nerve growth factor, brain derived neurotrophic factor, rhodopsin, retinoschisin, RPE65 or peripherin.

In another aspect, the present invention provides a pharmaceutical composition comprising: (a) a recombinant AAV vector as defined above; and (b) a pharmaceutically acceptable excipient.

In another aspect, the present invention provides a method for delivering a gene product to a tissue in a subject, the method comprising administering to the subject a recombinant AAV vector or pharmaceutical composition as defined above.

In some embodiments, the tissue is selected from blood, bone marrow, muscle tissue, neuronal tissue, retinal tissue, pancreatic tissue, liver tissue, kidney tissue, lung tissue, intestinal tissue or heart tissue. Preferably the tissue is neuronal, retinal or liver tissue.

In another aspect, the present invention provides a method for treating a disorder in a subject, the method comprising administering to the subject a recombinant AAV vector or pharmaceutical composition as defined above. In some embodiments, the disorder is a neurological, ocular or hepatic disorder.

In another aspect, the present invention provides a recombinant AAV vector or pharmaceutical composition as defined above, for use in treating a disorder in a subject. In some embodiments, the disorder is a neurological, ocular or hepatic disorder. Preferably the neurological disorder is a neurodegenerative disease. In an alternative embodiment, the ocular disorder is glaucoma, retinitis pigmentosa, macular degeneration, retinoschisis or diabetic retinopathy.

In another aspect, the present invention provides an isolated variant AAV capsid protein, wherein the variant AAV capsid protein comprises at least one amino acid substitution with respect to a wild type AAV capsid protein; wherein the at least one amino acid substitution is present at one or more of the following positions in an AAV2 capsid protein sequence: 125, 151, 162, 205, 312, 457, 492, 499, 533, 546, 548, 585, 588 and/or 593; or at one or more corresponding positions in an alternative AAV capsid protein sequence.

In another aspect, the present invention provides an isolated nucleic acid comprising a nucleotide sequence that encodes a variant AAV capsid protein as defined above.

In another aspect, the present invention provides an isolated host cell comprising a nucleic acid as defined above.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

FIG. 1 shows the amino acid sequence of wild-type adeno-associated virus 2 capsid protein VP1 (SEQ ID NO:1; NCBI Reference Sequence: NC_001401). Residues V125, V151, A162, T205, N312, Q457, 5492, E499, F533, G546, E548, R585, R588 and A593 are highlighted.

FIG. 2 shows the amino acid sequence of true-type adeno-associated virus 2 (ttAAV2) capsid protein VP1 (SEQ ID NO:2). Residues 1125, A151, S162, S205, S312, M457, A492, D499, Y533, D546, G548, S585, T588, 5593 differ compared to wild-type AAV2 VP1 (SEQ ID NO:1) and are highlighted.

FIG. 3 shows the amino acid sequence of wild-type adeno-associated virus 1 capsid protein VP1 (SEQ ID NO:3; NCBI Reference Sequence: NC_002077). Highlighted residues: S205 (aligns with S205 in ttAAV2 (SEQ ID NO:2))—G549 (aligns with G548 in ttAAV2)—S586 (aligns with S585 in ttAAV2)—T589 (aligns with T588 in ttAAV2).

FIG. 4 shows the amino acid sequence of wild-type adeno-associated virus 5 capsid protein VP1 (SEQ ID NO:4; NCBI Reference Sequence: AF085716). Highlighted residues: G537 (aligns with G548 in ttAAV2)—S575 (aligns with S585 in ttAAV2)—T578 (aligns with T588 in ttAAV2).

FIG. 5 shows the amino acid sequence of wild-type adeno-associated virus 6 capsid protein VP1 (SEQ ID NO:5; NCBI Reference Sequence: AF028704). Highlighted residues: S205 (aligns with S205 in ttAAV2)—G549 (aligns with G548 in ttAAV2)—S586 (aligns with S585 in ttAAV2)—T589 (aligns with T588 in ttAAV2).

FIG. 6 shows the amino acid sequence of wild-type adeno-associated virus 8 capsid protein VP1 (SEQ ID NO:6; NCBI Reference Sequence: NC_006261). Highlighted residues: S315 (aligns with S312 in ttAAV2)—T591 (aligns with T588 in ttAAV2).

FIG. 7 shows the amino acid sequence of wild-type adeno-associated virus 9 capsid protein VP1 (SEQ ID NO:7; NCBI Reference Sequence: AY530579). Highlighted residues: S162 (aligns with S162 in ttAAV2)—S205 (aligns with S205 in ttAAV2)— G549 (aligns with G548 in ttAAV2)— S586 (aligns with S585 in ttAAV2).

FIG. 8 shows the amino acid sequence of wild-type adeno-associated virus 10 capsid protein VP1 (SEQ ID NO:8). Highlighted residue: G551 (aligns with G548 in ttAAV2).

FIG. 12A. Representative examples of rat brain sections stained with a GFP-specific antibody are shown. The vector was injected into the striatum as shown by the arrow. B. representative example of an injection into the substantia nigra is shown.

FIG. 13 GFP transduction of the eye using ttAAV2 and wtAAV2 is shown. A. Retina in a transverse section is shown after ttAAV2 (top) and wtAAV2 (bottom) vector administration is shown. B. Magnifications of the dashed boxes in A are shown.

FIG. 39 Amino acid sequence of the VP1 capsid protein of AAV-LK03.

LIST OF SEQUENCES

Figure 9:
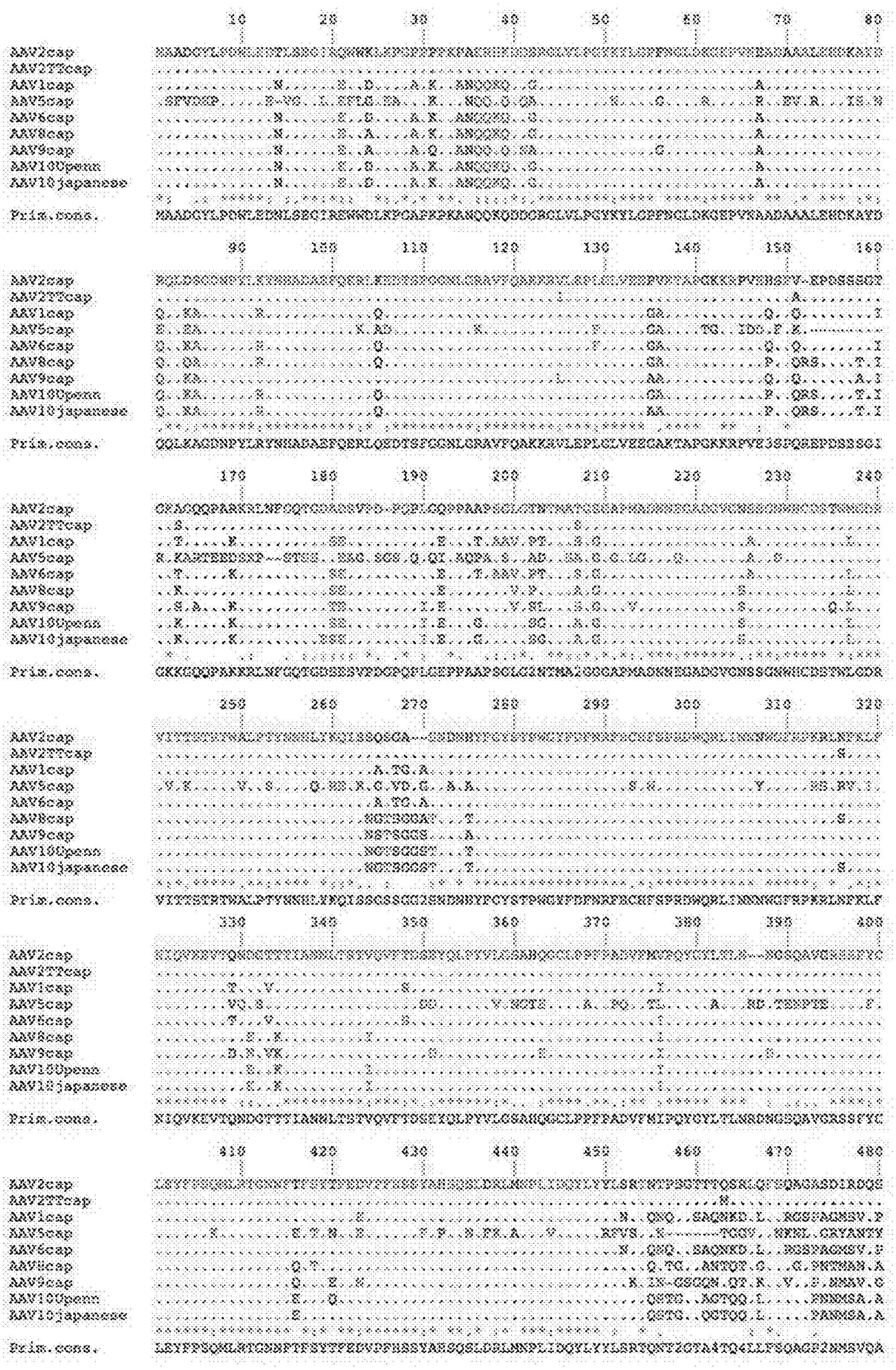
FIG. 9 shows an alignment of AAV capsid protein VP1 amino acid sequences.
Figure 9:
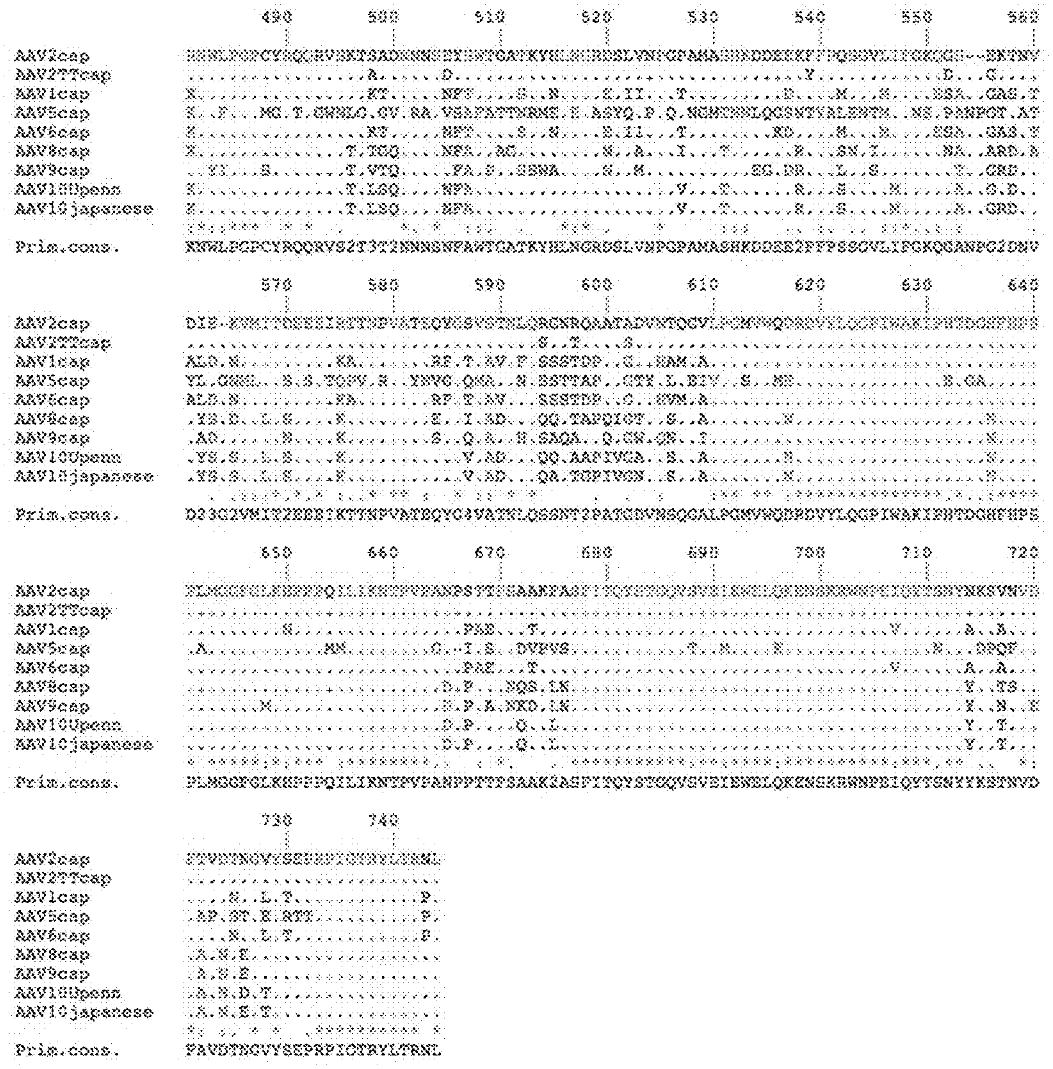

SEQ ID NO:1 is the amino acid sequence of wild-type adeno-associated virus 2 capsid protein VP1 (see FIG. 1).
SEQ ID NO:2 is the amino acid sequence of true-type adeno-associated virus 2 (ttAAV2) capsid protein (see FIG. 2).
SEQ ID NO:3 is the amino acid sequence of wild-type adeno-associated virus 1 capsid protein VP1 (see FIG. 3).
SEQ ID NO:4 is the amino acid sequence of wild-type adeno-associated virus 5 capsid protein VP1 (see FIG. 4).
SEQ ID NO:5 is the amino acid sequence of wild-type adeno-associated virus 6 capsid protein VP1 (see FIG. 5).
SEQ ID NO:6 is the amino acid sequence of wild-type adeno-associated virus 8 capsid protein VP1 (see FIG. 6).
SEQ ID NO:7 is the amino acid sequence of wild-type adeno-associated virus 9 capsid protein VP1 (see FIG. 7).

SEQ ID NO:8 is the amino acid sequence of wild-type adeno-associated virus 10 Upenn capsid protein VP1 (see FIG. 8).

SEQ ID NO:9 is the amino acid sequence of wild-type adeno-associated virus 10 japanese capsid protein VP1 (see FIG. 9).

SEQ ID NO:10 is the consensus amino acid sequence for adeno-associated viruses shown in FIG. 9.

SEQ ID NO:11 is the amino acid sequence of wild-type adeno-associated virus 3B capsid protein VP1 (see FIG. 38).

SEQ ID NO:12 is the amino acid sequence of adeno-associated virus LK-03 capsid protein VP1 (see FIG. 39).

DETAILED DESCRIPTION OF THE INVENTION

In one aspect, the present invention relates to a recombinant adeno-associated virus (AAV) vector. The rAAV vector typically comprises a variant capsid protein which differs compared to a wild-type AAV capsid protein. The variant capsid protein may advantageously confer enhanced infectivity of the vector in brain and/or eye, making the vector particularly suited to delivery of therapeutic agents by gene therapy into these tissues.

Recombinant AAV Vector

The present disclosure provides a recombinant adeno-associated virus (rAAV) vector. "AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes, for example, AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), AAV type 10 (AAV-10, including AAVrh10), AAV type 12 (AAV-12), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, and so on.

The genomic sequences of various serotypes of AAV, as well as the sequences of the native terminal repeats (TRs), Rep proteins, and capsid subunits are known in the art. Such sequences may be found in the literature or in public databases such as GenBank. See, e.g., GenBank Accession Numbers NC-002077 (AAV-1), AF063497 (AAV-1), NC-001401 (AAV-2), AF043303 (AAV-2), NC-001729 (AAV-3), NC-001829 (AAV-4), U89790 (AAV-4), NC-006152 (AAV-5), AF513851 (AAV-7), AF513852 (AAV-8), and NC-006261 (AAV-8); the disclosures of which are incorporated by reference herein. See also, e.g., Srivistava et al. (1983) J. Virology 45:555; Chiorini et al. (1998) J. Virology 71:6823; Chiorini et al. (1999) J. Virology 73: 1309; Bantel-Schaal et al. (1999) J. Virology 73:939; Xiao et al. (1999) J. Virology 73:3994; Muramatsu et al. (1996) Virology 221:208; Shade et al., (1986) J. Virol. 58:921; Gao et al. (2002) Proc. Nat. Acad. Sci. USA 99: 11854; Moris et al. (2004) Virology 33:375-383; international patent publications WO 00/28061, WO 99/61601, WO 98/11244; and U.S. Pat. No. 6,156,303.

An "rAAV vector" as used herein refers to an AAV vector comprising a polynucleotide sequence not of AAV origin (i.e., a polynucleotide heterologous to AAV), typically a sequence of interest for the genetic transformation of a cell. In some embodiments, the heterologous polynucleotide may be flanked by at least one, and sometimesby two, AAV inverted terminal repeat sequences (ITRs). The term rAAV vector encompasses both rAAV vector particles and rAAV vector plasmids. An rAAV vector may either be single-stranded (ssAAV) or self-complementary (scAAV).

An "AAV virus" or "AAV viral particle" or "rAAV vector particle" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

"Recombinant," as used herein means that the vector, polynucleotide, polypeptide or cell is the product of various combinations of cloning, restriction or ligation steps (e.g. relating to a polynucleotide or polypeptide comprised therein), and/or other procedures that result in a construct that is distinct from a product found in nature. A recombinant virus or vector is a viral particle comprising a recombinant polynucleotide. The terms respectively include replicates of the original polynucleotide construct and progeny of the original virus construct.

Variant AAV Capsid Proteins

The rAAV vectors described herein comprise a variant AAV capsid protein. By "variant" it is meant that the AAV capsid protein differs from a corresponding wild type AAV capsid protein of the same serotype. For instance, the variant AAV capsid protein may comprise one or more amino acid substitutions with respect to the corresponding wild type AAV capsid protein. In this context, "corresponding" refers to a capsid protein of the same serotype, i.e. a variant AAV1 capsid protein comprises one or more amino acid substitutions with respect to the corresponding wild type AAV1 capsid protein, a variant AAV2 capsid protein comprises one or more amino acid substitutions with respect to the corresponding wild type AAV2 capsid protein, and so on.

The variant AAV capsid protein may comprise, for example, 1 to 50, 1 to 30, 1 to 20 or 1 to 15 amino acid substitutions with respect to the wild type AAV capsid protein. Preferably the variant AAV capsid protein comprises 1, 2, 3, 4, 5, 6, 7, 8, 9, 10, 11, 12, 13 or 14 amino acid substitutions with respect to the corresponding wild type AAV capsid protein. In preferred embodiments, the variant AAV capsid protein retains at least 70%, at least 80%, at least 90%, at least 95%, at least 96%, at least 97%, at least 98% or at least 99% sequence identity to the wild type capsid protein.

In embodiments of the present invention, the variant AAV capsid protein comprises at least one amino acid substitution with respect to a wild type AAV capsid protein at a position corresponding to one or more of the following positions in an AAV2 capsid protein sequence: 125, 151, 162, 205, 312, 457, 492, 499, 533, 546, 548, 585, 588 and/or 593. In this context, "corresponding" refers to a position in any AAV capsid protein sequence (e.g. in an AAV2 protein sequence or a non-AAV2 capsid protein sequence) which corresponds to one of the above positions in AAV2 capsid protein. In one embodiment, the at least one amino acid substitution is present at one or more of the following positions in an AAV2 capsid protein sequence: 125, 151, 162, 205, 312, 457, 492, 499, 533, 546, 548, 585, 588 and/or 593; or at one or more corresponding positions in an alternative AAV capsid protein sequence.

In general, AAV capsid proteins include VP1, VP2 and VP3. In a preferred embodiment, the capsid protein comprises AAV capsid protein VP1.

Nucleic Acid and Amino Acid Sequences and Sequence Identity

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970)

Of interest is the BestFit program using the local homology algorithm of Smith and Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;

Gap Penalty: 1.00;

Gap Size Penalty: 0.33; and

Joining Penalty: 30.0.

Variant Aav2 Capsid Protein

In one embodiment, the vector comprises a variant AAV2 capsid protein. In this embodiment, the variant AAV2 capsid protein comprises at least one amino acid substitution at one or more of the following positions in an AAV2 capsid protein sequence: 125, 151, 162, 205, 312, 457, 492, 499, 533, 546, 548, 585, 588 and/or 593.

The sequence of wild type AAV2 capsid protein VP1 is known, and is shown in FIG. 1 (SEQ ID NO:1). Wild type AAV2 capsid protein sequences are also available from database accession nos.: NC-001401; UniProt P03135; NCBI Reference Sequence: YP_680426.1; GenBank: AAC03780.1.

Preferably the variant AAV2 capsid protein has at least 70%, at least 80%, at least 90%, at least 95%, at least 96%, at least 97%, at least 98% or at least 99% sequence identity to SEQ ID NO:1. In a preferred embodiment, the variant AAV2 capsid protein comprises a sequence of SEQ ID NO:2, or a sequence having at least 70%, at least 80%, at least 90%, at least 95%, at least 96%, at least 97%, at least 98% or at least 99% sequence identity thereto.

In one embodiment, the variant AAV2 capsid protein comprises one or more of the following residues: I125, A151, S162, S205, S312, M457, A492, D499, Y533, D546, G548, S585, T588 and/or S593. In a preferred embodiment, the variant AAV2 capsid protein comprises one or more of the following amino acid substitutions with respect to a wild type AAV2 capsid protein: V125I, V151A, A162S, T205S, N312S, Q457M, S492A, E499D, F533Y, G546D, E548G, R585S, R588T and/or A593S.

Combinations of Mutations in Aav2 Capsid Protein

The variant AAV2 capsid protein may comprise any combination of the above amino acid substitutions. Therefore in particular embodiments, the variant AAV2 capsid protein comprises 1, 2, 3, 4, 5, 6, 7, 8, 9, 10, 11, 12, 13 or 14 amino acid substitutions selected from the list above. In one embodiment, the variant AAV2 capsid protein comprises all 14 amino acid substitutions disclosed above, e.g. the variant AAV2 capsid protein comprises a sequence of SEQ ID NO:2 (i.e. ttAAV2 or AAV2-TT as referred to herein).

In further embodiments, the variant AAV2 capsid protein may comprise a sub-set of the above 14 mutations. Without being bound by theory, in individual embodiments, the variant AAV2 capsid protein may comprise the following residues, which are divided below into functional groups:

1) S585 and/or T588; these residues may be associated with decreased heparin binding and increased spread of the virus in heparin sulphate proteoglycan-rich brain tissue;
2) S312; this internal serine residue may play a role in capsid-DNA interactions;
3) D546 and/or G548; these residues may be involved in interactions with neutralizing antibodies and thus contribute to in vivo transduction characteristics;
4) S593; this residue is located in the groove between threefold-proximal spikes;
5) M457, A492, D499 and/or Y533; these four amino acids may be involved in receptor binding and are closely situated on the threefold spikes;
6) I125, A151, S162 and/or S205; these residues may be associated with PLA2 activity and/or trafficking of the incoming virus.

It will be appreciated that also contemplated herein are corresponding sub-groups comprising mutations corresponding to the above residues when present at corresponding positions in further AAV serotypes (see below).

In preferred embodiments, the variant AAV2 capsid protein comprises four or more mutations at the positions mentioned above which may be associated with receptor binding, i.e. residues 457, 492, 499 and 533. Thus it is particularly preferred that the variant AAV2 capsid protein comprises the following residues M457, A492, D499 and Y533.

In some preferred embodiments, the variant AAV2 capsid protein is not mutated with respect to the wild type AAV2 capsid protein at position 312, e.g. the variant AAV2 capsid protein comprises the residue N312 (which is present in the wild type AAV2 capsid protein). Thus in some embodiments, the variant AAV2 capsid protein may comprise 1 to 13 of the specific mutations mentioned above, but not the mutation N312S.

Variant AAV Capsid Proteins from Other Serotypes

In further embodiments, the variant AAV capsid protein is from an alternative AAV serotype, i.e. an AAV serotype other than AAV2. For instance, the variant AAV capsid protein may be derived from an AAV1, AAV3B, AAV-LK03, AAV5, AAV6, AAV8, AAV9 or AAV10 (e.g. AAVrh10) capsid protein.

In these embodiments, the variant AAV capsid protein comprises at least one amino acid substitution at one or more positions corresponding to those described above with respect to AAV2. In other words, the variant AAV capsid protein comprises at least one amino acid substitution at a position in an alternative (i.e. non-AAV2) AAV capsid protein sequence which corresponds to positions 125, 151, 162, 205, 312, 457, 492, 499, 533, 546, 548, 585, 588 and/or 593 in an AAV2 capsid protein sequence.

Those skilled in the art would know, based on a comparison of the amino acid sequences of capsid proteins of various AAV serotypes, how to identify positions in capsid proteins from alternative AAV serotypes which correspond to positions 125, 151, 162, 205, 312, 457, 492, 499, 533, 546, 548, 585, 588 and/or 593 in an AAV2 capsid protein. In particular, such positions can easily be identified by sequence alignments as known in the art and described herein. For instance, one such sequence alignment is provided in FIG. 9.

Of particular relevance in this context are positions in alternative AAV capsid protein sequences which correspond in three-dimensional space to positions 125, 151, 162, 205, 312, 457, 492, 499, 533, 546, 548, 585, 588 and/or 593 in an AAV2 capsid protein. Methods for three-dimensional modelling and alignment of protein structures are well known in the art, and can be used to identify such corresponding positions in non-AAV2 capsid protein sequences. Exemplary 3D alignments of AAV2 capsid protein sequences with capsid protein sequences of alternative AAV serotypes (e.g. AAV1, AAV5, AAV6, AAV8 and AAV9) are shown in FIGS. 21 to 25 and discussed below. A skilled person can perform similar 3D alignments with capsid proteins from further serotypes, e.g. AAV2, AAV3, AAV7, AAV10 and AAV12), and identify positions in such sequences which correspond with to the positions defined above in AAV2.

Variant AAV1 Capsid Protein

In one embodiment, the vector comprises a variant AAV1 capsid protein. In this embodiment, the variant AAV1 capsid protein comprises at least one amino acid substitution at one or more of the following positions in the AAV1 capsid protein sequence: 125, 151, 162, 205, 313, 458, 493, 500, 534, 547, 549, 586, 589 and/or 594. These positions in AAV1 capsid protein VP1 correspond to those disclosed above in relation to AAV2.

The sequence of wild type AAV1 capsid protein VP1 is known, and is shown in FIG. 3 (SEQ ID NO:3). A wild type AAV1 capsid protein sequences is also available from database accession no.: NC-002077. Preferably the variant AAV1 capsid protein has at least 70%, at least 80%, at least 90%, at least 95%, at least 96%, at least 97%, at least 98% or at least 99% sequence identity to SEQ ID NO:3.

Wild type AAV1 capsid protein VP1 already contains the following residues at positions which correspond to amino acid residues which are present in the variant AAV2 capsid protein disclosed above (SEQ ID NO:2, ttAAV2), but not wild type AAV2 (SEQ ID NO:1): S205 (aligns with S205 in ttAAV2); G549 (aligns with G548 in ttAAV2); S586 (aligns with S585 in ttAAV2); and T589 (aligns with T588 in ttAAV2). Accordingly, in a preferred embodiment, the variant AAV1 capsid protein comprises one or more of the following amino acid substitutions with respect to a wild type AAV1 capsid protein: V125I, Q151A, T162S, N313S, N458M, K493A, N500D, F534Y, S547D, and/or G594S. Typically such a variant AAV1 capsid protein may share one or more functional properties with the variant AAV2 capsid protein (SEQ ID NO:2, ttAAV2), e.g. may confer increased infectivity and/or transduction of neuronal of retinal tissue compared to wild type AAV1 capsid protein.

In alternative embodiments, the variant AAV1 capsid protein comprises one or more amino acid substitutions which correspond to reversions of mutations present in ttAAV2 back to the wild type AAV2 sequence. For instance, the variant AAV1 capsid protein may comprise one or more of the following substitutions: S205T, G549E, S586R and/or T589R. Typically such a variant AAV1 capsid protein may share one or more functional properties with the wild type AAV2 capsid protein (SEQ ID NO:1), e.g. may confer reduced infectivity and/or transduction of neuronal of retinal tissue compared to wild type AAV1 capsid protein.

Variant AAV5 Capsid Protein

In one embodiment, the vector comprises a variant AAV5 capsid protein. In this embodiment, the variant AAV5 capsid protein comprises at least one amino acid substitution at one or more of the following positions in the AAV5 capsid protein sequence: 124, 150, 153, 195, 303, 444, 479, 486, 520, 533, 537, 575, 578 and/or 583. These positions in AAV5 capsid protein VP1 correspond to those disclosed above in relation to AAV2.

The sequence of wild type AAV5 capsid protein VP1 is known, and is shown in FIG. 4 (SEQ ID NO:4). A wild type AAV5 capsid protein sequences is also available from database accession no.: AF085716. Preferably the variant AAV5 capsid protein has at least 70%, at least 80%, at least 90%, at least 95%, at least 96%, at least 97%, at least 98% or at least 99% sequence identity to SEQ ID NO:4.

Wild type AAV5 capsid protein VP1 already contains the following residues at positions which correspond to amino acid residues which are present in the variant AAV2 capsid protein disclosed above (SEQ ID NO:2, ttAAV2), but not wild type AAV2 (SEQ ID NO:1): G537 (aligns with G548 in ttAAV2); S575 (aligns with S585 in ttAAV2); T578 (aligns with T588 in ttAAV2). Accordingly, in a preferred embodiment, the variant AAV5 capsid protein comprises one or more of the following amino acid substitutions with respect to a wild type AAV5 capsid protein: V124I, K150A, K153S, A195S, R303S, T444M, S479A, V486D, T520Y, P533D, and/or G583S. Typically such a variant AAV5 capsid protein may share one or more functional properties with the variant AAV2 capsid protein (SEQ ID NO:2, ttAAV2), e.g. may confer increased infectivity and/or transduction of neuronal of retinal tissue compared to wild type AAV5 capsid protein.

In alternative embodiments, the variant AAV5 capsid protein comprises one or more amino acid substitutions which correspond to reversions of mutations present in ttAAV2 back to the wild type AAV2 sequence. For instance, the variant AAV5 capsid protein may comprise one or more of the following substitutions: G537E, S575R and/or T578R. Typically such a variant AAV5 capsid protein may share one or more functional properties with the wild type AAV2 capsid protein (SEQ ID NO:1), e.g. may confer reduced infectivity and/or transduction of neuronal of retinal tissue compared to wild type AAV5 capsid protein.

Variant Aav6 Capsid Protein

In one embodiment, the vector comprises a variant AAV6 capsid protein. In this embodiment, the variant AAV6 capsid protein comprises at least one amino acid substitution at one or more of the following positions in the AAV6 capsid protein sequence: 125, 151, 162, 205, 313, 458, 493, 500, 534, 547, 549, 586, 589 and/or 594. These positions in AAV6 capsid protein VP1 correspond to those disclosed above in relation to AAV2.

The sequence of wild type AAV6 capsid protein VP1 is known, and is shown in FIG. 5 (SEQ ID NO:5). A wild type AAV6 capsid protein sequences is also available from database accession no.: AF028704. Preferably the variant AAV6 capsid protein has at least 70%, at least 80%, at least 90%, at least 95%, at least 96%, at least 97%, at least 98% or at least 99% sequence identity to SEQ ID NO:5.

Wild type AAV6 capsid protein VP1 already contains the following residues at positions which correspond to amino acid residues which are present in the variant AAV2 capsid protein disclosed above (SEQ ID NO:2, ttAAV2), but not wild type AAV2 (SEQ ID NO:1): S205 (aligns with S205 in ttAAV2); G549 (aligns with G548 in ttAAV2); S586 (aligns with S585 in ttAAV2); T589 (aligns with T588 in ttAAV2). Accordingly, in a preferred embodiment, the variant AAV6 capsid protein comprises one or more of the following amino acid substitutions with respect to a wild type AAV6 capsid protein: V125I, Q151A, T162S, N313S, N458M, K493A, N500D, F534Y, S547D, and/or G594S. Typically such a variant AAV6 capsid protein may share one or more functional properties with the variant AAV2 capsid protein (SEQ ID NO:2, ttAAV2), e.g. may confer increased infectivity and/or transduction of neuronal of retinal tissue compared to wild type AAV6 capsid protein.

In alternative embodiments, the variant AAV6 capsid protein comprises one or more amino acid substitutions which correspond to reversions of mutations present in ttAAV2 back to the wild type AAV2 sequence. For instance, the variant AAV6 capsid protein may comprise one or more of the following substitutions: S205T, G549E, S586R and/or T589R. Typically such a variant AAV6 capsid protein may share one or more functional properties with the wild type AAV2 capsid protein (SEQ ID NO:1), e.g. may confer reduced infectivity and/or transduction of neuronal of retinal tissue compared to wild type AAV6 capsid protein.

Variant AAV8 Capsid Protein

In one embodiment, the vector comprises a variant AAV8 capsid protein. In this embodiment, the variant AAV8 capsid protein comprises at least one amino acid substitution at one or more of the following positions in the AAV8 capsid protein sequence: 125, 151, 163, 206, 315, 460, 495, 502, 536, 549, 551, 588, 591 and/or 596. These positions in AAV8 capsid protein VP1 correspond to those disclosed above in relation to AAV2.

The sequence of wild type AAV8 capsid protein VP1 is known, and is shown in FIG. 6 (SEQ ID NO:6). A wild type AAV8 capsid protein sequences is also available from database accession no.: NC_006261. Preferably the variant AAV8 capsid protein has at least 70%, at least 80%, at least 90%, at least 95%, at least 96%, at least 97%, at least 98% or at least 99% sequence identity to SEQ ID NO:6.

Wild type AAV8 capsid protein VP1 already contains the following residues at positions which correspond to amino acid residues which are present in the variant AAV2 capsid protein disclosed above (SEQ ID NO:2, ttAAV2), but not wild type AAV2 (SEQ ID NO:1): S315 (aligns with S312 in ttAAV2); T591 (aligns with T588 in ttAAV2). Accordingly, in a preferred embodiment, the variant AAV8 capsid protein comprises one or more of the following amino acid substitutions with respect to a wild type AAV8 capsid protein: V125I, Q151A, K163S, A206S, T460M, T495A, N502D, F536Y, N549D, A551G, Q588S and/or G596S. Typically such a variant AAV8 capsid protein may share one or more functional properties with the variant AAV2 capsid protein (SEQ ID NO:2, ttAAV2), e.g. may confer increased infectivity and/or transduction of neuronal of retinal tissue compared to wild type AAV8 capsid protein.

In alternative embodiments, the variant AAV8 capsid protein comprises one or more amino acid substitutions which correspond to reversions of mutations present in ttAAV2 back to the wild type AAV2 sequence. For instance, the variant AAV8 capsid protein may comprise one or more of the following substitutions: S315N and/or T591R. Typically such a variant AAV8 capsid protein may share one or more functional properties with the wild type AAV2 capsid protein (SEQ ID NO:1), e.g. may confer reduced infectivity and/or transduction of neuronal of retinal tissue compared to wild type AAV8 capsid protein.

In one embodiment, the variant AAV8 capsid protein comprises an amino acid substitution with respect to a wild type AAV8 capsid protein at position 315 in an AAV8 capsid protein sequence. For instance, the variant AAV8 capsid protein may comprise the residue N315. Thus in one embodiment the variant AAV8 capsid protein comprises the amino acid substitution S315N with respect to a wild type AAV8 capsid protein.

Variant Aav9 Capsid Protein

In one embodiment, the vector comprises a variant AAV9 capsid protein. In this embodiment, the variant AAV9 capsid protein comprises at least one amino acid substitution at one or more of the following positions in the AAV9 capsid protein sequence: 125, 151, 162, 205, 314, 458, 493, 500, 534, 547, 549, 586, 589 and/or 594. These positions in AAV9 capsid protein VP1 correspond to those disclosed above in relation to AAV2.

The sequence of wild type AAV9 capsid protein VP1 is known, and is shown in FIG. 7 (SEQ ID NO:7). A wild type AAV9 capsid protein sequences is also available from database accession no.: AY530579. Preferably the variant AAV9 capsid protein has at least 70%, at least 80%, at least 90%, at least 95%, at least 96%, at least 97%, at least 98% or at least 99% sequence identity to SEQ ID NO:7.

Wild type AAV9 capsid protein VP1 already contains the following residues at positions which correspond to amino acid residues which are present in the variant AAV2 capsid protein disclosed above (SEQ ID NO:2, ttAAV2), but not wild type AAV2 (SEQ ID NO:1): S162 (aligns with S162 in ttAAV2); S205 (aligns with S205 in ttAAV2); G549 (aligns with G548 in ttAAV2); S586 (aligns with S585 in ttAAV2). Accordingly, in a preferred embodiment, the variant AAV9 capsid protein comprises one or more of the following amino acid substitutions with respect to a wild type AAV9 capsid protein: L125I, Q151A, N314S, Q458M, V493A, E500D, F534Y, G547D, A589T and/or G594S. Typically such a variant AAV9 capsid protein may share one or more functional properties with the variant AAV2 capsid protein (SEQ ID NO:2, ttAAV2), e.g. may confer increased infectivity and/or transduction of neuronal of retinal tissue compared to wild type AAV9 capsid protein.

In alternative embodiments, the variant AAV9 capsid protein comprises one or more amino acid substitutions which correspond to reversions of mutations present in ttAAV2 back to the wild type AAV2 sequence. For instance, the variant AAV9 capsid protein may comprise one or more of the following substitutions: S162A, S205T, G549E and/or S586R. Typically such a variant AAV9 capsid protein may share one or more functional properties with the wild type AAV2 capsid protein (SEQ ID NO:1), e.g. may confer reduced infectivity and/or transduction of neuronal of retinal tissue compared to wild type AAV9 capsid protein.

Variant Aav10 Capsid Protein

In one embodiment, the vector comprises a variant AAV10 capsid protein. As used herein, "AAV10" includes AAVrh10. In this embodiment, the variant AAV10 (e.g. AAVrh10) capsid protein comprises at least one amino acid substitution at one or more of the following positions in the AAV10 capsid protein sequence: 125, 151, 163, 206, 315, 460, 495, 502, 536, 549, 551, 588, 591 and/or 596. These positions in AAV10 capsid protein VP1 correspond to those disclosed above in relation to AAV2.

The sequence of wild type AAV10 capsid protein VP1 is known, and is shown in FIG. 8 (SEQ ID NO:8). Preferably the variant AAV10 capsid protein has at least 70%, at least 80%, at least 90%, at least 95%, at least 96%, at least 97%, at least 98% or at least 99% sequence identity to SEQ ID NO:8.

Wild type AAV10 capsid protein VP1 already contains the following residue at a position which corresponds to an amino acid residue which is present in the variant AAV2 capsid protein disclosed above (SEQ ID NO:2, ttAAV2), but not wild type AAV2 (SEQ ID NO:1): G551 (aligns with G548 in ttAAV2). Accordingly, in a preferred embodiment, the variant AAV10 capsid protein comprises one or more of the following amino acid substitutions with respect to a wild type AAV10 capsid protein: V125I, Q151A, K163S, A206S, N315S, T460M, L495A, N502D, F536Y, G549D, Q588S, A591T and/or G596S. Typically such a variant AAV10 capsid protein may share one or more functional properties with the variant AAV2 capsid protein (SEQ ID NO:2, ttAAV2), e.g. may confer increased infectivity and/or transduction of neuronal of retinal tissue compared to wild type AAV10 capsid protein.

In alternative embodiments, the variant AAV10 capsid protein comprises an amino acid substitution which corresponds to a reversion of a mutations present in ttAAV2 back to the wild type AAV2 sequence. For instance, the variant AAV10 capsid protein may comprise the following substitution: G551E. Typically such a variant AAV10 capsid protein may share one or more functional properties with the wild type AAV2 capsid protein (SEQ ID NO:1), e.g. may confer reduced infectivity and/or transduction of neuronal of retinal tissue compared to wild type AAV10 capsid protein.

Variant Aav3B Capsid Protein

In one embodiment, the vector comprises a variant AAV3B capsid protein. In this embodiment, the variant AAV3B capsid protein may comprise an amino acid substitution with respect to a wild type AAV3B capsid protein at position 312. For instance, the variant AAV3B capsid protein may comprise the residue N312. Thus in one embodiment the variant AAV8 capsid protein comprises the amino acid substitution S312N with respect to a wild type AAV8 capsid protein. In further embodiments, the variant AAV3B capsid protein may comprise one or more additional mutations at positions which correspond to those disclosed above in relation to AAV2.

The sequence of wild type AAV3B capsid protein VP1 is known, and is shown in FIG. 38 (SEQ ID NO:11). A wild type AAV3B capsid protein sequence is also available from NCBI database accession no. AF028705. Preferably the variant AAV3B capsid protein has at least 70%, at least 80%, at least 90%, at least 95%, at least 96%, at least 97%, at least 98% or at least 99% sequence identity to SEQ ID NO:11.

Variant AAV-LK03 Capsid Protein

In one embodiment, the vector comprises a variant AAV-LK03 capsid protein. In this embodiment, the variant AAV-LK03 capsid protein may comprise an amino acid substitution at position 312 with respect to a AAV-LK03 capsid protein sequence as defined in SEQ ID NO:12. For instance, the variant AAV-LK03 capsid protein may comprise the residue N312. Thus in one embodiment the variant AAV-LK03 capsid protein comprises the amino acid substitution S312N with respect to a AAV-LK03 capsid protein sequence as defined in SEQ ID NO:12. In further embodiments, the variant AAV-LK03 capsid protein may comprise one or more additional mutations at positions which correspond to those disclosed above in relation to AAV2.

The sequence of wild type AAV-LK03 capsid protein VP1 is known, and is shown in FIG. 39 (SEQ ID NO:12). A AAV-LK03 capsid protein sequence is also disclosed in WO 2013/029030 as sequence number 31 therein. Preferably the variant AAV-LK03 capsid protein has at least 70%, at least 80%, at least 90%, at least 95%, at least 96%, at least 97%, at least 98% or at least 99% sequence identity to SEQ ID NO:12.

Gene Products

In one embodiment, the rAAV further comprises a heterologous nucleic acid comprising a nucleotide sequence encoding a gene product. A "gene" refers to a polynucleotide containing at least one open reading frame that is capable of encoding a particular protein after being transcribed and translated. A "gene product" is a molecule resulting from expression of a particular gene. Gene products include, e.g., a polypeptide, an aptamer, an interfering RNA, an mRNA, and the like.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

In some embodiments, the gene product is an interfering RNA. In some embodiments, the gene product is an aptamer. In some embodiments, the gene product is a polypeptide.

Interfering RNA

Where the gene product is an interfering RNA (RNAi), suitable RNAi include RNAi that decrease the level of an apoptotic or angiogenic factor in a cell. For example, an RNAi can be an shRNA or siRNA that reduces the level of a gene product that induces or promotes apoptosis in a cell. Genes whose gene products induce or promote apoptosis are referred to herein as "pro-apoptotic genes" and the products of those genes (mRNA; protein) are referred to as "pro-apoptotic gene products." Pro-apoptotic gene products include, e.g., Bax, Bid, Bak, and Bad gene products. See, e.g., U.S. Pat. No. 7,846,730.

Interfering RNAs could also be against an angiogenic product, for example VEGF (e.g., Candy; see, e.g., U.S. Patent Publication No. 2011/0143400; U.S. Patent Publication No. 2008/0188437; and Reich et al. (2003) Mol. Vis. 9:210), VEGFR1 (e.g., Sirna-027; see, e.g., Kaiser et al. (2010) Am. J. Ophthalmol. 150:33; and Shen et al. (2006) Gene Ther. 13:225), or VEGFR2 (Kou et al. (2005) Biochem. 44: 15064). See also, U.S. Pat. Nos. 6,649,596, 6,399,586, 5,661,135, 5,639,872, and 5,639,736; and 7,947, 659 and 7,919,473.

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

A "short hairpin RNA," or shRNA, is a polynucleotide construct that can be made to express an interfering RNA such as siRNA.

Aptamers

Where the gene product is an aptamer, exemplary aptamers of interest include an aptamer against vascular endothelial growth factor (VEGF). See, e.g., Ng et al. (2006) Nat. Rev. Drug Discovery 5: 123; and Lee et al. (2005) Proc. Natl. Acad. Sci. USA 102: 18902. Also suitable for use is a PDGF-specific aptamer, e.g., E10030; see, e.g., Ni and Hui (2009) Ophthalmologica 223:401; and Akiyama et al. (2006) J. Cell Physiol. 207:407).

Polypeptides

In one embodiment, the gene product is a therapeutic protein. A "therapeutic" peptide or protein is a peptide or protein that may alleviate or reduce symptoms that result from an absence or defect in a protein in a cell or subject. Alternatively, a "therapeutic" peptide or protein is one that otherwise confers a benefit to a subject, e.g., anti-degenerative effects.

Where the gene product is a polypeptide, the polypeptide is generally a polypeptide that enhances function of a cell, for example a cell present in neuronal, retinal or liver tissue, e.g., a hepatocyte, a neuron, a glial cell, a rod or cone photoreceptor cell, a retinal ganglion cell, a Muller cell, a bipolar cell, an amacrine cell, a horizontal cell, or a retinal pigmented epithelial cell.

Exemplary polypeptides include neuroprotective polypeptides (e.g., GDNF, CNTF, NT4, NGF, and NTN); anti-angiogenic polypeptides (e.g., a soluble vascular endothelial growth factor (VEGF) receptor; a VEGF-binding antibody; a VEGF-binding antibody fragment (e.g., a single chain anti-VEGF antibody); endostatin; tumstatin; angiostatin; a soluble Fit polypeptide (Lai et al. (2005) Mol. Ther. 12:659); an Fc fusion protein comprising a soluble Fit polypeptide (see, e.g., Pechan et al. (2009) Gene Ther. 16: 10); pigment epithelium-derived factor (PEDF); a soluble Tie-2 receptor; etc.); tissue inhibitor of metalloproteinases-3 (TIMP-3); a light-responsive opsin, e.g., a rhodopsin; anti-apoptotic polypeptides (e.g., Bcl-2, Bcl-Xl); and the like. Suitable polypeptides include, but are not limited to, glial derived neurotrophic factor (GDNF); fibroblast growth factor 2; neurturin (NTN); ciliary neurotrophic factor (CNTF); nerve growth factor (NGF); neurotrophin-4 (NT4); brain derived neurotrophic factor (BDNF); epidermal growth factor; rhodopsin; X-linked inhibitor of apoptosis; and Sonic hedgehog. Suitable polypeptides are disclosed, for example, in WO WO 2012/145601.

Exemplary polypeptides for gene deliver to the liver include, for example, PBGD (porphobilinogen deaminase) IDUA (iduronidase) Fah (fumarylacetoacetate hydrolyase) A1AT (alpha(1)-antitrypsin), 1A1(hUGT1A1) (uridine disphoshate glucuronyltransferase), HCCS1 (hepatocellular carcinoma suppressor 1), CD (cytosine deaminase), SOCS3 (suppressor of cytokine signaling 3), TNF (tumor necrosis factor), thymidine kinase, IL-24 (interleukin-24), IL-12 (interleukin-12), and TRAIL (tumor necrosis factor-related apoptosis-inducing ligand).

Regulatory Sequences

In some embodiments, a nucleotide sequence encoding a gene product of interest is operably linked to a constitutive promoter. In other embodiments, a nucleotide sequence encoding a gene product of interest is operably linked to an inducible promoter. In some instances, a nucleotide sequence encoding a gene product of interest is operably linked to a tissue specific or cell type specific regulatory element.

For example, in some instances, a nucleotide sequence encoding a gene product of interest is operably linked to a hepatocyte-specific, neuron-specific or photoreceptor-specific regulatory element (e.g., a photoreceptor-specific promoter), e.g., a regulatory element that confers selective expression of the operably linked gene in a neuron or photoreceptor cell. Suitable photoreceptor-specific regulatory elements include, e.g., a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9: 1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225). Suitable neuronal-specific promoters include neuron-specific enolase (NSE) promoter, Andersen et al. Cell. Mol. Neurobiol., 13:503-15 (1993; neurofilament light-chain gene promoter, Piccioli et al., Proc. Natl. Acad. Sci. USA, 88:561 1-5 (1991); and the neuron-specific vgf gene promoter, Piccioli et al., Neuron, 15:373-84 (1995)]; among others. Suitable hepatocyte-specific promoters include an albumin promoter (Heard et al., Mol Cell Biol 1987; 7: 2425) or an alpha 1-antitrypsin promoter (Hafenrichter et al. Blood 1994; 84, 3394-404).

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

Pharmaceutical Compositions

The present disclosure provides a pharmaceutical composition comprising: a) a rAAV vector, as described above; and b) a pharmaceutically acceptable carrier, diluent, excipient, or buffer. In some embodiments, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol.

Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7(th) ed., Lippincott, Williams, & Wilkins; and Handbook of Pharmaceutical Excipients (2000) A. H. Kibbe et al., eds., 3 rd ed. Amer. Pharmaceutical Assoc.

In particular embodiments, the present invention provides a pharmaceutical composition comprising a rAAV vector as described above in a pharmaceutically-acceptable carrier or other medicinal agents, pharmaceutical agents, carriers, adjuvants, diluents, etc. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

By "pharmaceutically acceptable" it is meant a material that is not biologically or otherwise undesirable, e.g., the material may be administered to a subject without causing any undesirable biological effects. Thus, such a pharmaceutical composition may be used, for example, in transfection of a cell ex vivo or in administering a viral particle or cell directly to a subject.

Methods of Delivering a Gene Product to a Tissue or Cell (for Example a Hepatic, Neuronal or Retinal Tissue or Cell) and Treatment Methods The methods of the present invention provide a means for delivering heterologous nucleic acid sequences into a host tissue or cell, including both dividing and non-dividing cells. The vectors and other reagents, methods and pharmaceutical formulations of the present invention are additionally useful in a method of administering a protein or peptide to a subject in need thereof, as a method of treatment or otherwise. In this manner, the protein or peptide may thus be produced in vivo in the subject. The subject may be in need of the protein or peptide because the subject has a deficiency of the protein or peptide, or because the production of the protein or peptide in the subject may impart some therapeutic effect, as a method of treatment or otherwise, and as explained further below.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

In general, the present invention may be employed to deliver any foreign nucleic acid with a biological effect to treat or ameliorate the symptoms associated with any disorder related to gene expression in any organ, tissue or cell, especially those associated with e.g. the liver, brain or eye. Illustrative disease states include, but are not limited to: lysosomal storage disease, acute intermittent porphyria, ornithine transcarbamylase deficiency, alpha(1)-antitrypsin deficiency, acute liver failure, Pompe disease, Tyrosinemia, Crigler-Najjar syndrome, hepatitis, cirrhosis, hepatocellular carcinoma, AIDS, Alzheimer's disease, Parkinson's disease, Huntington's disease, amyotrophic lateral sclerosis, epilepsy, and other neurological disorders, cancer (e.g. brain cancer), retinal degenerative diseases and other diseases of the eye.

Gene transfer has substantial potential use in understanding and providing therapy for disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific integration of nucleic sequences to cause mutations or to correct defects is also possible.

In one aspect the present invention provides a method of delivering a gene product to a tissue or cell (e.g. a hepatic, neuronal or retinal tissue or cell) in a subject, the method comprising administering to the subject a rAAV vector as described above. The gene product can be a polypeptide or an interfering RNA (e.g., an shRNA, an siRNA, and the like), or an aptamer, e.g. as described above. The cell may, for example, be a blood cell, stem cell, bone marrow (e.g. hematopoietic) cell, liver cell, cancer cell, vascular cell, pancreatic cell, neural cell, glial cell, ocular or retinal cell, epithelial or endothelial cell, dendritic cell, fibroblast, lung cell, muscle cell, cardiac cell, intestinal cell or renal cell. Similarly the tissue may, for example, be selected from blood, bone marrow, muscle tissue (e.g. skeletal muscle, cardiac muscle or smooth muscle including vascular smooth muscle), central or peripheral nervous system tissue (e.g. brain, neuronal tissue or retinal tissue), pancreatic tissue, liver tissue, kidney tissue, lung tissue, intestinal tissue or heart tissue.

Delivering a gene product to a retinal cell can provide for treatment of a retinal disease. The retinal cell can be a photoreceptor, a retinal ganglion cell, a Muller cell, a bipolar cell, an amacrine cell, a horizontal cell, or a retinal pigmented epithelial cell. In some cases, the retinal cell is a photoreceptor cell, e.g., a rod or cone cell. Similarly, delivering a gene product to a neuronal tissue or cell can provide for treatment of a neurological disorder. The gene product may be delivered to various cell types present in neuronal tissue, e.g. neurons or glial cells (e.g. astrocytes, oligodendrocytes and so on). Delivering a gene product to the liver may provide treatment for a hepatic disorder. The gene product may be delivered to, for example, hepatocytes.

The present disclosure provides a method of treating a disease (e.g. a hepatic, neurological or ocular disease), the method comprising administering to an individual in need thereof an effective amount of a rAAV vector as described above. A subject rAAV vector can be administered via intracranial injection, intracerebral injection, intraocular injection, by intravitreal injection, retinal injection, subretinal injection, intravenous injection or by any other convenient mode or route of administration.

Further exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspensions in liquid prior to injection, or as emulsions. Alternatively, one may administer the virus in a local rather than systemic manner, for example in a depot or sustained-release formation.

Recombinant virus vectors are preferably administered to the subject in an amount that is sufficient to result in infection (or transduction) and expression of the heterologous nucleic acid sequence in cells (e.g. liver, neuronal or retinal cells) of the subject. Preferably the target cells are hepatocytes, neural cells (including cells of the central and peripheral nervous systems, in particular, brain cells) or retinal cells. In some cases, the retinal cell is a photoreceptor cell (e.g., rods and/or cones). In other cases, the retinal cell is an RGC cell. In other cases, the retinal cell is an RPE cell. In other cases, retinal cells may include amacrine cells, bipolar cells, and horizontal cells.

Preferably the vector is administered in a therapeutically effective amount. A "therapeutically-effective" amount as used herein is an amount of that is sufficient to alleviate (e.g., mitigate, decrease, reduce) at least one of the symptoms associated with a disease state. Alternatively stated, a "therapeutically-effective" amount is an amount that is sufficient to provide some improvement in the condition of the subject. A "therapeutically effective amount" will fall in a relatively broad range that can be determined through experimentation and/or clinical trials. For example, for in vivo injection, a therapeutically effective dose will be on the order of from about $10^6$ to about $10^{15}$ of rAAV virions, e.g., from about $10^8$ to $10^{12}$ rAAV virions. For in vitro transduction, an effective amount of rAAV virions to be delivered to cells will be on the order of from about $10^8$ to about $10^{13}$ of the rAAV virions. Other effective dosages can be readily established by one of ordinary skill in the art through routine trials establishing dose response curves.

In some embodiments, more than one administration (e.g., two, three, four or more administrations) may be employed to achieve the desired level of gene expression over a period of various intervals, e.g., daily, weekly, monthly, yearly, etc.

Neurological diseases which may be treated include any disease associated with the brain or CNS, including psychiatric diseases. Diseases of the brain fall into two general categories: (a) pathologic processes such as infections, trauma and neoplasm; and (b) diseases unique to the nervous system which include diseases of myelin and degeneration of neurons. Disease from either category may be treated. For example, the neurological disease may be selected from neurodegenerative diseases such as Alzheimer's Disease, Parkinson's Disease, amyotrophic lateral sclerosis (ALS), spinal muscular atrophy and cerebella degeneration; schizophrenia; epilepsy; ischemia-related disease and stroke; demyelinating diseases such as multiple sclerosis, perivenous encephalitis, leukodystrophies such as metachromatic leukodystrophy due to deficiency of arylsulfatase A, Krabbe's disease due to deficiency of galactocerebroside beta-galactosidase, adrenoleukodystrophy and adrenomyeloneuropathy; post-viral diseases such as progressive multifocal leukoencephalopathy, acute disseminated encephalomyelitis, acute necrotizing hemorrhagic leukoencephalitis; mitochondrial encephalomyopathies; neurological cancers, such as primary brain tumors including glioma, meningioma, neurinoma, pituitary adenoma, medulloblastoma, craniopharyngioma, hemangioma, epidermoid, sarcoma and intracranial metastasis from other tumor sources; neurological infections or neurological inflammatory conditions.

Ocular diseases that can be treated using a subject method include, but are not limited to, acute macular neuroretinopathy; Behcet's disease; choroidal neovascularization; diabetic uveitis; histoplasmosis; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy; photocoagulation, radiation retinopathy; epiretinal membrane disorders; branch retinal vein occlusion; anterior ischemic optic neuropathy; non-retinopathy diabetic retinal dysfunction; retinoschisis; retinitis pigmentosa; glaucoma; Usher syndrome, cone-rod dystrophy; Stargardt disease (fundus flavimaculatus); inherited macular degeneration; chorioretinal degeneration; Leber congenital amaurosis; congenital stationary night blindness; choroideremia; Bardet-Biedl syndrome; macular telangiectasia; Leber's hereditary optic neuropathy; retinopathy of prematurity; and disorders of color vision, including achromatopsia, protanopia, deuteranopia, and tritanopia.

Diseases of the liver which may be treated include, for example, lysosomal storage diseases, e.g. acute intermittent porphyria, ornithine transcarbamylase deficiency, Wilson's disease, mucopolysaccharidoses (e.g. MPS type I or MPS type VI), Sly syndrome, Pompe disease, tyrosinemia, alpha (1)-antitrypsin deficiency, Crigler-Najjar syndrome; hepatitis A, B or C; liver cirrhosis; liver cancer, e.g. hepatocellular carcinoma; or acute liver failure.

The present invention finds use in both veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are the most preferred. Human subjects include fetal, neonatal, infant, juvenile and adult subjects.

Transduction of Tissue (for Example Hepatic, Neuronal or Retinal Tissue)

In some embodiments, the rAAV vectors disclosed herein exhibit increased transduction of a tissue (e.g. hepatic, neuronal and/or retinal tissues), e.g. compared to a corresponding AAV vector (from the same serotype) comprising a wild type AAV capsid protein. For example, the rAAV vector may exhibit at least 10%, 50%, 100%, 500% or 1000% increased infectivity, compared to the infectivity by an AAV virion comprising the corresponding wild type AAV capsid protein.

In further embodiments, the rAAV vectors disclosed herein may selectively or specifically infect a tissue (e.g. hepatic, neuronal or retinal tissues), e.g. show increased transduction of hepatic, neuronal or retinal cells compared to other cell types. For instance, the rAAV vector may exhibit at least 10%, 50%, 100%, 500% or 1000% increased infectivity of a particular cell type (e.g. hepatic, neuronal or retinal cells), compared to another cell type (e.g. non-hepatic, non-neuronal and/or non-retinal cells). For instance, the rAAV vector may selectively infect hepatocytes, neurons and/or photoreceptor cells compared to cells outside the liver, brain and/or eye.

Where the recombinant AAV vector exhibits increased transduction of a neuronal or retinal tissue, e.g. where the vector is used to treat a neurological or ocular disorder, the vector preferably comprises a variant AAV2 capsid protein.

Where the recombinant AAV vector exhibits increased transduction of liver tissue, e.g. where the vector is used to treat a hepatic disorder, the vector preferably comprises a variant AAV3B, AAV-LK03 or AAV8 capsid protein.

Nucleic Acids and Host Cells

The present disclosure provides an isolated nucleic acid comprising a nucleotide sequence that encodes a variant adeno-associated virus (AAV) capsid protein as described above. The isolated nucleic acid can be comprised in an AAV vector, e.g., a recombinant AAV vector.

A recombinant AAV vector comprising such a variant AAV capsid protein-encoding sequence can be used to generate a recombinant AAV virion (i.e. a recombinant AAV vector particle). Thus, the present disclosure provides a recombinant AAV vector that, when introduced into a suitable cell, can provide for production of a recombinant AAV virion.

The present invention further provides host cells, e.g., isolated (genetically modified) host cells, comprising a subject nucleic acid. A subject host cell can be an isolated cell, e.g., a cell in in vitro culture. A subject host cell is useful for producing a subject rAAV virion, as described below. Where a subject host cell is used to produce a subject rAAV virion, it is referred to as a "packaging cell." In some embodiments, a subject host cell is stably genetically modified with a subject nucleic acid. In other embodiments, a subject host cell is transiently genetically modified with a subject nucleic acid.

A subject nucleic acid is introduced stably or transiently into a host cell, using established techniques, including, but not limited to, electroporation, calcium phosphate precipitation, liposome-mediated transfection, and the like. For stable transformation, a subject nucleic acid will generally further include a selectable marker, e.g., any of several well-known selectable markers such as neomycin resistance, and the like.

A subject host cell is generated by introducing a subject nucleic acid into any of a variety of cells, e.g., mammalian cells, including, e.g., murine cells, and primate cells (e.g., human cells). Suitable mammalian cells include, but are not limited to, primary cells and cell lines, where suitable cell lines include, but are not limited to, 293 cells, COS cells, HeLa cells, Vero cells, 3T3 mouse fibroblasts, C3H10T1/2 fibroblasts, CHO cells, and the like. Non-limiting examples of suitable host cells include, e.g., HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RATI cells, mouse L cells (ATCC No. CCLI.3), human embryonic kidney (HEK) cells (ATCC No. CRL1573), HLHepG2 cells, and the like. A subject host cell can also be made using a baculovirus to infect insect cells such as Sf9 cells, which produce AAV (see, e.g., U.S. Pat. No. 7,271,002; U.S. patent application Ser. No. 12/297,958).

In some embodiments, a subject genetically modified host cell includes, in addition to a nucleic acid comprising a nucleotide sequence encoding a variant AAV capsid protein, as described above, a nucleic acid that comprises a nucleotide sequence encoding one or more AAV rep proteins. In other embodiments, a subject host cell further comprises an rAAV vector. An rAAV virion can be generated using a subject host cell. Methods of generating an rAAV virion are described in, e.g., U.S. Patent Publication No. 2005/0053922 and U.S. Patent Publication No. 2009/0202490.

As used herein, "packaging" refers to a series of intracellular events that result in the assembly and encapsidation of an AAV particle. AAV "rep" and "cap" genes refer to polynucleotide sequences encoding replication and encapsidation proteins of adeno-associated virus. AAV rep and cap are referred to herein as AAV "packaging genes." Assembly associated protein (AAP) is the product of an open reading frame within the cap gene, and may also be required for packaging.

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans. For example, a plasmid or other expression vector comprising nucleotide sequences encoding one or more adenoviral proteins is transfected into a producer cell along with an rAAV vector.

An "infectious" virus or viral particle is one that comprises a competently assembled viral capsid and is capable of delivering a polynucleotide component into a cell for which the viral species is tropic. The term does not necessarily imply any replication capacity of the virus. Assays for counting infectious viral particles are described elsewhere in this disclosure and in the art. Viral infectivity can be expressed as the ratio of infectious viral particles to total viral particles. Methods of determining the ratio of infectious viral particle to total viral particle are known in the art. See, e.g., Grainger et al. (2005) Mol. Ther. 11:S337 (describing a TCID50 infectious titer assay); and Zolotukhin et al. (1999) Gene Ther. 6:973.

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

An "isolated" nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this disclosure are increasingly more isolated. An isolated nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The following example is provided to illustrate certain embodiments of the invention. It is not intended to limit the invention in any way.

EXAMPLES

Example 1

In this Example, the inventors designed and constructed a novel AAV2 vector designated ttAAV2 (as in true-type). In addition, the novel vector was tested in a number of animal models (rats, mice and neonatal mice) in order to evaluate whether ttAAV2 behaved differently as compared to the tissue culture adapted (wild type) AAV2. The inventors demonstrated that ttAAV2 has advantages for gene delivery over AAV2, and is particularly useful for in vivo transduction of brain or eye tissues with heterologous sequences.

Methods

Figure 10:
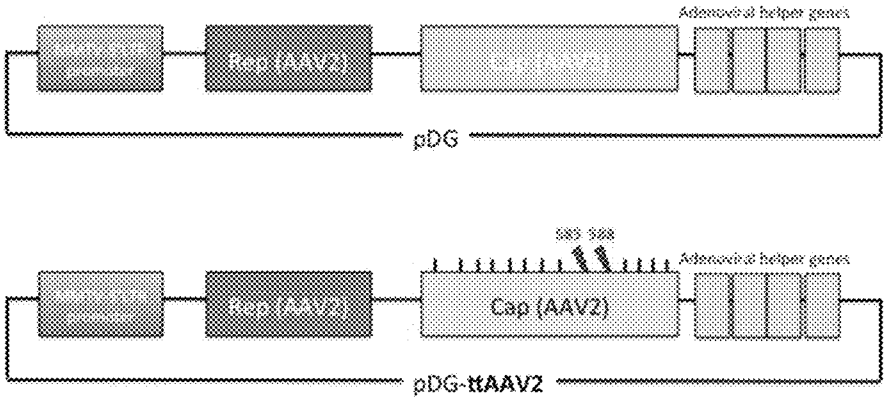
FIG. 10 The plasmid used to produce AAV2 vectors was the packaging plasmid pDG. Above: pDG with the wild-type AAV2 genes. Below: pDG-ttAAV2 with the true-type AAV2 genes, highlighted are the two key mutations in the heparan binding domains at positions 585 and 588. MMTV: promoter driving AAV rep expression, E2a, E4ORF6 and VA are the genes expressing adenovirus helper factors.

1. Cloning: The capsid gene of wtAAV2 was taken from our producer plasmid pDG (FIG. 10). This plasmid contains wtAAV2 rep and cap genes. Subfragments of the capsid gene (pDG nucleotides A:3257-3759, B:4025-4555, C:4797-5287 and D:5149-5425, respectively) were subcloned into pBS for subsequent mutagenesis. Four mutations were introduced into fragment A via site-directed mutagenesis resulting in a construct that encodes for amino acid (AA) changes V125I, V151A, A162S and T205S. Fragment B was mutated to encode the single AA change, N312S. Fragment C was mutated to encode the AA exchanges Q457M, S492A, E499D, F533Y, G546D, E548G, R585S, R588T, and A593S. Upon confirmation of successful mutagenesis fragments A-C were re-cloned into pDG, resulting in a producer plasmid (pDG-ttAAV2) that would support the production of a recombinant virus that is encapsidated by ttAAV2 capsid.

2. ttAAV2-GFP viral vector production purification and titration.

Vector production was established following the standard protocols employing co-transfection of rAAV plasmids with pDG, which provides both the Ad helper functions as well as the AAV rep and cap genes. A variety of rAAV plasmids were used to generate recombinant plasmids.

pTR-UF11 (CAG-GFP) was used as the rAAV plasmid. $8\times10^8$ 293 cells were seeded per cell factory (CF10). 14-18 hours later, the cells were transfected with pDG or pDG-rrAAV2 and prAAV (e.g. pTR-UF11) using the $CaPO_4$ co-precipitation method. After 72 hours the cells were harvested and resuspended in lysis buffer (20mMTris-HCl, pH8, 150 mM NaCl, 0.5% deoxycholate). The cell pellets were lysed by four cycles of freeze and thaw to release the virus, where each cycle consists of 30 minutes at −80° C. followed by 30 minutes at 37° C. After the last thaw the lysate was treated with benzonase at a concentration of 50 U/ml and incubated for 30 min at 37° C. The recombinant virus was purified using gravity flow columns.

Purification. As a first step, the crude lysate was clarified by centrifugation at 4000 g for 15 minutes and applied to the pre-formed iodixanol step gradient. The viral fraction was then collected and re-buffered into Lactate Ringer's solution as well as concentrated using Amicon centrifugation filters.

Subsequently, purity of the viral preparations were assessed by SDS polyacrylamide electrophoresis and titered using real time PCR methods. The crude extract contained $4.5\times10^{12}$ particles; the collected viral fractions contained $1.5\times10^{12}$ particles. At this point the purification method recovered ca. 33% of the virus present in the crude extract.

3. rAAV Vector Production and Purification (Alternative Method)

In an alternative embodiment to that at point 2 above, the rAAV2 vector is produced as follows. To produce rAAV2 virions, $5\times10^8$ 293T cells were seeded per cell factory (CF10). 14-18 hours later, the cells were double transfected with the GFP-containing vector PD10-pST2-CMV-GFP, and either the pDG or the pDG capsid mutant (pDG-ttAAV2) to produce AAV2-CMV-GFP wild-type or true-type vectors, respectively. The double transfections were realised using PEI-max from Polysciences at a ratio of 3.5 ml of PEI per mg of DNA. The cells were harvested after 72 hours of incubation at 37° C. by centrifugating the media and cells at 2200 rpm for 10 minutes at 4° C. The supernatant was removed and kept for further treatment, and the cells pellets were resuspended in lysis buffer (0.15 M NaCl, 50 mM Tris-HCl [pH 8.8]).

The cell pellets were then lysed by 4 cycles of freeze and thaw to release the virus, where each cycle consists of 30 minutes at −80° C. followed by 30 minutes at 37° C. After the last thaw the lysate was treated with benzonase at a concentration of 150 U/ml and incubated at 37° for 30 minutes. The lysate was then spun at 2000 rpm for 20 minutes to clarify the lysate. The supernatant was filtered using a 0.22 μm cellulose acetate filter and the recombinant AAV2 virus preparations were purified by FPLC using the ÄKTApurifier chromatography system (GE Healthcare) and an AVB sepharose affinity column (bfr. A: PBS, pH 8; bfr B: 0.5M glycine, pH2.7). The collected fractions were dialysed against PBS overnight and the viral preparations were then titered by SDS polyacrylamide electrophoresis and real time PCR methods.

Results

In Vivo Transduction and Spread of ttAAV2

Figure 11:
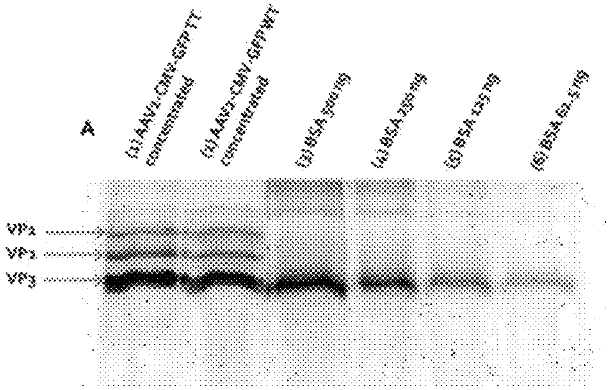
FIG. 11 Quantification of viral titres of rAAV2 true-type (TT) and wild-type (WT) for in vivo injections by SDS-PAGE showing Krypton staining for separated proteins, and scanned using an infrared-fluorescence scanner (Odyssey Imaging systems). A: 10 μl of AAV2 virus particles, and 62.5 ng-500 ng of BSA were separated on a 12% separating gel containing SDS and stained with Krypton Protein Stain. The image was converted to grayscale. The capsid gene proteins VP1, VP2, VP 3 are labelled on the left. B: Table showing titres from qPCR (vector genome [vg/ml]) and SDS-Page (capsid titre [capsid/ml]).

The ttAAV2 vector was tested in vivo in order to assess the bioactivity of the modified virus in such a context. Samples of AAV2-CMV-GFP WT and TT viruses were prepared for injections into a number of in vivo models. For this purpose we concentrated the viruses, as only limited volumes of vectors can be injected in vivo. We then performed a qPCR and SDS-PAGE to assess the new titres of the concentrated vectors (FIG. 11).

After qPCR and protein gel analysis we obtained the following new titres: AAV2-CMV-GFP TT at $1.33\times10^{12}$ viral genomes/ml and AAV2-CMV-GFP WT at $1.25\times10^{12}$ viral genomes/ml. The capsid titres were as follow: AAV2-

CMV-GFP TT at $8.89\times10^{12}$ capsids/ml and AAV2-CMV-GFP WT at $7.83\times10^{12}$ capsids/ml. The titres differ between the genome copies and the capsid copies as the SDS-PAGE also shows empty capsids, which are normally generated during recombinant AAV vectors production, hence the capsid titre is higher than the viral genome titre obtained from the qPCR.

Transduction in Rat Brain.

Figure 26:
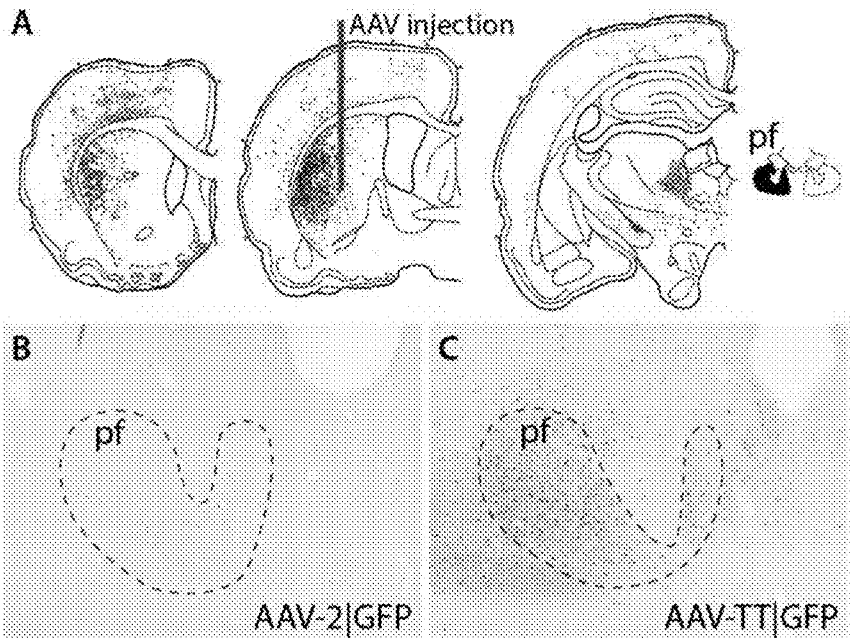
FIG. 26 Analysis of rAAV2 TT and WT expression in the parafascicularis nucleus after striatal injection in rat brain. A: Representative images of rat brain sections showing the rostral side on the left and the caudal side on the right. The site of injection in the striatum is indicated, and the area of projection in the hypothalamus observed in B and C is shown (parafascicularis nucleus, pf). B and C: High magnification images of the GFP expression detected in the parafascicularis nucleus (pf) after striatal injection of rAAV2 WT (B) or TT (C).

The rAAV2 TT and WT viruses were injected in the substantia nigra or in the striatum of wild-type rats, with 3 rats being injected per condition, at a dose of $2\times10^{9}$ vg or $3.5\times10^{9}$ vg per injection. After 28 days brains were dissected and tissue sections were prepared for immunofluorescence analysis. The primary data are shown in FIG. 12 and FIG. 26.

Both the rAAV2 TT and WT viruses were able to transduce neuronal and glial cells from each injection site, albeit with varying efficiencies. By comparison, we observed that the TT vector transduced brain tissues more efficiently and spread more from the site of injection than the WT vector. Furthermore, we observed the presence of transduced neurons in the parafascicularis nucleus, an area of the hypothalamus, after striatal injection of the rAAV2 TT. This indicates that the TT vector was able to travel from the transduced cell bodies at the site of injection to the hypothalamus by active transport along the neuron projections, highlighting a strong ability for retrograde transport. This retrograde transport ability has been lost in the tissue-culture adapted WT rAAV2 vector as no transduced cells could be observed in the same area (see FIG. 26).

Taken together, in rat brains these results indicate a significantly increased spread and transduction efficiency by ttAAV2 as compared to a titre-matched wtAAV2. Furthermore, AAV2 TT displays evidence for very good retrograde transport ability, which has been lost in the AAV2 WT virus.

Transduction in a Mouse Eye Model.

ttAAV2 and wt-AAV2 from the same batch as was used for our rat brain studies was injected into adult mouse eyes at a dose of $2\times10^{9}$ vg per eye. To avoid animal to animal variability, each mouse received an injection of rAAV2 TT in one eye and an injection of rAAV2 WT in the contralateral eye. Three different routes of intra-ocular injections were analysed: intra-cameral, intra-vitreal and sub-retinal. The animals were harvested and GFP expression was assessed by immunofluorescence after 6 weeks. The results are shown in FIG. 13. Together, these data indicate a marked enhancement of transduction of photoreceptor cells by ttAAV2 following sub-retinal injection, in terms of both level and numbers of photoreceptor cells transduced, if compared to wtAAV2 (which was used in the successful RPE65 clinical trial).

Transduction in Neonatal Mouse Model.

Figure 14:
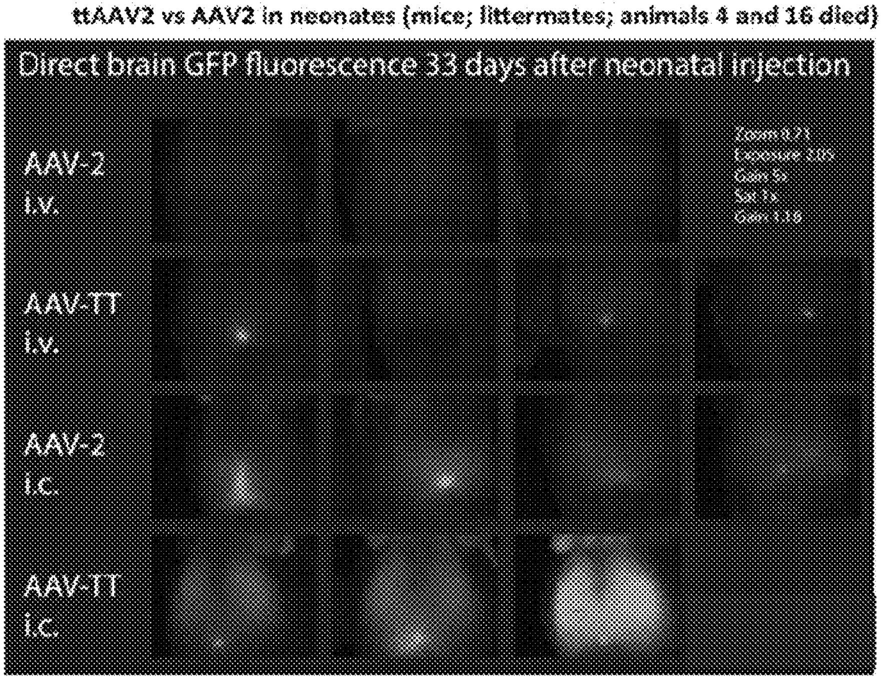
FIG. 14 Transduction of mouse brains after neonatal vector injection. i.v., intra-venous vector administration; i.c., intra-cranial injection; AAV-2, wtAAV2; AAV-TT, ttAAV2.
Figure 15:
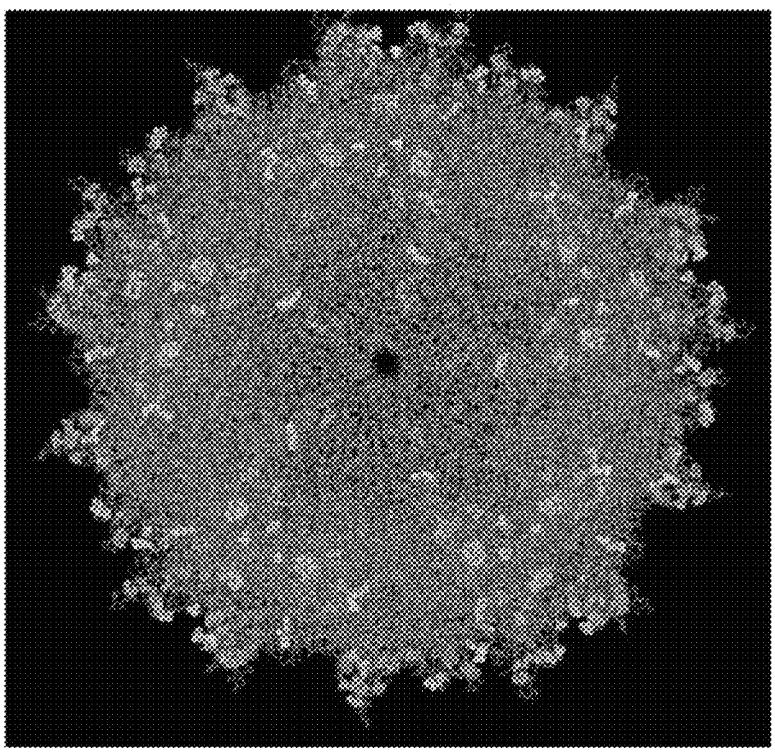
FIG. 15 Three-dimensional representation of the AAV2 capsid. The highlighted residues correspond to the amino acid changes between ttAAV2 and wild-type particles, grouped by colour depending on their position.
Figure 16:
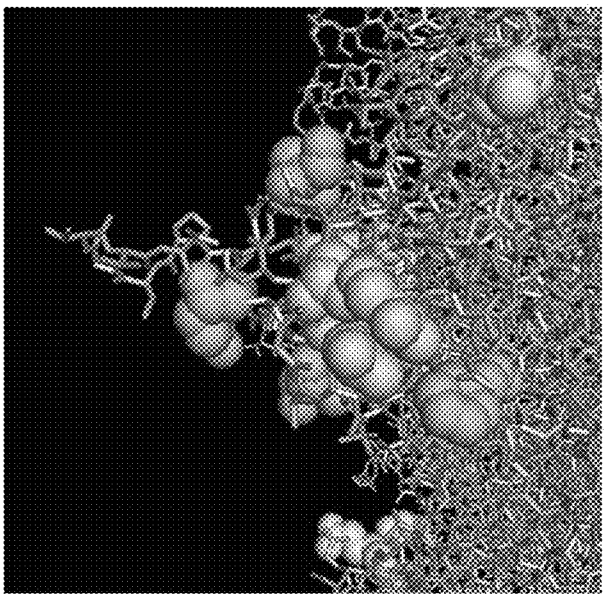
FIG. 16 Representation of a threefold spike on the AAV2 capsid. The highlighted residues correspond to the amino acid changes between True-type and Wild-type particles. The heparin binding site residues are highlighted in green.

In summary, both ttAAV2 and wtAAV2 GFP vectors were injected into mouse neonates. Two routes of injections were tested, intra-venous injection and intra-cranial injections. After 4 weeks, the animals were sacrificed and all tissues were harvested from all mice. We have analysed the brain, which after harvesting was visualised by direct fluorescence of the organ on a fluorescence microscope. The results are shown in FIG. 14. The results of intracranial and systemic injections are discussed in more detail below.

Figure 27:
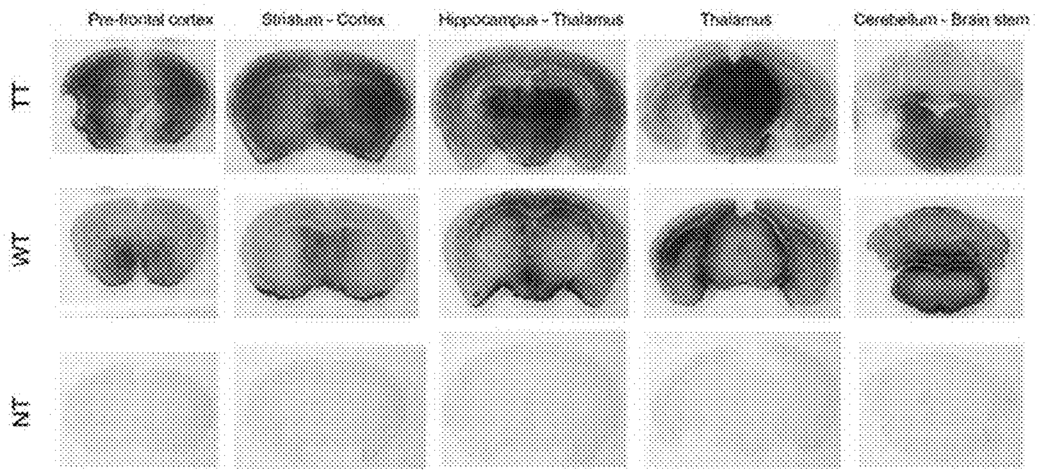
FIG. 27 Overview of intracranial injections of rAAV2 TT and WT in neonatal mice. Representative examples of neonate brain sections stained with a GFP-specific antibody are shown. $5\times10^{10}$ vg of rAAV2 TT (top) or rAAV2 WT (middle) were injected into the lateral ventricle of neonatal mouse brains. An uninjected brain from a neonatal mouse, stained simultaneously, is represented as a negative control (NT, non transduced).

Intracranial Injections $5\times10^{10}$ vg of either vector were injected in the lateral ventricle of P1 neonates. The animals were sacrificed 4 weeks post-injection and the brains were dissected, sectioned and stained using an anti-GFP antibody. The results are shown in FIG. 27.

Figure 28:
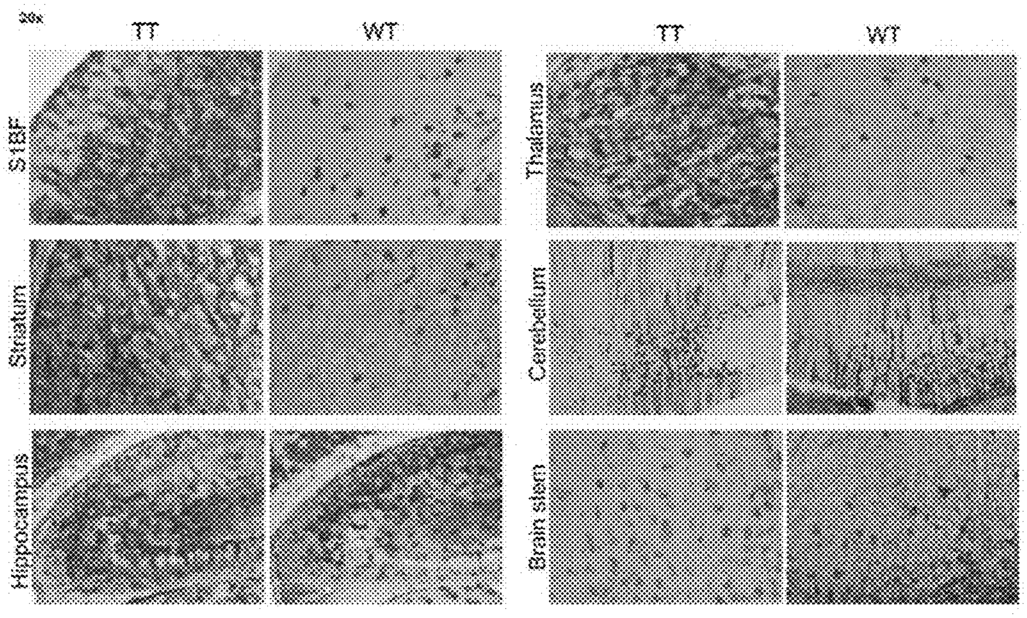
FIG. 28 High magnification pictures of neonatal mouse brain sections after intracranial injections of rAAV2 TT or WT. Neonate brain sections stained with a GFP-specific antibody are shown. $5\times10^{10}$ vg of rAAV2 TT (left panels) or rAAV2 WT (right panels) were injected into the lateral ventricle of neonatal mouse brains. S1BF: barrel field primary somatosensory cortex.

As observed in adult rat brains, these data indicate that AAV2 TT displays enhanced transduction of mouse brain tissues and higher spread after intracranial injection as compared to the AAV2 WT vector. When observing the stained sections at a higher magnification, the differences in transduction efficiency between both vectors were further highlighted: the TT vector performed better both in terms of level of expression and of number of cells transduced. AAV2 TT and WT seem to have the same cell type affinity, each displaying transduction of neuronal as well as glial cells, suggesting that the differences observed are differences in efficiency rather than in cell-type specificity (FIG. 28).Taken together these data indicate that ttAAV2 shows much enhanced transduction of mouse brain tissues after i.c. injection as compared to wtAAV2-based vectors. In addition, some evidence is suggestive for transduction of the ependymal cell layer lining the ventricles when ttAAV2 vectors are used. This phenomenon is not visible with the wtAAV2 vector.

Systemic Injections

Figure 29:
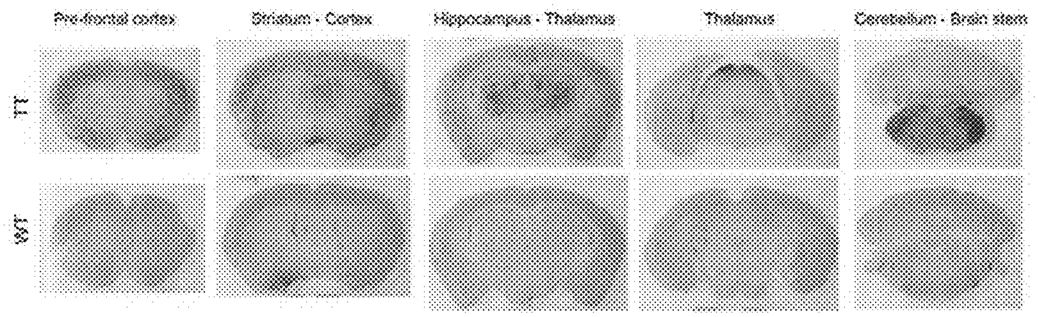
FIG. 29 Overview of brain transduction after systemic injection of rAAV2 TT and WT in neonatal mice. Representative examples of neonate brain sections stained with a GFP-specific antibody are shown. $2\times10^{11}$ vg of rAAV2 TT (top) or rAAV2 WT (bottom) were injected into the jugular veins of neonatal mice.
Figure 30:
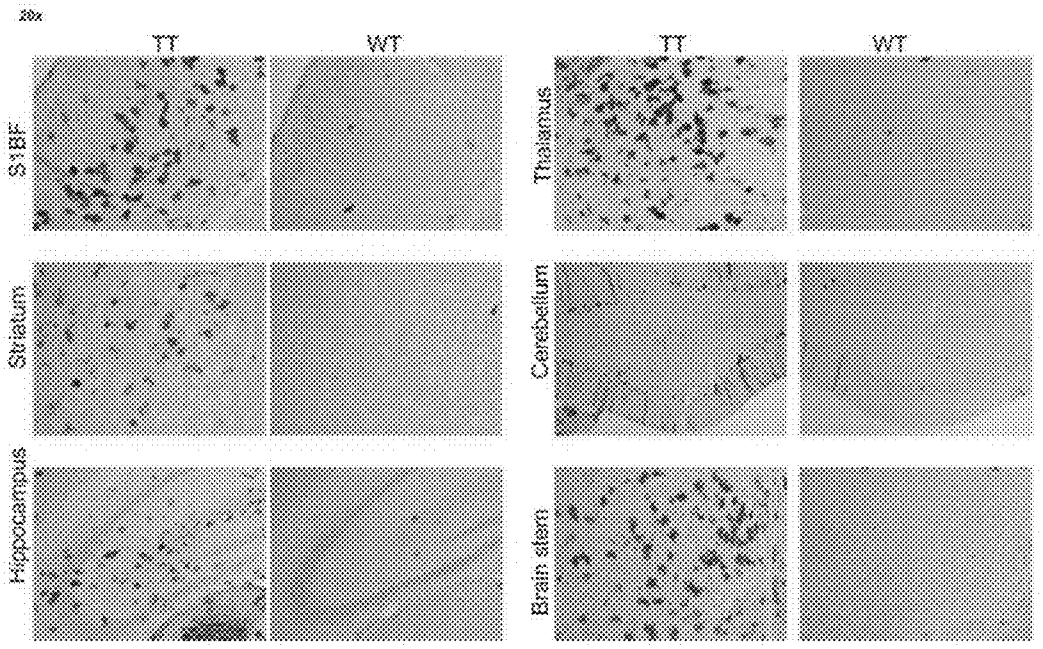
FIG. 30 High magnification pictures of neonatal mouse brain sections after systemic injections of rAAV2 TT or WT. Neonate brain sections stained with a GFP-specific antibody are shown. $2\times10^{11}$ vg of rAAV2 TT (left panels) or rAAV2 WT (right panels) were injected into the jugular veins of neonatal mice. S1BF: barrel field primary somatosensory cortex.

Intrajugular injections of $2\times10^{11}$ vg of either vector were done in P1 neonates. The animals were sacrificed 4 weeks post-injection and various organs were harvested and assessed for GFP transduction by immunohistochemistry using an anti-GFP antibody (brain, liver, heart, muscle, lungs, spleen and kidney). Results of the brains staining are shown in FIG. 29 and high magnification pictures are presented in FIG. 30.

We observed good transgene expression in the CNS after systemic injection of AAV2 TT. The AAV2 WT vector performed worse in comparison, with only few transduced neurons observed.

Figure 31:
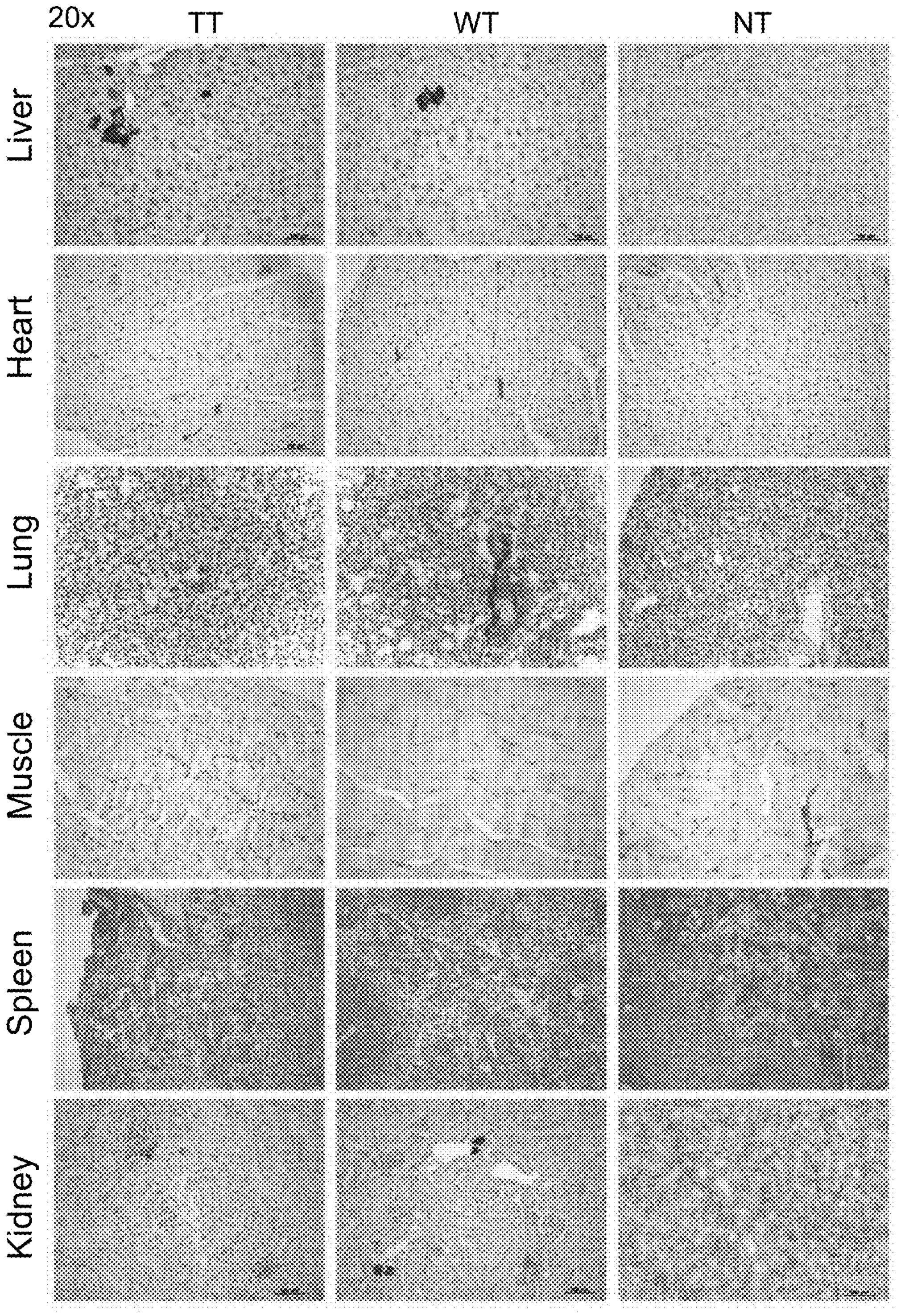
FIG. 31 High magnification pictures of neonatal mouse tissue sections after systemic injections of rAAV2 TT or WT. $2\times10^{11}$ vg of rAAV2 TT or rAAV2 WT were injected into the jugular veins of neonatal mice. Uninjected mouse organs were used as negative controls.

In order to assess the overall biodistribution of the AAV2 TT vector we assessed the level of transduction obtained in various tissues after systemic injection. The harvested organs were fixed, paraffin embedded, sectioned and stained for GFP expression (FIG. 31).

These data indicate that the AAV-TT vector doesn't seem to have a strong affinity for other organs but instead displays specificity mainly for neuronal tissues. This observation could prove beneficial for the treatment of neuronal genetic disorders by intravenous injections of AAV as it ensures that the vector will not transduce non-target peripheral organs but mainly only the brain via this injection route.

Together, our in vivo data suggests that ttAAV2 has extraordinary transduction characteristics in eye and brain tissues, displaying specificity for neuronal tissues almost exclusively.

Example 2

Additional Considerations

Without being bound by theory, it is believed that the mutations present in ttAAV2 compared to wtAAV2 comprise the following functional groups:

1) heparin binding residues located on the AAV2 capsid threefold spikes (S585 and T588); it is believed that these residues are responsible for heparin binding of the wtAAV2 capsid. In ttAAV2 these are replaced and we assume that this replacement supports the spread of the virus in heparan sulphate proteoglycan-rich brain tissue.

2) the single amino acid change in ttAAV2 that is located on the internal side of the capsid (S312); this internal serine residue might play a role in capsid-DNA interactions, thereby potentially contributing to, either virus stability, genome packaging or genome release during infection.

3) two spatially close amino acids (D546 and G548) located in the groove between the threefold-proximal spikes on AAV capsid structure; these residues might be involved in interactions with neutralizing antibodies and thus contribute to in vivo transduction characteristics.

4) a single isolated amino acid change (S593) located in the groove between threefold-proximal spikes;

5) four amino acids believed to be involved in receptor binding and closely situated on the threefold spikes (M457, A492, D499 and Y533);

6) the four remaining amino acid changes situated in VP1/VP2 primary sequence (1125, A151, S162 and S205); these residues are within the capsid region that is not part of VP3. It is known that VP1/VP2 specific regions within the virus capsid contain PLA2 activity which might be involved in trafficking of the incoming virus. Changes in this region have been shown to influence viral infectivity.

The three-dimensional positions of these mutations in the AAV2 capsid protein are known and are shown in FIGS. 15 to 20. Corresponding positions can be identified in the AAV capsid proteins from other serotypes (see below). To further characterize the ttAAV2 and the role of individual amino acid changes that are responsible for the improved ttAAV2 phenotype, the ttAAV2 capsid can be mutated in order to reverse individual chosen amino acids (or groups of amino acids, e.g. based on groups 1 to 6 discussed above) to their corresponding sequence in the wild-type AAV2 capsid. Each mutant vector can then be analysed using methods as described in the examples above.

For instance the various mutant vectors, expressing GFP, can be submitted to a first screen in an animal model by intracranial (IC) injection in CD1 neonatal mice. The GFP signal obtained in the injected brains from each mutant vector is then observed by fluorescence microscopy and compared to that obtained from the original GFP-expressing wtAAV2 and ttAAV2 vectors. Upon identification of a new phenotype (i.e. the abolition of the ttAAV2-specific strong GFP expression when mutating a particular amino acid group), the injected brains are then further sectioned and analysed by immunohistochemistry.

In parallel, these selected mutant vectors are submitted to a second screen by adult rat intracranial injections. Additionally, relevant mutant combinations are analysed by intravenous (IV) injections into neonatal mice in order to evaluate the biodistribution of the vectors. Selected organs (heart, lung, liver, spleen, kidney, muscle) are then processed for immunohistochemistry and evaluation of GFP expression.

Analysis of the contribution of each TT-specific residue to the efficiency and biodistribution of the vector To further characterize the AAV2 TT and pinpoint the amino acid changes that are responsible for the improved TT phenotype, the AAV2 TT capsid was mutated step by step in order to reverse the chosen amino acids to their corresponding sequence in the wild-type AAV2 capsid. This strategy enabled us to discern more specifically the contribution of each of the 14 amino acid mutations towards the phenotype of AAV2 TT and to define a minimal true-type vector, containing only the necessary mutations.

As discussed above, we grouped the 14 TT-specific residues into groups based on their positions on the AAV capsid and their associated potential contributions to the transduction profile. The various AAV-TT mutants were screened by intracranial injections in neonatal mouse brains or in adult rat brains in order to observe whether the reversion of some TT-specific residues to the WT equivalents was associated with a loss of phenotype, thereby identifying the important amino acid changes amongst the 14 TT residues.

The Heparin Binding Site (HBS)

It has been shown that residues 585 and 588 are responsible for heparin binding of the AAV2 WT capsid. In AAV-TT these are replaced and we assumed that this replacement support the spread of the virus in heparin sulphate proteoglycan-rich brain tissue. These two residues are situated on the three-fold proximal spikes of the AAV2 capsid structure (see FIG. 16).

We abolished the AAV2 WT heparin binding ability by engineering the changes R585S and R588T on the WT capsid (AAV2-HBnull), i.e. mutating the residues to the true-type equivalents. This first analysis was performed in order to ascertain that AAV-TT was not merely an AAV2 without heparin binding site, able to spread more, but that some of the other 12 amino acid changes also play a role in the improved AAV-TT transduction profile.

Intracranial Injections in Adult Rat

Figure 32:
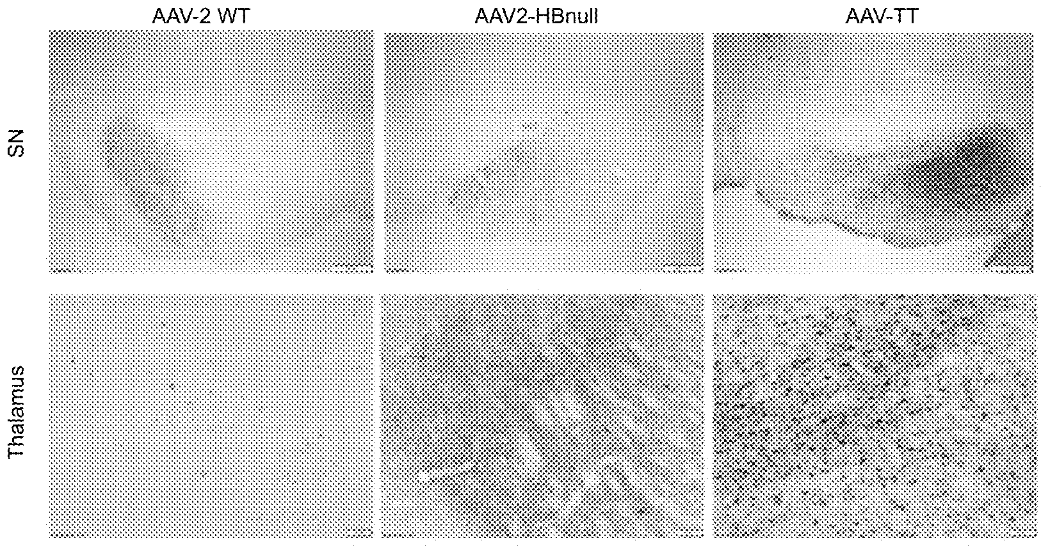
FIG. 32 High magnification images of adult rat brain sections after striatal injections of rAAV2 TT, WT and HBnull. Representative examples of rat brain sections stained with a GFP-specific antibody are shown. $3.5\times10^{9}$ vg of rAAV2 WT (left), TT (right) or AAV2-HBnull (middle) were injected into the striatum of adult rat brains and representative pictures were taken in the thalamus or in the substantia nigra (SN).

Titer-matched AAV2-TT, AAV2-WT and AAV2-HBnull vectors were injected in the substantia nigra or in the striatum of wild-type rats at a dose of $3.5\times10^9$ vg per injection. After 28 days brains were dissected and tissue sections were prepared for immunohistochemistry analysis of GFP expression (FIG. 32).

We observed a strong GFP expression in the thalamus and in the substantia nigra after striatum injection of AAV-TT virus, highlighting the strong retrograde transport ability of the vector. In comparison, AAV2-HBnull and AAV2 WT displayed much less—if any—retrograde transport than AAV-TT as very few cell bodies were transduced in these area after striatal injections. This observation showed that AAV2-HBnull is different to AAV-TT and that the absence of heparin binding ability on the AAV2 capsid contributes to the good spread of the true-type vector in the brain. However it is not sufficient to explain its improved transduction profile.

The Residues S312, D546-G548 and S593

The S312 residue is the only TT-specific change that is located on the internal side of the AAV2 capsid. Our assumption was that this internal residue might play a role in capsid-DNA interactions, thereby potentially contributing to either virus stability, genome packaging or genome release during infection.

The D and G residues at positions 546 and 548, respectively, are located in the groove between the proximal 3-fold peaks.

A single isolated serine, S593, is situated in the groove between threefold-proximal spikes.

Figure 17:
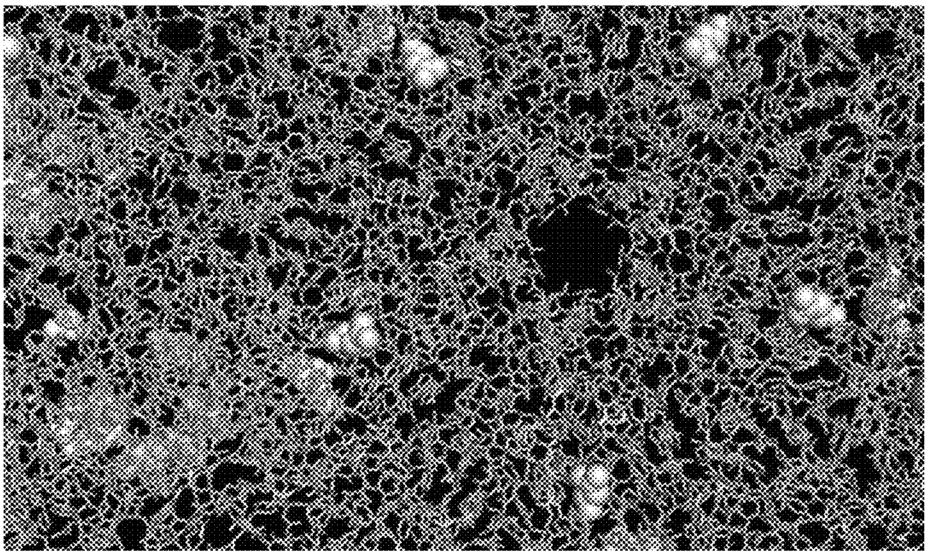
FIG. 17 Representation of the internal side of the AAV2 capsid. The highlighted residues in light-blue correspond to the single amino acid change in ttAAV2 that is located on the internal side of the capsid.
Figure 18:
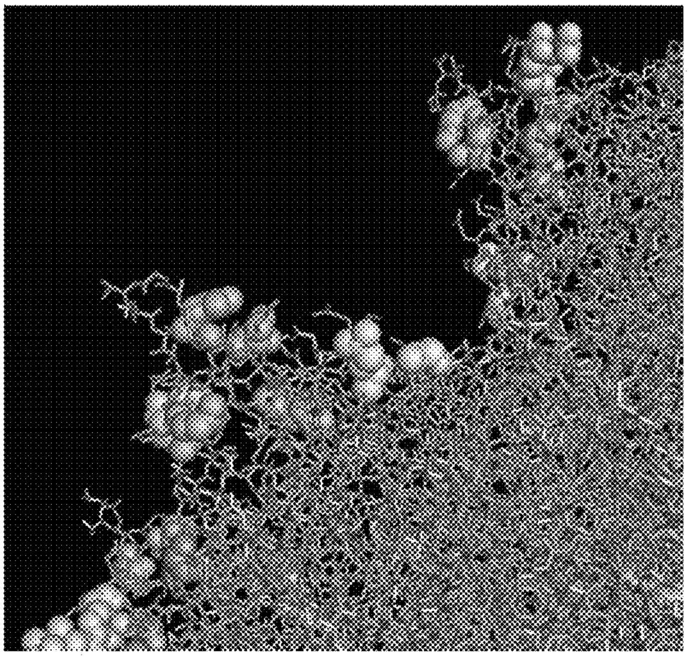
FIG. 18 Representation of a threefold spike on the AAV2 capsid. The residues highlighted in beige correspond to two amino acid changes in the True-type vector that are spatially close and located in the groove between two threefold-proximal peaks on the AAV capsid.
Figure 19:
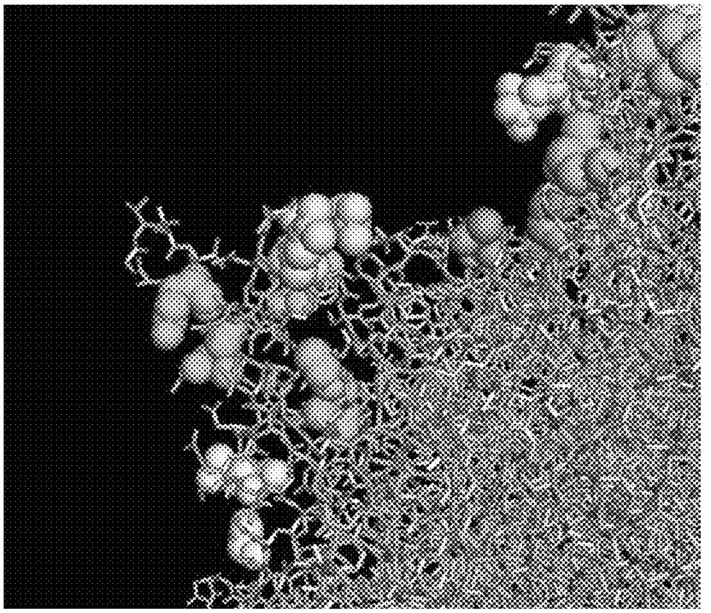
FIG. 19 Representation of a threefold spike on the AAV2 capsid. The residue highlighted in brown corresponds to a single isolated amino acid change (S593) in the True-type vector that is located in the groove between threefold-proximal peaks FIG. 20 Representation of a threefold spike on the AAV2 capsid. The four amino acids highlighted in pink are involved in receptor binding and closely situated on the threefold spikes.
Figure 20:
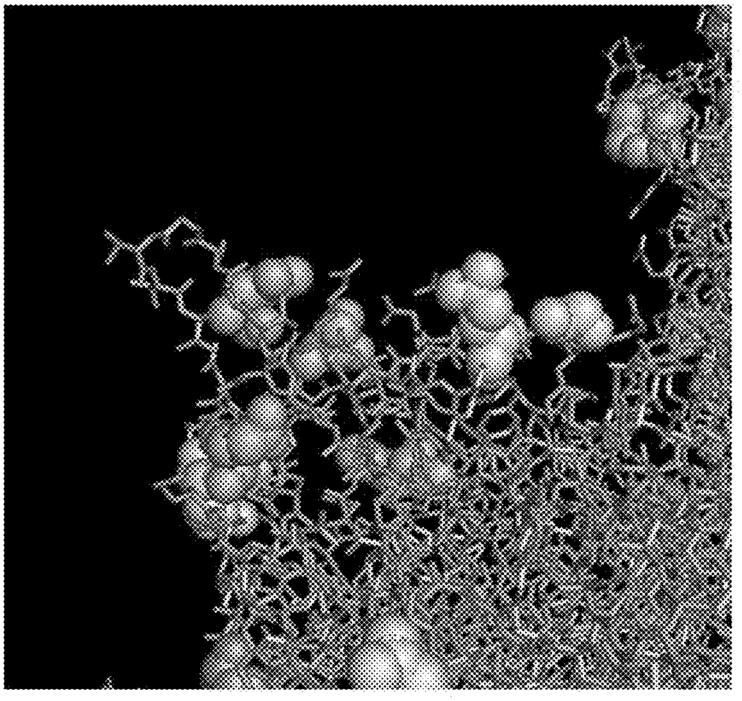

The positions of these TT-specific residues on the three-dimensional structure of the AAV2 capsid are presented in FIGS. 17 to 19. Given their less prominent position in the structure we hypothesised that these residues might not contribute to the ttAAV2 transduction phenotype.

Neonatal Mice Intracranial Injections

The mutation S312N was engineered on the AAV2-TT capsid to create the TT-S312N mutant. The mutations D546G and G548E were engineered on the AAV2-TT capsid to generate the AAV-TT-DG mutant. The mutation S593A was engineered on the AAV2-TT capsid to create the AAV-TT-S593A mutant.

By reverting these chosen TT amino acids to their corresponding sequence in the wild-type AAV2 capsid we aimed to determine the contribution of these residues to the improved AAV-TT phenotype.

Figure 33:
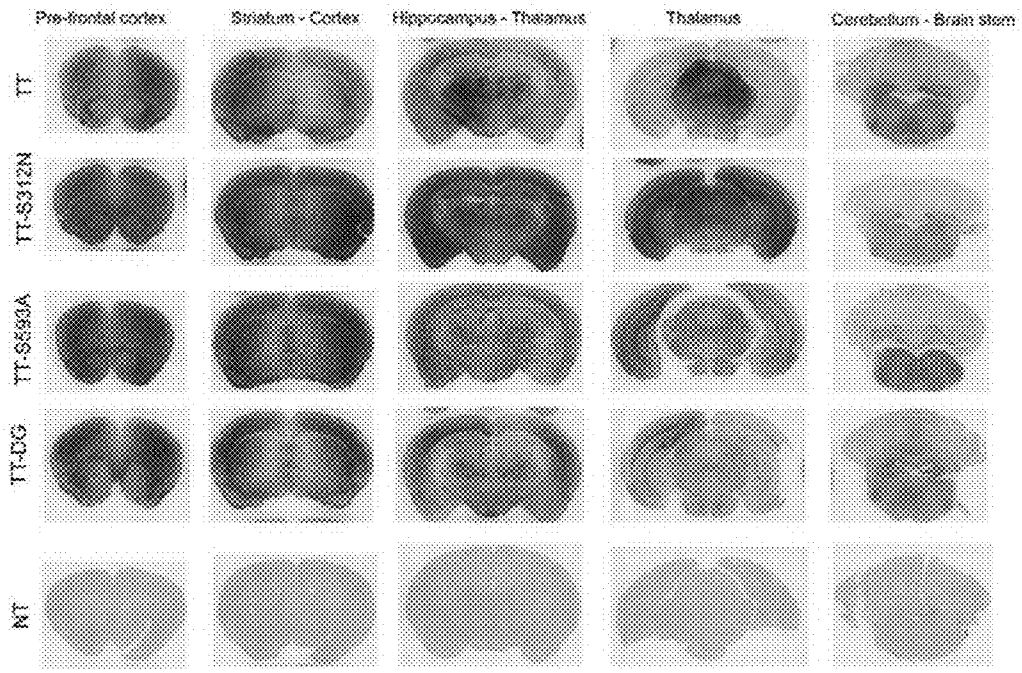
FIG. 33 Overview of intracranial injections of the full AAV-TT compared with various TT mutants in neonatal mice. Representative examples of neonate brain sections stained with a GFP-specific antibody are shown. $5\times10^{10}$ vg of rAAV2 TT, TT-S312N, TT-S593A or TT-D546G/G548E (TT-DG) were injected into the lateral ventricle of neonatal mouse brains. An uninjected brain from a neonatal mouse, stained simultaneously, is represented as a negative control (NT).

$5\times10^{10}$ vg of each mutant vector were injected in the lateral ventricle of P1 neonates. The animals were sacrificed 4 weeks post-injection and the brains were dissected, sectioned and stained using an anti-GFP antibody. The results are shown in FIG. 33.

Figure 34:
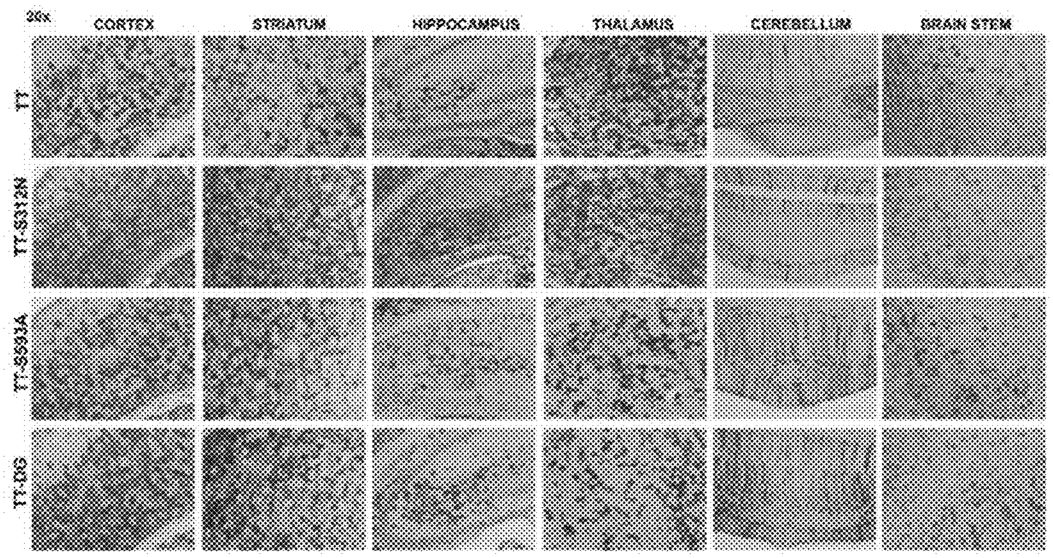
FIG. 34 High magnification pictures of neonatal mouse brain sections after intracranial injections of various TT mutant vectors. Neonate brain sections stained with a GFP-specific antibody are shown. $5\times10^{10}$ vg of vectors were injected into the lateral ventricle of neonatal mouse brains. TT-DG: TT-D546G/G548E.

Interestingly, these data suggest that the AAV TT-S312N displays enhanced transduction of mouse brain tissues as compared to the full AAV2 TT vector. On the other hand, the amino acid changes S593A or D546E/G548D did not seem to affect the TT phenotype as similar transduction profiles could be observed throughout the brains. When observing the stained sections at a higher magnification, the differences in transduction efficiency were further highlighted (FIG. 34).

From the high magnification pictures, we could observe that the AAV TT-S312 seems to transduce neuronal tissues with higher efficiency than the original AAV-TT with 14 amino acid changes. In particular, we could see stronger transgene expression in the rostral side of the brain (cortex, striatum, hippocampus) after TT-S312N vector injection, both in terms of level and of number of cells transduced. Despite the high variability in injected neonatal brains due to the difficulty associated with targeting the injection site, this observation was confirmed in all the animals analysed. On the other hand, the reversions S593A or D546E/G548D did not seem to have much impact on the TT vector transduction phenotype.

Example 3

Targeted Amino Acid Mutations on the AAV2 True-Type Capsid, Selected from Results Obtained with the Mutant Combinations in Example 2

Based on the results from amino acid group mutations on the full AAV TT capsid, we could determine that the mutation S312N seems to be beneficial for the TT phenotype, further increasing its transduction efficiency in the brain. Furthermore, we observed that the reversions S593A and D546G/G548E did not seem to affect the neuronal phenotype of AAV-TT. We therefore hypothesised that the TT-specific residues S593, D546 and G548 could be excluded from the True-type capsid sequence, leaving instead the AAV2 WT residues at these positions to obtain a final TT vector with only 10 amino acid changes.

In order to verify these hypotheses, we engineered the TT-S312N-D546G-G548D-S593A vector and tested its transduction efficiency by neonatal mouse brain injections. Because the last neonate intracranial injections seemed to lead to a saturated signal in the GFP expression detected, we decided to also inject the TT and the TT-S312N vectors alongside this "pre-final" TT, using a 10 times lower dose than used previously. By using this lower dose we aimed to avoid reaching saturating levels of GFP staining in the transduced brains and avoid difficulties in transduction efficiency comparison between different mutants.

Figure 35:
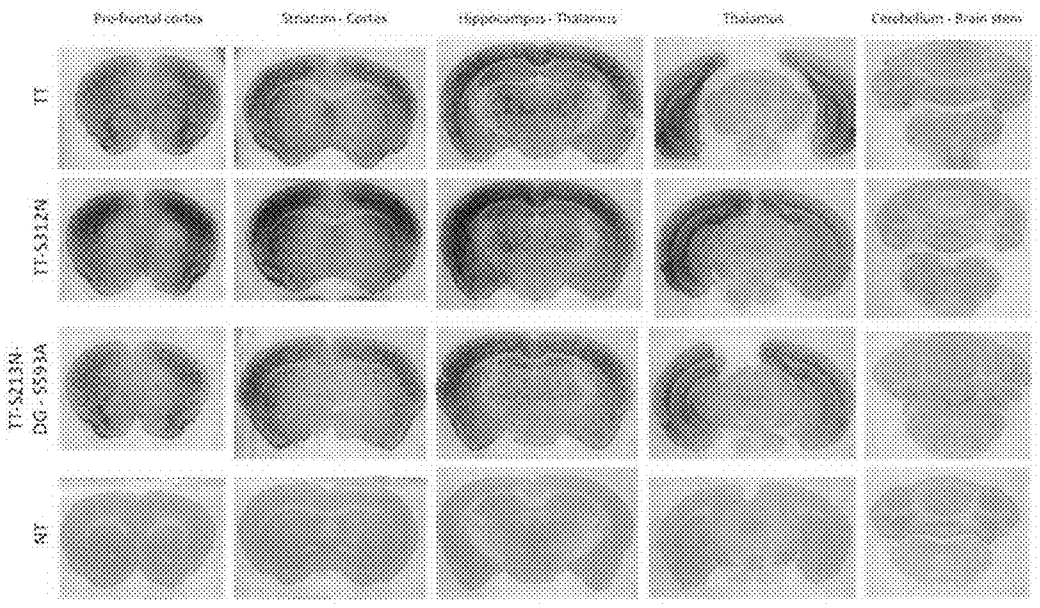
FIG. 35 Overview of neonatal mice intracranial injections of the full AAV-TT compared with the TT-S312N mutant and the potential final TT vector containing 10 mutations. Representative examples of neonate brain sections stained with a GFP-specific antibody are shown. $5\times10^{09}$ vg of rAAV2 TT, TT-S312N, TT or TT-S312N-D546G/G548E-S593A (TT-S312N-DG-S593A) were injected into the lateral ventricle of neonatal mouse brains. An uninjected brain from a neonatal mouse, stained simultaneously, is represented as a negative control (NT).

$5\times10^{09}$ vg of each mutant vector were injected in the lateral ventricle of P1 neonates. The animals were sacrificed 4 weeks post-injection and the brains were dissected, sectioned and stained using an anti-GFP antibody. The results are shown in FIG. 35.

Figure 36:
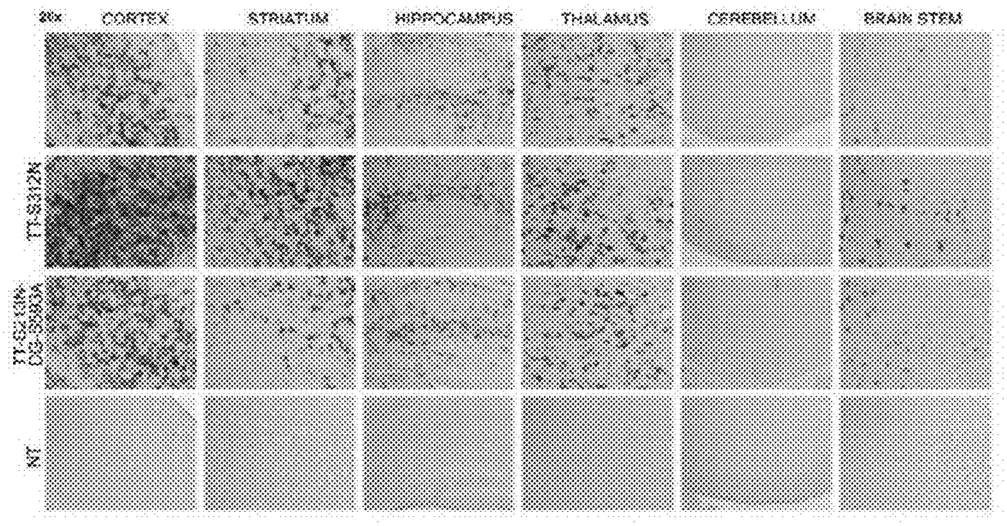
FIG. 36 High magnification pictures of neonatal mouse brain sections after intracranial injections of various TT mutant vectors. Neonate brain sections stained with a GFP-specific antibody are shown. $5\times10^{09}$ vg of vectors were injected into the lateral ventricle of neonatal mouse brains.

As previously observed, these data suggest that the AAV TT-S312N displays enhanced transduction of mouse brain tissues as compared to the full AAV2 TT vector. On the other hand, the minimal TT-S312N-D546G/G548E-S593A vector did not seem to reach these higher levels of transduction even though it also contained the internal S312N mutation. This suggests that one or more of the amino acid changes plays some role in the TT phenotype. By reverting these residues back to AAV2 WT equivalents, we lost some of the increased transduction ability. When observing the stained sections at a higher magnification, these observations were confirmed (FIG. 36).

Figure 37:
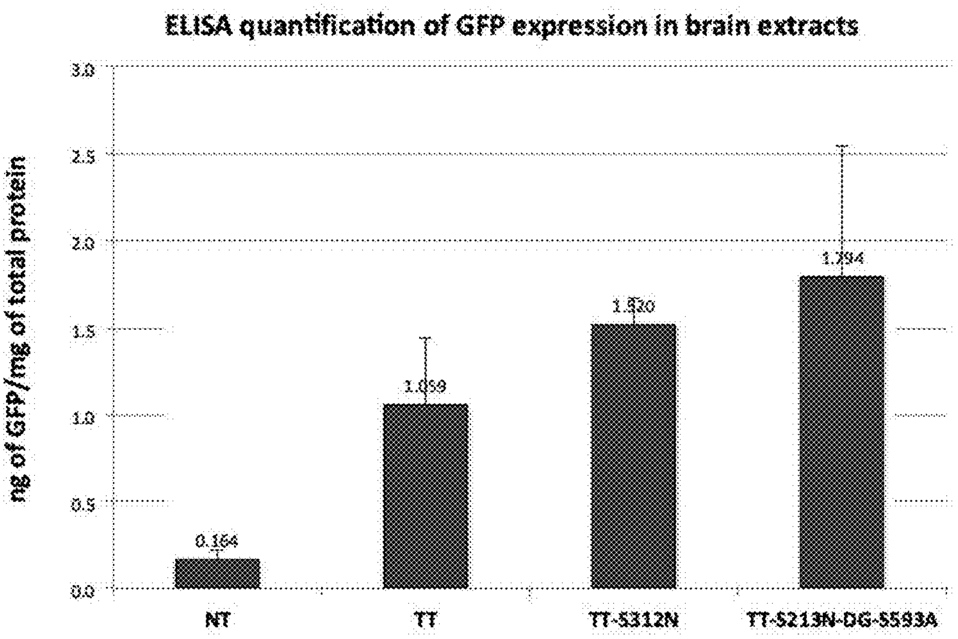
FIG. 37 ELISA quantification of GFP protein in neonatal mice brains injected with the full AAV-TT, the TT-S312N mutant or the TT-S312N-DG-S593A. $5\times10^{09}$ vg of vectors were injected into the lateral ventricle of neonatal mouse brains and total proteins were extracted from whole harvested brains. A GFP-specific antibody was used to detect the GFP expression in each brain sample and a standard GFP protein was used for quantification. N=5 animals per condition. Error bars represent the mean±SEM FIG. 38 Amino acid sequence of the VP1 capsid protein of AAV3B. The highlighted residues represent the residues that are identical to the ones in AAV-tt at corresponding positions. The internal serine residue at position 312 is underlined.

We decided to further investigate the transduction efficiency obtained by each of these vectors by quantifying the total GFP expression obtained in injected brains by enzyme-linked immunosorbent assay (ELISA) on full brain protein extracts. Briefly, 4 weeks after injection of $5\times10^{09}$ vg of vectors, the animals were sacrificed, the whole brains were harvest and lysed, and total brain proteins were extracted. Using a GFP protein standard, we could then quantify the amounts of GFP protein expressed in each injected brain (FIG. 37).

We could confirm that the TT-S312N internal mutant transduces mouse brains with more efficiency than the full TT vector as it leads to more GFP expression overall in all the injected brains. On the other hand the minimal TT vector, TT-S312N-D546G/G548E-S593A, seemed to lead to lower levels of transduction: although the average amount of GFP expressed per brain seems higher on this graph, this was due to extreme GFP values measured in one of the brains as illustrated by the high error bar for this condition. With this minimal TT vector, the variability between animals was very high, with only one animal out of five performing better than the animals transduced with TT-S312N. This high variability led us to consider this provisional minimal TT vector with caution, especially since the immunohistochemistry analyses also showed that the TT-S312N variant performed better than the TT-S312N-DG-S593A.

We therefore selected the TT-S312N variant as our most preferred AAV TT vector, which is composed of the following 13 amino acid mutations compared to the wild-type AAV2: V125I, V151A, A162S, T205S, Q457M, S492A, E499D, F533Y, G546D, E548G, R585S, R588T, and A593S.

Although the above studies suggest the TT-S312N as the most preferred AAV-TT vector, these studies illustrate the individual function and contribution of a number TT-specific residues. In particular, four amino acids closely situated on the threefold spike of the capsid are likely involved in receptor binding. In some embodiments, these residues are reverted in the AAV-TT back to the AAV2 WT corresponding residues. For instance, the mutations M457Q, A492S, D499E and Y533F may be engineered on the AAV-TT capsid and this mutant vector analysed as previously described, in order to illustrate the role of these residues. In further embodiments, four amino acids situated in VP1/VP2 primary sequence, which are likely to be involved in trafficking of the virus, may be reverted in the AAV-TT back to AAV2 WT corresponding residues (I125V, A151V, S162A, S205T) and analysed similarly.

Example 4

Construction of Variant AAV Vectors in Other Serotypes

The function of the ttAAV2-specific amino acid changes in the context of other, non-AAV2 serotypes can also be determined.

The capsid amino acid sequences of the main adeno-associated viruses (AAV), namely AAV1, 5, 6, 8, 9 and rh10, can be aligned with the one from ttAAV2, e.g. as shown in FIG. 9. This enables the identification of which ttAAV2-specific amino acids are already present at the same positions in other serotypes. The relevant residues in the various serotypes are then mutated into the corresponding residues in wtAAV2. These changes demonstrate the importance of the ttAAV2-specific residues for the efficiency and biodistribution of each of the serotype.

As discussed above, the various mutant vectors, expressing GFP, are then submitted to a first screen by intracranial (IC) injection in CD1 neonatal mice. The GFP signal obtained in the injected brains is then compared to that obtained from the appropriate GFP-expressing serotype controls. The diminution or increase of GFP expression when mutating the identified amino acids into their corresponding AAV2 residues demonstrates the importance of these particular residues at these specific positions. Where applicable, the injected brains are then further sectioned and analyzed by immunohistochemistry. Additionally, chosen mutant serotypes are analyzed by intravenous (IV) injections into neonatal mice in order to evaluate the biodistribution of the vectors and compare it to the original, non-mutated counterparts.

In further embodiments, the relevant amino acids identified in the ttAAV2 are inserted as key mutations into the other prominent serotypes at the relevant positions. The insertion of ttAAV2-specific residues in other AAV subtypes enables us to improve the transduction and biodistribution profiles of each serotype.

Example 5

Modification of ttAAV2-Specific Residues Conserved in Other AAV Serotypes into the Corresponding AAV2 Residues.

A comparative analysis of the capsid amino acid sequences of existing adeno-associated serotypes with the one from ttAAV2 first enabled us to identify ttAAV2-specific residues that are conserved in other serotypes (see FIG. 9). These residues consist of S162, S205, S312, G548, S585 and T588. Each non-AAV2 serotype contains one or a combination of several of these residues at a corresponding amino acid position in its sequence.

In specific embodiments, each of these residues in the various serotypes are converted into the corresponding wild-type AAV2 amino-acid(s) and the transduction efficiency of these new mutants is tested.

1) Modification of the AAV1 Serotype

Figure 21:
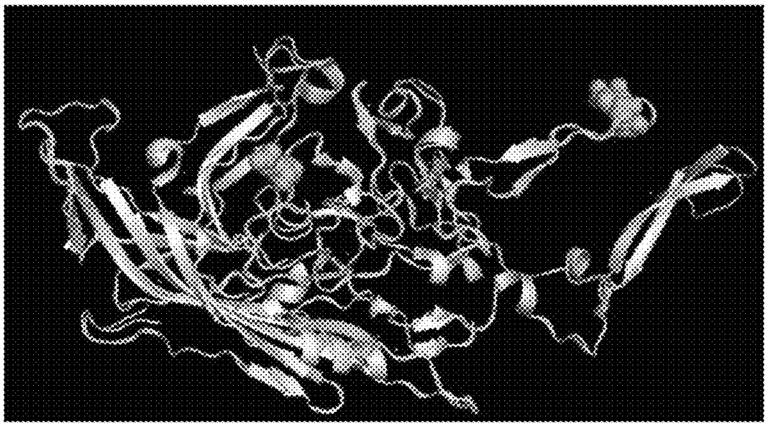
FIG. 21 Three-dimensional representation of an alignment between VP1 capid monomer from AAV2 (light blue) and VP1 monomer from AAV1 (orange). The highlighted residues in the middle-left of the picture correspond to G549 in AAV1 (orange spheres) and E548 in AAV2 (cyan sphere). The highlighted residues in the top-right of the picture correspond to S586 and T589 in AAV1 (orange spheres) and R585 and R588 in AAV2 (cyan sphere).
Figure 22:
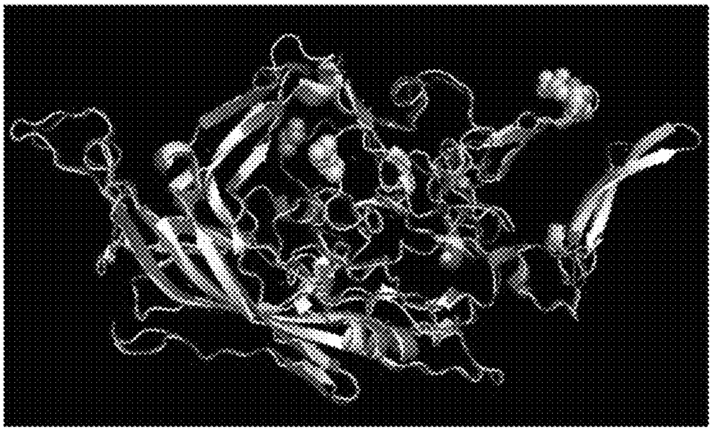
FIG. 22 Three-dimensional representation of an alignment between VP1 capsid monomer from AAV2 (light blue) and VP1 monomer from AAV5 (purple). The highlighted residues in the middle of the picture correspond to G537 in AAV5 (purple spheres) and E548 in AAV2 (cyan sphere). The highlighted residues in the top-right of the picture correspond to 5575 and T578 in AAV5 (purple spheres) and R585 and R588 in AAV2 (cyan sphere).
Figure 23:
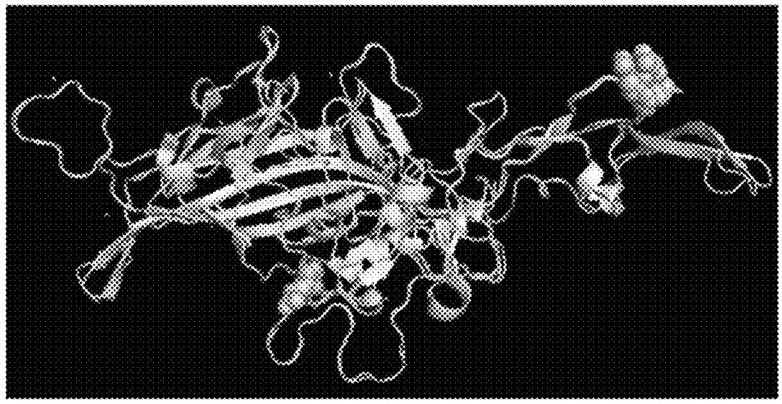
FIG. 23 Three-dimensional representation of an alignment between VP1 capsid monomer from AAV2 (light blue) and VP1 monomer from AAV6 (yellow). The highlighted residues in the bottom of the picture correspond to G549 in AAV6 (orange spheres) and E548 in AAV2 (cyan sphere). The highlighted residues in the top-right of the picture correspond to S586 and T589 in AAV6 (orange spheres) and R585 and R588 in AAV2 (cyan sphere).

AAV1 contains the residues S205, G549, S586 and T589 which correspond to the following residues in ttAAV2: S205, G548, S585 and T588. When the VP1 monomer from AAV1 was aligned three-dimensionally with VP1 from AAV2 we could verify that the corresponding residues in wtAAV2, namely T205, E548, R585 and R588, are at perfectly matching positions on the 3D structure (FIG. 21). We thus concluded that it would be significant to convert each of the ttAAV2-specific residue(s) in AAV1 into the corresponding wild-type AAV2 counterparts without affecting the three-dimensional structure of the protein. In particular embodiments the following mutations are made in AAV1 capsid sequence: S205T, G549E, S586R, T589R.

2) Modification of the AAV5 Serotype

AAV5 contains the residues G537, S575 and T578 which correspond to the following residues in ttAAV2: G548, S585 and T588. The R585 and R588 residues in AAV2 are at matching positions with S575 and T578 in AAV5 on the 3D structure. Although the residue E548 in AAV2 did not perfectly match the residue G537 in AAV5 according to the three-dimensional structure (FIG. 22), we still decided to include it in the study as both residues are relatively spatially close. Therefore in particular embodiments the following mutations are made in AAV5 capsid sequence: G537E, S575R, T578R.

3) Modification of the AAV6 Serotype

AAV6 contains the residues S205, G549, S586 and T589 which correspond to the following residues in ttAAV2: S205, G548, S585 and T588. The corresponding residues in wtAAV2, namely T205, E548, R585 and R588 (FIG. 23), are at perfectly matching positions on the VP1 3D structures. Therefore in particular embodiments the following mutations are made in AAV6 capsid sequence: S205T, G549E, S586R, T589R.

4) Modification of the AAV8 Serotype

Figure 24:
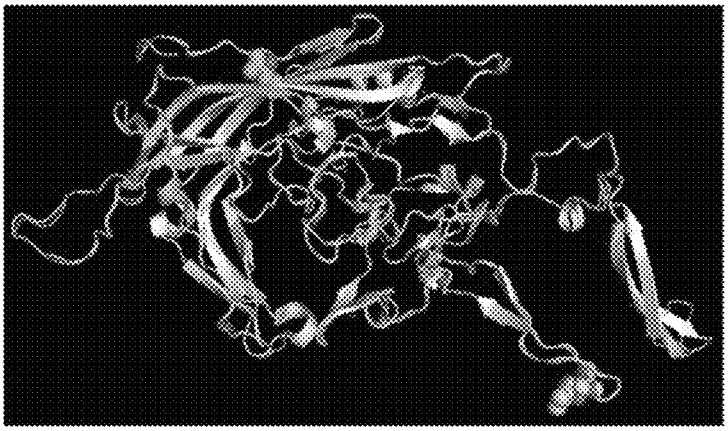
FIG. 24 Three-dimensional representation of an alignment between VP1 capsid monomer from AAV2 (light blue) and VP1 monomer from AAV8 (pink). The highlighted residues in the top-left of the picture correspond to S315 in AAV8 (red spheres) and N312 in AAV2 (cyan sphere). The highlighted residues in the bottom-right of the picture correspond to T591 in AAV8 (red spheres) and R588 in AAV2 (cyan sphere).

AAV8 contains the residues S315 and T591 which correspond to the following residues in ttAAV2: S312 and T588. The corresponding residues in wtAAV2, namely N312 and R588, are at perfectly matching positions on the VP1 3D structures (FIG. 24). Therefore in particular embodiments the following mutations are made in AAV8 capsid sequence: S315N, T591R.

In one embodiment, the improved transduction efficiency imparted by the S312N mutation in TT AAV2 may be transferred to the AAV8 serotype by applying the amino acid change S315N.

We mutated the AAV8 capsid sequence by site-directed mutagenesis and thereby created the AAV8-S315N vector plasmid. This plasmid was used to produce recombinant AAV8-S315N vectors expressing an ITR-containing CMV-GFP transgene by double transfection of 293T cells. The vector was then purified from the cell lysate and from the harvested culture supernatant by FPLC affinity chromatography, using an AVB sepharose resin. The capsid titer and vector genome titer were assessed by SDS-PAGE and qPCR, respectively.

The mutant AAV8-S315N vector, expressing GFP, is screened by systemic injections in CD1 neonatal mice. A titer-matched AAV8 vector is used as a control. GFP expression obtained in various organs after intra-jugular injection of $2\times10^{11}$ vg is then analysed, primarily focusing on the liver where AAV8 has previously shown some strong transduction efficiency.

5) Modification of the AAV9 Serotype

Figure 25:
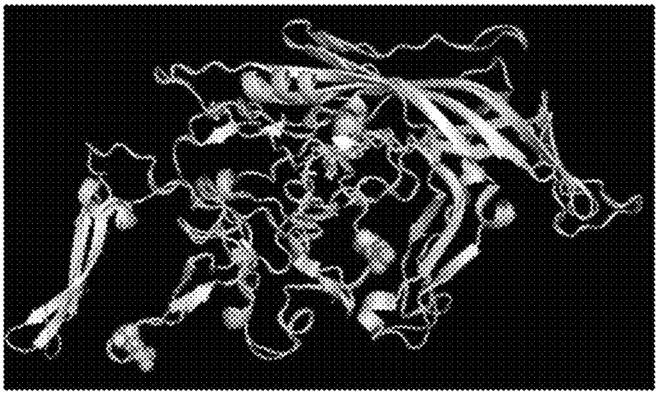
FIG. 25 Three-dimensional representation of an alignment between VP1 capsid monomer from AAV2 (light blue) and VP1 monomer from AAV9 (green). The highlighted residues in the middle of the picture correspond to G549 in AAV9 (yellow spheres) and E548 in AAV2 (cyan sphere). The highlighted residues in the bottom-left of the picture correspond to S586 in AAV9 (yellow spheres) and R585 in AAV2 (cyan sphere).

AAV9 contains the residues S162, S205, G549 and S586 which correspond to the following residues in ttAAV2: S162, S205, G548 and S585. The corresponding residues in AAV2, namely A162, T205, E548 and R585, are at perfectly matching positions on the VP1 3D structures (FIG. 25). Therefore in particular embodiments the following mutations are made in AAV8 capsid sequence: S162A, S205T, G549E, and S586R.

6) Modification of the AAVrh10 Serotype

AAVrh10 contains the residue G551 which corresponds with G548 with ttAAV2. Considering how conserved this residue and position appears among the various serotypes, we assume that G551 in AAVrh10 will align with E548 in wtAAV2 three-dimensionally. Therefore in one embodiment the following mutation is made in AAVrh10 capsid sequence: G551E.

7) Modification of the AAV3B and AAV-LK03 Serotypes

Similarly to the AAV8 serotype, we observed that the AAV3B serotype also contains an internal serine at position 312 after aligning the capsid protein VP1 sequence with the one from AAV-TT (see AAV3B capsid sequence in FIG. 38).

The newly described LK03 AAV vector, a chimeric capsid composed of five different parental AAV capsids engineered by M. A. Kay by DNA-shuffling, also contains the residue S312 in the internal side of the capsid (see Lisowski et al., Selection and evaluation of clinically relevant AAV variants in a xenograft liver model, Nature 506, 382-386 (2014)). The capsid sequence of AAV-LK03 is disclosed in WO2013/029030 and shown in FIG. 39.

Therefore in further embodiments, the AAV3B and the AAV-LK03 vectors are mutated by applying the amino-acid change S312N in both vectors. These new mutants, and their corresponding AAV control serotypes, are also tested by intra-jugular injections in neonatal mice. The GFP expression obtained in various harvested organs is then analysed.

Example 6

Identification of ttAAV2-Specific Amino Acids that are Transferable Between AAV Serotypes In further embodiments, the key amino acids identified during the ttAAV2 characterization are inserted into the other prominent serotypes at the relevant positions. The newly engineered vectors are then tested using the appropriate non-mutated serotypes as controls. This validates the importance of individual amino acids at specific positions on AAV capsids, independently of the serotype.

1) Residues S585, T588, S312, D546, G548 and S593

AAV1, AAV5 and AAV6 naturally contain the same amino acid residue at positions in their capsid protein sequences corresponding to G548, S585 and T588 in ttAAV2. Therefore in further embodiments, the capsid proteins in these serotypes are mutated at matching positions to include the other residues S312, D546, and S593 present in ttAAV2. Similarly AAV8, which already contains the same amino acid residue as in ttAAV2 at positions corresponding to S312 and T588 in ttAAV2, is further mutated to contain residues corresponding to S585, D546, G548 and S593 in ttAAV2. AAV9, that already contains corresponding residues to G548 and S585 in ttAAV2, is mutated to include residues corresponding to T588, S312, D546 and S593 in ttAAV2. Finally AAV10, which already contains a residue corresponding to G548, is further modified to also contain residues corresponding to S585, T588, S312, G548 and S593.

2) Residues I125, A151, S162, S205, M457, A492, D499 and Y533

AAV1, and AAV6 already naturally contain the residue S205. Therefore in further embodiments these serotypes are mutated at positions corresponding to the residues I125, A151, S162, M457, A492, D499 and Y533 in ttAAV2. Similarly AAV9, that already contains the residues S162 and S205, is further mutated to contain residues corresponding to I125, A151, M457, A492, D499 and Y533 in ttAAV2. Finally, AAV5, 8 and 10 are modified to display residues corresponding to I125, A151, S162, S205, M457, A492, D499 and Y533 in ttAAV2.

The positions the mutations present in ttAAV2 and the corresponding residues present in the wild type capsid protein VP1 sequences of other AAV serotypes are shown in Table 1 below. In general, variant non-AAV2 vectors can be constructed by mutating any of the residues shown in Table 1 for these serotypes. The residues shown in italics are residues which are already present in ttAAV2 at a corresponding position. In preferred embodiment, the non-AAV2 serotypes are mutated at one or more the residues shown in non-italic script. In this ways, the advantageous properties shown by ttAAV2 can be transferred into alternative AAV serotypes.

TABLE 1

| ttAAV2 | AAV1 | AAV5 | AAV6 | AAV8 | AAV9 | AAV10 |
|---|---|---|---|---|---|---|
| I125 | V125 | V124 | V125 | V125 | L125 | V125 |
| A151 | Q151 | K150 | Q151 | Q151 | Q151 | Q151 |

TABLE 1-continued

| ttAAV2 | AAV1 | AAV5 | AAV6 | AAV8 | AAV9 | AAV10 |
|---|---|---|---|---|---|---|
| S162 | T162 | K153 | T162 | K163 | *S162* | K163 |
| S205 | *S205* | A195 | *S205* | A206 | *S205* | A206 |
| S312 | N313 | R303 | N313 | S315 | N314 | N315 |
| M457 | N458 | T444 | N458 | T460 | Q458 | T460 |
| A492 | K493 | S479 | K493 | T495 | V493 | L495 |
| D499 | N500 | V486 | N500 | N502 | E500 | N502 |
| Y533 | F534 | T520 | F534 | F536 | F534 | F536 |
| D546 | S547 | P533 | S547 | N549 | G547 | G549 |
| G548 | *G549* | *G537* | *G549* | A551 | *G549* | *G551* |
| S585 | *S586* | *S575* | *S586* | Q588 | *S586* | Q588 |
| T588 | *T589* | *T578* | *T589* | *T591* | A589 | A591 |
| S593 | G594 | G583 | G594 | G596 | G594 | G596 |

FURTHER EMBODIMENTS OF THE INVENTION

The invention also relates additional aspects, as defined in the following summary paragraphs:

1. A recombinant adeno-associated virus (AAV) vector comprising;
(a) a variant AAV capsid protein, wherein the variant AAV capsid protein comprises at least one amino acid substitution with respect to a wild type AAV capsid protein; wherein the at least one amino acid substitution is present at a position corresponding to one or more of the following positions in an AAV2 capsid protein sequence: 125, 151, 162, 205, 312, 457, 492, 499, 533, 546, 548, 585, 588 and/or 593; and
(b) a heterologous nucleic acid comprising a nucleotide sequence encoding a gene product.

2. A recombinant AAV vector according to paragraph 1, wherein (i) the vector comprises a variant AAV2 capsid protein; (ii) the variant AAV capsid protein comprises a sequence of SEQ ID NO:2, or a sequence having at least 95% sequence identity thereto; (iii) the wild type AAV capsid protein is from AAV2; and/or (iv) the wild type AAV capsid protein comprises a sequence of SEQ ID NO:1.

3. A recombinant AAV vector according to paragraph 2, wherein the variant AAV2 capsid protein comprises one or more of the following residues: I125, A151, S162, S205, S312, M457, A492, D499, Y533, D546, G548, S585, T588 and/or S593.

4. A recombinant AAV vector according to paragraph 2 or paragraph 3, wherein the variant AAV2 capsid protein comprises one or more of the following amino acid substitutions with respect to a wild type AAV2 capsid protein: V125I, V151A, A162S, T205S, N312S, Q457M, S492A, E499D, F533Y, G546D, E548G, R585S, R588T and/or A593S.

5. A recombinant AAV vector according to any of paragraphs 1 to 3, wherein the variant AAV capsid protein is from AAV1, AAV5, AAV6, AAV8, AAV9 or AAV10.

6. A recombinant AAV vector according to paragraph 5, wherein (i) the vector comprises a variant AAV1 capsid protein, (ii) the variant AAV capsid protein comprises a sequence having at least 95% sequence identity to SEQ ID NO:3; (iii) the wild type AAV capsid protein is from AAV1; and/or (iv) the wild type AAV capsid protein comprises a sequence of SEQ ID NO:3;
and wherein at least one amino acid substitution is present at one or more of the following positions in the AAV1 capsid protein sequence: 125, 151, 162, 205, 313, 458, 493, 500, 534, 547, 549, 586, 589 and/or 594.

7. A recombinant AAV vector according to paragraph 6, wherein the variant AAV1 capsid protein comprises one or more of the following amino acid substitutions with respect to a wild type AAV1 capsid protein:
(a) V125I, Q151A, T162S, N313S, N458M, K493A, N500D, F534Y, S547D, and/or G594S; and/or
(b) S205T, G549E, S586R and/or T589R.
8. A recombinant AAV vector according to paragraph 5, wherein (i) the vector comprises a variant AAV5 capsid protein, (ii) the variant AAV capsid protein comprises a sequence having at least 95% sequence identity to SEQ ID NO:4; (iii) the wild type AAV capsid protein is from AAV5; and/or (iv) the wild type AAV capsid protein comprises a sequence of SEQ ID NO:4;
and wherein at least one amino acid substitution is present at one or more of the following positions in the AAV5 capsid protein sequence: 124, 150, 153, 195, 303, 444, 479, 486, 520, 533, 537, 575, 578 and/or 583.
9. A recombinant AAV vector according to paragraph 8, wherein the variant AAV5 capsid protein comprises one or more of the following amino acid substitutions with respect to a wild type AAV5 capsid protein:
(a) V124I, K150A, K153S, A195S, R303S, T444M, S479A, V486D, T520Y, P533D, and/or G583S; and/or
(b) G537E, S575R and/or T578R.
10. A recombinant AAV vector according to paragraph 5, wherein (i) the vector comprises a variant AAV6 capsid protein, (ii) the variant AAV capsid protein comprises a sequence having at least 95% sequence identity to SEQ ID NO:5; (iii) the wild type AAV capsid protein is from AAV6; and/or (iv) the wild type AAV capsid protein comprises a sequence of SEQ ID NO:5;
and wherein at least one amino acid substitution is present at one or more of the following positions in the AAV6 capsid protein sequence: 125, 151, 162, 205, 313, 458, 493, 500, 534, 547, 549, 586, 589 and/or 594.
11. A recombinant AAV vector according to paragraph 10, wherein the variant AAV6 capsid protein comprises one or more of the following amino acid substitutions with respect to a wild type AAV6 capsid protein:
(a) V125I, Q151A, T162S, N313S, N458M, K493A, N500D, F534Y, S547D, and/or G594S; and/or
(b) S205T, G549E, S586R and/or T589R.
12. A recombinant AAV vector according to paragraph 5, wherein (i) the vector comprises a variant AAV8 capsid protein, (ii) the variant AAV capsid protein comprises a sequence having at least 95% sequence identity to SEQ ID NO:6; (iii) the wild type AAV capsid protein is from AAV8; and/or (iv) the wild type AAV capsid protein comprises a sequence of SEQ ID NO:6;
and wherein at least one amino acid substitution is present at one or more of the following positions in the AAV8 capsid protein sequence: 125, 151, 163, 206, 315, 460, 495, 502, 536, 549, 551, 588, 591 and/or 596.
13. A recombinant AAV vector according to paragraph 12, wherein the variant AAV8 capsid protein comprises one or more of the following amino acid substitutions with respect to a wild type AAV8 capsid protein:
(a) V125I, Q151A, K163S, A206S, T460M, T495A, N502D, F536Y, N549D, A551G, Q588S and/or G596S; and/or
(b) S315N and/or T591R.
14. A recombinant AAV vector according to paragraph 5, wherein (i) the vector comprises a variant AAV9 capsid protein, (ii) the variant AAV capsid protein comprises a sequence having at least 95% sequence identity to SEQ ID NO:7; (iii) the wild type AAV capsid protein is from AAV9; and/or (iv) the wild type AAV capsid protein comprises a sequence of SEQ ID NO:7;
and wherein at least one amino acid substitution is present at one or more of the following positions in the AAV9 capsid protein sequence: 125, 151, 162, 205, 314, 458, 493, 500, 534, 547, 549, 586, 589 and/or 594.
15. A recombinant AAV vector according to paragraph 14, wherein the variant AAV9 capsid protein comprises one or more of the following amino acid substitutions with respect to a wild type AAV9 capsid protein:
(a) L125I, Q151A, N314S, Q458M, V493A, E500D, F534Y, G547D, A589T and/or G594S; and/or
(b) S162A, S205T, G549E and/or S586R.
16. A recombinant AAV vector according to paragraph 5, wherein (i) the vector comprises a variant AAVrh10 capsid protein, (ii) the variant AAV capsid protein comprises a sequence having at least 95% sequence identity to SEQ ID NO:8; (iii) the wild type AAV capsid protein is from AAVrh10; and/or (iv) the wild type AAV capsid protein comprises a sequence of SEQ ID NO:8;
and wherein at least one amino acid substitution is present at one or more of the following positions in the AAV10 capsid protein sequence: 125, 151, 163, 206, 315, 460, 495, 502, 536, 549, 551, 588, 591 and/or 596.
17. A recombinant AAV vector according to paragraph 16, wherein the variant AAVrh10 capsid protein comprises one or more of the following amino acid substitutions with respect to a wild type AAVrh10 capsid protein:
(a) V125I, Q151A, K163S, A206S, N315S, T460M, L495A, N502D, F536Y, G549D, Q588S, A591T and/or G596S; and/or
(b) G551E.
18. A recombinant AAV vector according to any preceding paragraph, wherein the recombinant AAV vector exhibits increased transduction of a neuronal or retinal tissue compared to an AAV vector comprising a corresponding wild type AAV capsid protein.
19. A recombinant AAV vector according to any preceding paragraph, wherein the gene product comprises an interfering RNA or an aptamer.
20. A recombinant AAV vector according to any of paragraphs 1 to 18, wherein the gene product comprises a polypeptide.
21. A recombinant AAV vector according to paragraph 20, wherein the gene product comprises a neuroprotective polypeptide, an anti-angiogenic polypeptide, or a polypeptide that enhances function of a neuronal or retinal cell.
22. A recombinant AAV vector according to paragraph 21, wherein the gene product comprises glial derived neurotrophic factor, fibroblast growth factor, nerve growth factor, brain derived neurotrophic factor, rhodopsin, retinoschisin, RPE65 or peripherin.
23. A pharmaceutical composition comprising:
(a) a recombinant AAV vector according to any preceding paragraph; and
(b) a pharmaceutically acceptable excipient.
24. A method for delivering a gene product to a neuronal or retinal tissue in a subject, the method comprising administering to the subject a recombinant AAV vector or pharmaceutical composition according to any preceding paragraph.
25. A method for treating a neurological or ocular disorder, the method comprising administering to the subject a recombinant AAV vector or pharmaceutical composition according to any preceding paragraph.
26. A recombinant AAV vector or pharmaceutical composition according to any of paragraphs 1 to 23, for use in treating a neurological or ocular disorder.

27. A method, recombinant AAV vector or pharmaceutical composition for use according to any of paragraphs 24 to 26, wherein the neurological disorder is a neurodegenerative disease.

28. A method, recombinant AAV vector or pharmaceutical composition for use according to any of paragraphs 24 to 26, wherein the ocular disorder is glaucoma, retinitis pigmentosa, macular degeneration, retinoschisis or diabetic retinopathy.

29. An isolated variant AAV capsid protein, wherein the variant AAV capsid protein comprises at least one amino acid substitution with respect to a wild type AAV capsid protein; wherein the at least one amino acid substitution is present at one or more of the following positions in an AAV2 capsid protein sequence: 125, 151, 162, 205, 312, 457, 492, 499, 533, 546, 548, 585, 588 and/or 593; or at one or more corresponding positions in an alternative AAV capsid protein sequence.

30. An isolated nucleic acid comprising a nucleotide sequence that encodes a variant AAV capsid protein as defined in paragraph 29.

31. An isolated host cell comprising a nucleic acid as defined in paragraph 30.

The invention claimed is:

1. A recombinant AAV (rAAV) for transducing neuronal tissue comprising:

(a) an AAV capsid in which the VP1 protein has the sequence of SEQ ID NO:2 and (b) a heterologous polynucleotide packaged in the AAV capsid, said heterologous polynucleotide comprising AAV inverted terminal repeats (ITRs), a transgene encoding a gene product, and one or more regulatory sequences that directs expression of the transgene, wherein the transgene is selected for therapeutic expression in a human neuronal tissue.

2. The rAAV of claim 1, wherein the AAV capsid enables retrograde transport of the transgene product.

3. The rAAV of claim 1, wherein the human neuronal tissue is human cortex, striatum, or hippocampus.

4. A method of treating a neurological disorder or condition in a patient comprising administering a recombinant AAV (rAAV) of claim 1.

5. The method of claim 4, wherein the neurological disorder or condition is a neurodegenerative disease.

6. The method of claim 5, wherein the neurodegenerative disease is selected from the group consisting of Alzheimer's Disease, Parkinson's Disease, amyotrophic lateral sclerosis (ALS), spinal muscular atrophy, cerebella degeneration, schizophrenia, epilepsy, ischemia-related disease and stroke.

7. The method of claim 6, wherein the neurodegenerative disease is epilepsy.

* * * * *

```
                              SEQUENCE LISTING

<160> NUMBER OF SEQ ID NOS: 12

<210> SEQ ID NO 1
<211> LENGTH: 735
<212> TYPE: PRT
<213> ORGANISM: Adeno-associated virus-2

<400> SEQUENCE: 1

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285
```

-continued

```
Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700
```

-continued

```
Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735


<210> SEQ ID NO 2
<211> LENGTH: 735
<212> TYPE: PRT
<213> ORGANISM: Artificial sequence
<220> FEATURE:
<223> OTHER INFORMATION: Synthetic sequence: Amino acid sequence of
      true-type adeno-associated virus 2 (ttAAV2) capsid protein VP1

<400> SEQUENCE: 2

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Ala Glu Pro Asp Ser Ser Ser Gly Thr Gly
145                 150                 155                 160

Lys Ser Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Ser Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335
```

-continued

```
Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Met Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ala Ala Asp Asn Asn
                485                 490                 495

Asn Ser Asp Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Tyr Phe Pro Gln Ser Gly Val Leu Ile Phe Gly Lys
    530                 535                 540

Gln Asp Ser Gly Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Ser Gly Asn Thr Gln Ala Ala Thr
            580                 585                 590

Ser Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735
```

<210> SEQ ID NO 3
<211> LENGTH: 736

<212> TYPE: PRT
<213> ORGANISM: Adeno-associated virus-1

<400> SEQUENCE: 3

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400
```

Ser Gln Met Leu Arg Thr Gly Asn Asn Phe Thr Phe Ser Tyr Thr Phe
405 410 415

Glu Glu Val Pro Phe His Ser Ser Tyr Ala His Ser Gln Ser Leu Asp
420 425 430

Arg Leu Met Asn Pro Leu Ile Asp Gln Tyr Leu Tyr Tyr Leu Asn Arg
435 440 445

Thr Gln Asn Gln Ser Gly Ser Ala Gln Asn Lys Asp Leu Leu Phe Ser
450 455 460

Arg Gly Ser Pro Ala Gly Met Ser Val Gln Pro Lys Asn Trp Leu Pro
465 470 475 480

Gly Pro Cys Tyr Arg Gln Gln Arg Val Ser Lys Thr Lys Thr Asp Asn
485 490 495

Asn Asn Ser Asn Phe Thr Trp Thr Gly Ala Ser Lys Tyr Asn Leu Asn
500 505 510

Gly Arg Glu Ser Ile Ile Asn Pro Gly Thr Ala Met Ala Ser His Lys
515 520 525

Asp Asp Glu Asp Lys Phe Phe Pro Met Ser Gly Val Met Ile Phe Gly
530 535 540

Lys Glu Ser Ala Gly Ala Ser Asn Thr Ala Leu Asp Asn Val Met Ile
545 550 555 560

Thr Asp Glu Glu Glu Ile Lys Ala Thr Asn Pro Val Ala Thr Glu Arg
565 570 575

Phe Gly Thr Val Ala Val Asn Phe Gln Ser Ser Ser Thr Asp Pro Ala
580 585 590

Thr Gly Asp Val His Ala Met Gly Ala Leu Pro Gly Met Val Trp Gln
595 600 605

Asp Arg Asp Val Tyr Leu Gln Gly Pro Ile Trp Ala Lys Ile Pro His
610 615 620

Thr Asp Gly His Phe His Pro Ser Pro Leu Met Gly Gly Phe Gly Leu
625 630 635 640

Lys Asn Pro Pro Pro Gln Ile Leu Ile Lys Asn Thr Pro Val Pro Ala
645 650 655

Asn Pro Pro Ala Glu Phe Ser Ala Thr Lys Phe Ala Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Val Gln Tyr Thr Ser Asn
690 695 700

Tyr Ala Lys Ser Ala Asn Val Asp Phe Thr Val Asp Asn Asn Gly Leu
705 710 715 720

Tyr Thr Glu Pro Arg Pro Ile Gly Thr Arg Tyr Leu Thr Arg Pro Leu
725 730 735

<210> SEQ ID NO 4
<211> LENGTH: 724
<212> TYPE: PRT
<213> ORGANISM: Adeno-associated virus-5

<400> SEQUENCE: 4

Met Ser Phe Val Asp His Pro Pro Asp Trp Leu Glu Glu Val Gly Glu
1 5 10 15

Gly Leu Arg Glu Phe Leu Gly Leu Glu Ala Gly Pro Pro Lys Pro Lys
20 25 30

Pro Asn Gln Gln His Gln Asp Gln Ala Arg Gly Leu Val Leu Pro Gly

-continued

```
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460
```

```
Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu


<210> SEQ ID NO 5
<211> LENGTH: 736
<212> TYPE: PRT
<213> ORGANISM: Adeno-associated virus-6

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110
```

-continued

```
Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525
```

-continued

```
Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735


<210> SEQ ID NO 6
<211> LENGTH: 738
<212> TYPE: PRT
<213> ORGANISM: Adeno-associated virus-8

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175
```

-continued

```
Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590
```

Pro Gln Ile Gly Thr Val Asn Ser Gln Gly Ala Leu Pro Gly Met Val
595 600 605

Trp Gln Asn Arg Asp Val Tyr Leu Gln Gly Pro Ile Trp Ala Lys Ile
610 615 620

Pro His Thr Asp Gly Asn Phe His Pro Ser Pro Leu Met Gly Gly Phe
625 630 635 640

Gly Leu Lys His Pro Pro Pro Gln Ile Leu Ile Lys Asn Thr Pro Val
645 650 655

Pro Ala Asp Pro Pro Thr Thr Phe Asn Gln Ser Lys Leu Asn Ser Phe
660 665 670

Ile Thr Gln Tyr Ser Thr Gly Gln Val Ser Val Glu Ile Glu Trp Glu
675 680 685

Leu Gln Lys Glu Asn Ser Lys Arg Trp Asn Pro Glu Ile Gln Tyr Thr
690 695 700

Ser Asn Tyr Tyr Lys Ser Thr Ser Val Asp Phe Ala Val Asn Thr Glu
705 710 715 720

Gly Val Tyr Ser Glu Pro Arg Pro Ile Gly Thr Arg Tyr Leu Thr Arg
725 730 735

Asn Leu

<210> SEQ ID NO 7
<211> LENGTH: 736
<212> TYPE: PRT
<213> ORGANISM: Adeno-associated virus-9

<400> SEQUENCE: 7

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Gln Pro
20 25 30

Lys Ala Asn Gln Gln His Gln Asp Asn Ala Arg Gly Leu Val Leu Pro
35 40 45

Gly Tyr Lys Tyr Leu Gly Pro Gly Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Leu Leu Glu Pro
115 120 125

Leu Gly Leu Val Glu Glu Ala Ala Lys Thr Ala Pro Gly Lys Lys Arg
130 135 140

Pro Val Glu Gln Ser Pro Gln Glu Pro Asp Ser Ser Ala Gly Ile Gly
145 150 155 160

Lys Ser Gly Ala Gln Pro Ala Lys Lys Arg Leu Asn Phe Gly Gln Thr
165 170 175

Gly Asp Thr Glu Ser Val Pro Asp Pro Gln Pro Ile Gly Glu Pro Pro
180 185 190

Ala Ala Pro Ser Gly Val Gly Ser Leu Thr Met Ala Ser Gly Gly Gly
195 200 205

Ala Pro Val Ala Asp Asn Asn Glu Gly Ala Asp Gly Val Gly Ser Ser
210 215 220

-continued

```
Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
```

-continued

```
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 8
<211> LENGTH: 738
<212> TYPE: PRT
<213> ORGANISM: Adeno-associated virus-10

<400> SEQUENCE: 8

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285
```

-continued

```
Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
```

-continued 705 710 715 720

Gly Thr Tyr Ser Glu Pro Arg Pro Ile Gly Thr Arg Tyr Leu Thr Arg
725 730 735

Asn Leu

<210> SEQ ID NO 9
<211> LENGTH: 738
<212> TYPE: PRT
<213> ORGANISM: Adeno-associated virus 10

<400> SEQUENCE: 9

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Lys Ala Gly Asp Asn Pro Tyr Leu Arg Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Ala Ala Lys Thr Ala Pro Gly Lys Lys Arg
130 135 140

Pro Val Glu Pro Ser Pro Gln Arg Ser Pro Asp Ser Ser Thr Gly Ile
145 150 155 160

Gly Lys Lys Gly Gln Gln Pro Ala Lys Lys Arg Leu Asn Phe Gly Gln
165 170 175

Thr Gly Glu Ser Glu Ser Val Pro Asp Pro Gln Pro Ile Gly Glu Pro
180 185 190

Pro Ala Gly Pro Ser Gly Leu Gly Ser Gly Thr Met Ala Ala Gly Gly
195 200 205

Gly Ala Pro Met Ala Asp Asn Asn Glu Gly Ala Asp Gly Val Gly Ser
210 215 220

Ser Ser Gly Asn Trp His Cys Asp Ser Thr Trp Leu Gly Asp Arg Val
225 230 235 240

Ile Thr Thr Ser Thr Arg Thr Trp Ala Leu Pro Thr Tyr Asn Asn His
245 250 255

Leu Tyr Lys Gln Ile Ser Asn Gly Thr Ser Gly Gly Ser Thr Asn Asp
260 265 270

Asn Thr Tyr Phe Gly Tyr Ser Thr Pro Trp Gly Tyr Phe Asp Phe Asn
275 280 285

Arg Phe His Cys His Phe Ser Pro Arg Asp Trp Gln Arg Leu Ile Asn
290 295 300

Asn Asn Trp Gly Phe Arg Pro Lys Arg Leu Ser Phe Lys Leu Phe Asn
305 310 315 320

Ile Gln Val Lys Glu Val Thr Gln Asn Glu Gly Thr Lys Thr Ile Ala
325 330 335

Asn Asn Leu Thr Ser Thr Ile Gln Val Phe Thr Asp Ser Glu Tyr Gln

-continued

```
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Ala Asn Thr Gly
            580                 585                 590

Pro Ile Val Gly Asn Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 10
<211> LENGTH: 744
```

<212> TYPE: PRT
<213> ORGANISM: Artificial sequence
<220> FEATURE:
<223> OTHER INFORMATION: Consensus sequence
<220> FEATURE:
<221> NAME/KEY: SITE
<222> LOCATION: (148)..(148)
<223> OTHER INFORMATION: Xaa indicates no overall consensus with any amino acid
<220> FEATURE:
<221> NAME/KEY: SITE
<222> LOCATION: (202)..(202)
<223> OTHER INFORMATION: Xaa indicates no overall consensus with any amino acid
<220> FEATURE:
<221> NAME/KEY: SITE
<222> LOCATION: (207)..(207)
<223> OTHER INFORMATION: Xaa indicates no overall consensus with any amino acid
<220> FEATURE:
<221> NAME/KEY: SITE
<222> LOCATION: (270)..(270)
<223> OTHER INFORMATION: Xaa indicates no overall consensus with any amino acid
<220> FEATURE:
<221> NAME/KEY: SITE
<222> LOCATION: (458)..(458)
<223> OTHER INFORMATION: Xaa indicates no overall consensus with any amino acid
<220> FEATURE:
<221> NAME/KEY: SITE
<222> LOCATION: (462)..(462)
<223> OTHER INFORMATION: Xaa indicates no overall consensus with any amino acid
<220> FEATURE:
<221> NAME/KEY: SITE
<222> LOCATION: (465)..(465)
<223> OTHER INFORMATION: Xaa indicates no overall consensus with any amino acid
<220> FEATURE:
<221> NAME/KEY: SITE
<222> LOCATION: (474)..(474)
<223> OTHER INFORMATION: Xaa indicates no overall consensus with any amino acid
<220> FEATURE:
<221> NAME/KEY: SITE
<222> LOCATION: (496)..(496)
<223> OTHER INFORMATION: Xaa indicates no overall consensus with any amino acid
<220> FEATURE:
<221> NAME/KEY: SITE
<222> LOCATION: (498)..(498)
<223> OTHER INFORMATION: Xaa indicates no overall consensus with any amino acid
<220> FEATURE:
<221> NAME/KEY: SITE
<222> LOCATION: (500)..(500)
<223> OTHER INFORMATION: Xaa indicates no overall consensus with any amino acid
<220> FEATURE:
<221> NAME/KEY: SITE
<222> LOCATION: (538)..(538)
<223> OTHER INFORMATION: Xaa indicates no overall consensus with any amino acid
<220> FEATURE:
<221> NAME/KEY: SITE
<222> LOCATION: (557)..(557)
<223> OTHER INFORMATION: Xaa indicates no overall consensus with any amino acid
<220> FEATURE:
<221> NAME/KEY: SITE
<222> LOCATION: (562)..(563)
<223> OTHER INFORMATION: Xaa indicates no overall consensus with any amino acid
<220> FEATURE:
<221> NAME/KEY: SITE
<222> LOCATION: (565)..(565)
<223> OTHER INFORMATION: Xaa indicates no overall consensus with any amino acid -continued
<220> FEATURE:
<221> NAME/KEY: SITE
<222> LOCATION: (570)..(570)
<223> OTHER INFORMATION: Xaa indicates no overall consensus with any amino acid
<220> FEATURE:
<221> NAME/KEY: SITE
<222> LOCATION: (587)..(587)
<223> OTHER INFORMATION: Xaa indicates no overall consensus with any amino acid
<220> FEATURE:
<221> NAME/KEY: SITE
<222> LOCATION: (598)..(598)
<223> OTHER INFORMATION: Xaa indicates no overall consensus with any amino acid
<220> FEATURE:
<221> NAME/KEY: SITE
<222> LOCATION: (675)..(675)
<223> OTHER INFORMATION: Xaa indicates no overall consensus with any amino acid

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Xaa Ser Pro Gln Arg Glu Pro Asp Ser Ser Ser Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Gly Pro Gln Pro Leu Gly Glu
            180                 185                 190

Pro Pro Ala Ala Pro Ser Gly Leu Gly Xaa Asn Thr Met Ala Xaa Gly
        195                 200                 205

Gly Gly Ala Pro Met Ala Asp Asn Asn Glu Gly Ala Asp Gly Val Gly
    210                 215                 220

Asn Ser Ser Gly Asn Trp His Cys Asp Ser Thr Trp Leu Gly Asp Arg
225                 230                 235                 240

Val Ile Thr Thr Ser Thr Arg Thr Trp Ala Leu Pro Thr Tyr Asn Asn
                245                 250                 255

His Leu Tyr Lys Gln Ile Ser Ser Gly Ser Ser Gly Gly Xaa Ser Asn
            260                 265                 270

Asp Asn His Tyr Phe Gly Tyr Ser Thr Pro Trp Gly Tyr Phe Asp Phe
        275                 280                 285

Asn Arg Phe His Cys His Phe Ser Pro Arg Asp Trp Gln Arg Leu Ile
    290                 295                 300
```

-continued

```
Asn Asn Asn Trp Gly Phe Arg Pro Lys Arg Leu Asn Phe Lys Leu Phe
305                 310                 315                 320

Asn Ile Gln Val Lys Glu Val Thr Gln Asn Asp Gly Thr Thr Thr Ile
                325                 330                 335

Ala Asn Asn Leu Thr Ser Thr Val Gln Val Phe Thr Asp Ser Glu Tyr
            340                 345                 350

Gln Leu Pro Tyr Val Leu Gly Ser Ala His Gln Gly Cys Leu Pro Pro
        355                 360                 365

Phe Pro Ala Asp Val Phe Met Ile Pro Gln Tyr Gly Tyr Leu Thr Leu
    370                 375                 380

Asn Arg Asp Asn Gly Ser Gln Ala Val Gly Arg Ser Ser Phe Tyr Cys
385                 390                 395                 400

Leu Glu Tyr Phe Pro Ser Gln Met Leu Arg Thr Gly Asn Asn Phe Thr
                405                 410                 415

Phe Ser Tyr Thr Phe Glu Asp Val Pro Phe His Ser Ser Tyr Ala His
            420                 425                 430

Ser Gln Ser Leu Asp Arg Leu Met Asn Pro Leu Ile Asp Gln Tyr Leu
        435                 440                 445

Tyr Tyr Leu Ser Arg Thr Gln Asn Thr Xaa Gly Thr Ala Xaa Thr Gln
    450                 455                 460

Xaa Leu Leu Phe Ser Gln Ala Gly Pro Xaa Asn Met Ser Val Gln Ala
465                 470                 475                 480

Lys Asn Trp Leu Pro Gly Pro Cys Tyr Arg Gln Gln Arg Val Ser Xaa
                485                 490                 495

Thr Xaa Thr Xaa Asn Asn Asn Ser Asn Phe Ala Trp Thr Gly Ala Thr
            500                 505                 510

Lys Tyr His Leu Asn Gly Arg Asp Ser Leu Val Asn Pro Gly Pro Ala
        515                 520                 525

Met Ala Ser His Lys Asp Asp Glu Glu Xaa Phe Phe Pro Ser Ser Gly
    530                 535                 540

Val Leu Ile Phe Gly Lys Gln Gly Ala Asn Pro Gly Xaa Asp Asn Val
545                 550                 555                 560

Asp Xaa Xaa Gly Xaa Val Met Ile Thr Xaa Glu Glu Glu Ile Lys Thr
                565                 570                 575

Thr Asn Pro Val Ala Thr Glu Gln Tyr Gly Xaa Val Ala Thr Asn Leu
            580                 585                 590

Gln Ser Ser Asn Thr Xaa Pro Ala Thr Gly Asp Val Asn Ser Gln Gly
        595                 600                 605

Ala Leu Pro Gly Met Val Trp Gln Asp Arg Asp Val Tyr Leu Gln Gly
    610                 615                 620

Pro Ile Trp Ala Lys Ile Pro His Thr Asp Gly His Phe His Pro Ser
625                 630                 635                 640

Pro Leu Met Gly Gly Phe Gly Leu Lys His Pro Pro Pro Gln Ile Leu
                645                 650                 655

Ile Lys Asn Thr Pro Val Pro Ala Asn Pro Pro Thr Thr Phe Ser Ala
            660                 665                 670

Ala Lys Xaa Ala Ser Phe Ile Thr Gln Tyr Ser Thr Gly Gln Val Ser
        675                 680                 685

Val Glu Ile Glu Trp Glu Leu Gln Lys Glu Asn Ser Lys Arg Trp Asn
    690                 695                 700

Pro Glu Ile Gln Tyr Thr Ser Asn Tyr Tyr Lys Ser Thr Asn Val Asp
705                 710                 715                 720
```

-continued

```
Phe Ala Val Asp Thr Asn Gly Val Tyr Ser Glu Pro Arg Pro Ile Gly
                725                 730                 735

Thr Arg Tyr Leu Thr Arg Asn Leu
            740


<210> SEQ ID NO 11
<211> LENGTH: 736
<212> TYPE: PRT
<213> ORGANISM: Adeno-associated virus 3B

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350
```

```
Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 12
<211> LENGTH: 736
<212> TYPE: PRT
<213> ORGANISM: Artificial sequence
<220> FEATURE:

<223> OTHER INFORMATION: Recombinant sequence

<400> SEQUENCE: 12

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400
```

-continued

```
Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
                725                 730                 735
```